United States Patent
Tamareselvy et al.

(10) Patent No.: US 7,153,496 B2
(45) Date of Patent: *Dec. 26, 2006

(54) HAIR SETTING COMPOSITIONS, POLYMERS AND METHODS

(75) Inventors: Krishnan Tamareselvy, Brecksville, OH (US); Kittie L. Ramey, Cleveland, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 314 days.

This patent is subject to a terminal disclaimer.

(21) Appl. No.: 10/338,510

(22) Filed: Jan. 8, 2003

(65) Prior Publication Data

US 2003/0202953 A1  Oct. 30, 2003

Related U.S. Application Data

(60) Provisional application No. 60/349,608, filed on Jan. 18, 2002.

(51) Int. Cl.
*A61Q 5/06* (2006.01)

(52) U.S. Cl. .............. 424/70.11; 424/70.122; 424/70.16

(58) Field of Classification Search ........... 424/701, 424/702, 70.11, 70.16
See application file for complete search history.

(56) References Cited

U.S. PATENT DOCUMENTS

| | | | |
|---|---|---|---|
| 3,726,288 A | 4/1973 | Nowak et al. | |
| 4,196,190 A | 4/1980 | Gehman et al. | |
| 4,384,096 A | 5/1983 | Sonnabend | |
| 4,421,902 A | 12/1983 | Chang et al. | |
| 4,514,552 A | 4/1985 | Shay et al. | |
| 4,600,761 A | 7/1986 | Ruffner et al. | |
| 4,616,074 A | 10/1986 | Ruffner | |
| 4,743,698 A | 5/1988 | Ruffner et al. | |
| RE33,156 E | 1/1990 | Shay et al. | |
| 4,892,916 A | 1/1990 | Hawe et al. | |
| 4,902,499 A | 2/1990 | Bolish, Jr. et al. | |
| 4,904,772 A | 2/1990 | Sau | |
| 5,011,978 A | 4/1991 | Barron et al. | |
| 5,102,936 A | 4/1992 | Huth et al. | |
| 5,137,571 A | 8/1992 | Eisenhart et al. | |
| 5,191,051 A | 3/1993 | Shay et al. | |
| 5,292,843 A | 3/1994 | Jenkins et al. | |
| 5,294,692 A | 3/1994 | Barron et al. | |
| 5,362,415 A | 11/1994 | Egraz et al. | |
| 5,412,142 A | 5/1995 | Wilkerson, III et al. | |
| 5,639,841 A | 6/1997 | Jenkins | |
| 5,656,257 A | 8/1997 | Fealy et al. ............. | 424/70.13 |
| 5,770,760 A | 6/1998 | Robinson | |
| 5,916,967 A | 6/1999 | Jones et al. | |
| 5,972,356 A | 10/1999 | Peffly et al. ............. | 424/401 |
| 6,063,857 A | 5/2000 | Greenblatt et al. | |
| 6,074,439 A | 6/2000 | De La Mettrie et al. | |
| 6,106,578 A | 8/2000 | Jones | |
| 6,140,435 A | 10/2000 | Zanotti-Russo | |
| 6,190,647 B1 | 2/2001 | Karlen et al. | |
| 6,214,328 B1* | 4/2001 | Chang et al. ............. | 424/70.16 |
| 6,337,366 B1 | 1/2002 | Amick et al. | |
| 6,451,299 B1* | 9/2002 | Rigoletto et al. ........ | 424/70.16 |
| 2002/0042448 A1 | 4/2002 | Sorrentino et al. | |
| 2003/0012758 A1 | 1/2003 | Jourdan et al. .......... | 424/70.11 |

FOREIGN PATENT DOCUMENTS

| | | |
|---|---|---|
| EP | 0398576 | 11/1990 |
| EP | 0444791 | 9/1991 |
| EP | 0875241 | 11/1998 |
| EP | 1 038 892 A2 | 9/2000 |
| EP | 1138315 | 10/2001 |
| WO | 9635757 | 11/1996 |
| WO | WO 02/065996 | 8/2002 |

OTHER PUBLICATIONS

Bigoletto, Jr., R. et al., "Styleze™ 2000—A New Fixative Polymer for Gels-Formulation and Processing Guide (Part I)." *Soap & Cosmetics*, pp. 43-46, (Jul./Aug. 2001).

Bigoletto, Jr., R. et al., "Styleze™ 2000—A New Fixative Polymer for Gels-Formulation and Processing Guide (Part II)," *Soap & Cosmetics*, pp. 39-43, (Sep. 2001).

Shay, G.D., "Alkali-Swellable and Alkali-Soluble Thickener Technology—A Review," *Polymers in Aqueous Media—Performance Through Association*, Advances in Chemistry Services, 223, Ch. 25, pp. 457-494, The American Chemical Society (1989).

Diaz, P., et al., "Set Relaxation of Human Hair," *J. Soc. Cosmet. Chem.*, 34, pp. 205-212, (Jul. 1983).

(Continued)

*Primary Examiner*—Jyothsna Venkat
(74) *Attorney, Agent, or Firm*—Thoburn T. Dunlap

(57) ABSTRACT

Disclosed are aqueous hair setting compositions comprising, as the sole hair fixative component, rheology modifying, hair setting, associative polymers (RMHS), which are the polymerization product of a monomer mixture comprising an acidic vinyl monomer; and an associative monomer. The hair setting compositions provide surprisingly good to excellent hair setting efficacy, based on high humidity curl retention. A wide range of rheological characteristics was achieved together with good clarity and aesthetic product properties. Particularly preferred rheology modifying hair setting associative polymers are certain hydrophobically modified alkali-swellable and alkali-soluble associative polymers (ASAP) and HASE polymers disclosed herein. Also disclosed are methods of setting hair using RMHS polymer-containing compositions.

24 Claims, No Drawings

OTHER PUBLICATIONS

Jachowicz, J., et al., "Dynamic Hairspray Analysis. I. Instrumentation and Preliminary Results." *J. Soc. Cosmet. Chem.*, 47, pp. 73-84, (Mar./Apr. 1996).

Rieger, M.J., Ph.D. (ed.), *Harry's Cosmeticology, 8th Ed.*, Ch. 30, pp. 666-667, Chemical Publishing Co., Inc., New York, NY (2000).

L. Elton, et al., "Application of Acrylates/Methacrylates/Beheneth-25 Methacrylate Copolymer (Aculyn <8) as a Thickener and Suspending Agent in Cosmetic Formulations and as a Polymeric Emulsifier", Research Disclosure, Kenneth Mason Publications, Hampshire, GB, vol. 428, Dec. 1999, pp. 1553-1554.

\* cited by examiner

HAIR SETTING COMPOSITIONS, POLYMERS AND METHODS

CROSS-REFERENCE TO RELATED APPLICATION

This Application claims the priority of U.S. Provisional Application for Patent Ser. No. 60/349,608 filed on Jan. 18, 2002, which is incorporated herein by reference. The following related, commonly assigned, application was filed concurrently herewith: U.S. patent application Ser. No. 10/338,275, which claims priority from U.S. Provisional Application for Patent Ser. No. 60/349,399 filed on Jan. 18, 2002.

TECHNICAL FIELD OF THE INVENTION

This invention relates to the field of hair setting compositions, and in particular, to hair setting compositions containing certain rheology modifying, associative polymers as hair setting polymers.

BACKGROUND OF THE INVENTION

The desire to have one's hair retain a particular set or coiffure is widely held. A common methodology for accomplishing this is by applying hair setting compositions to the hair. Hair setting compositions can assist in manipulating (styling) the hair, and provide temporary benefits in holding the shape of the hair style (fixing) and maintaining the shine or appearance (grooming, restyling) of the coiffure during the day or between hair washing periods with water or shampoo, or between subsequent hair setting procedures.

Most commercial, hair setting compositions include hair setting polymers (styling or fixative), viscosity-increasing polymers, and polymer modifiers, in addition to solvents, co-solvents, and cosmetic adjuvants, such as preservatives, color, fragrance, and the like. The amount of hair setting polymer present can vary in the range of about 0.2 to about 10 weight percent, depending on the attributes desired during application and the function of the product. See, for example, Ch. 30, *Harry's Cosmeticology*, 8th Ed., M. J. Rieger, Ph.D. (ed.), 666–667, Chemical Publishing Co., Inc., New York, N.Y. (2000).

Various objective and subjective methods are used to measure the efficacy of a hair setting composition. One method commonly employed evaluates the resistance of the hair set to high humidity as a measure of the curl retention. In this methodology, hair tresses are curled either before or after applying the hair setting product to the hair, and the curl retention is periodically monitored during exposure to a controlled ambient room temperature and relative humidity (RH). When curl retention is measured under controlled ambient temperatures in the range of about 23 to about 27° C. and high humidity in the range of about 80–90% RH, it is commonly referred to as high humidity curl retention (HHCR). Most conventional hair setting formulations are marginally effective, typically providing an HHCR of about 70% of the initial curl for a period of not more than about 0.75 hours. Thus there is an ongoing need for an increase in the HHCR of hair setting formulations.

Hair setting compositions are also subjectively evaluated by visual and tactile sensory methods by examining, touching, combing, and brushing the hair, or instrumentally, for characteristics, such as appearance (shiny, clean, natural), feel (stiffness, tack-free, softness), curl memory (bounce, and restylability), combing ease, residue (flaking), static, smoothness, and the like. Conventional hair setting polymers also have a tendency to coat and dull the hair. Thus, there is an ongoing desire for non-dulling, hair setting polymers.

Also of importance are the aesthetic characteristics and appearance of hair setting compositions before, during, and after application to hair. Preferably, the product viscosity should be non-runny to avoid dripping during application. Product clarity is preferably substantially transparent or clear in order to obtain a "clean" product appearance. The product should be easy to spread, have a smooth texture, a non-tacky feel, and be able to dry relatively quickly on the hair.

Conventional polymeric hair styling or hair fixative polymers, well known in the art, include natural gums and resins and neutral or anionic polymers of synthetic origin. Some commercially available neutral or anionic polymers, which have been used as hair styling or fixative polymers include, for example, polyvinylpyrrolidone (PVP), polyvinylpyrrolidone/vinylacetate copolymer (PVP/VA), and acrylates/hydroxyesters acrylates copolymers (Rohm and Haas). For example, U.S. Pat. No. 4,196,190 to Gehman, et al., discloses an acrylic hair fixative resin made via emulsion polymerization techniques containing between 10 to 30 weight % of an alkyl acrylate, between 41 to 60 weight % of methyl methacrylate, between 5 to 20 weight % of hydroxyethyl methacrylate, and between 10 to 30 weight % of methacrylic acid. Acrylate/acrylamide copolymers (National Starch and BASF), ethyl and butyl esters of polyvinyl methyl ether/maleic anhydride copolymer (PVM/MA) (GANTREZ®, ISP), and a copolymer of vinylpyrrolidone/acrylic acid/lauryl methacrylate (STYLEZE™ 2000, ISP) are other examples.

One of the shortcomings of conventional hair setting resins and fixative polymers is that they generally do not provide significant thickening or contribute significant rheological modification at practical use concentrations. Consequently, conventional hair setting compositions typically require, in addition to the hair setting or fixative polymer, the addition of one or more viscosity-increasing thickener or gellant, such as a polymer, gum or resin, and other rheology modifying additives, such as emulsifiers, waxes, and the like, to achieve the desired rheological property. A few examples of synthetic and natural polymers that have been used as gellants in commercial hair fixative products include carbomer polyacrylic acid polymers, and hydrophobically-modified variations thereof, sold under the registered trademark CARBOPOL®, such as CARBOPOL® 980 polymer, CARBOPOL® 940 polymer, CARBOPOL® Ultrez 10 polymer, CARBOPOL® Ultrez 21 polymer, CARBOPOL® ETD 2020 polymer, and the like by Noveon, Inc., (Cleveland, Ohio), hydrophobically modified cellulose, xanthan gum and hydrophobically modified, alkali-swellable, emulsion polymers.

A prior art attempt to achieve a crosslinked acrylate polymer that was both a hair fixative and thickener was disclosed in U.S. Pat. No. 3,726,288 to Nowak, et al. However, the polymers disclosed were produced by an organic solvent-based polymerization process using toxic organic solvent (benzene) and, while thickening was achieved, hair fixative properties were weak (curl retention of less than 50% after 0.5 hours at 72° F. (about 22° C.) and 90% relative humidity).

Hydrophobically modified alkali-swellable and alkali-soluble emulsion polymers, conventionally referred to as HASE polymers, are associative polymers. An associative polymer contains pendant groups capable of forming non-specific "associations" with other groups in the polymer or other materials in the medium in which the polymer is present. Generally the pendant group has both hydrophobic and hydrophilic regions and the associations are generally based on hydrophobic interactions. Hydrogen bonding associations between hydrophilic groups have also been seen under some pH conditions. According to theory, such associations result in thickening by the formation of interpolymer networks above a critical polymer overlap concentration.

HASE polymers are typically polymerized as stable emulsions at low pH (pH<4.5) but become water swellable or soluble at near neutral to neutral pH (pH>5.5–7). Typical HASE polymers are vinyl addition copolymers of pH sensitive or hydrophilic monomers, hydrophobic monomers and an "associative monomer". The associative monomer has a polymerizable end group, a hydrophilic midsection and a hydrophobic end group. An extensive review of HASE polymers is found in Gregory D. Shay, Chapter 25, "Alkali-Swellable and Alkali-Soluble Thickener Technology A Review", *Polymers in Aqueous Media—Performance Through Association*, Advances in Chemistry Series 223, J. Edward Glass (ed.), ACS, pp. 457–494, Division Polymeric Materials, Washington, D.C. (1989), the relevant disclosures of which are incorporated herein by reference.

However, conventional hair setting and hair fixative polymers frequently are incompatible with the rheology modification agent or gellant resulting in loss of viscosity, lack of gel product clarity, and aggregation, coalescence, or coacervation. Consequently, hair fixative polymers suitable for use, especially in gel formulations, may be limited primarily to neutral (i.e., uncharged, nonionic) polymers, such as PVP, and PVP/VA, but these polymers are marginally effective in retaining a hair style or curl, impart a tacky, sticky feel to hair at conditions of relatively high humidity, and a raspy, harsh feel to dry hair. Additionally, the need for viscosity thickening or gellant additives increases the risk of leaving an unwanted residue or dull coating on the hair.

Another problem is that polymeric thickeners and polymeric hair fixatives, which are supplied in powder form, present difficult storage and handling problems during manufacturing processes, and often require complex or elaborate dispensing and processing equipment, thereby increasing manufacturing costs.

There is an ongoing need and desire, therefore, for a rheology modifying, hair setting polymer providing both thickening and hair fixative properties. It has now been surprisingly found that certain hydrophobically modified, associative polymers disclosed herein provide both hair setting efficacy and rheology modification to aqueous hair setting formulations.

SUMMARY OF THE INVENTION

The present invention discloses aqueous hair setting compositions comprising an effective rheology modifying- and hair setting amount of a rheology modifying, hair setting (RMHS) associative polymer wherein the associative polymer comprises substantially the sole hair setting agent. In particular, it has been surprisingly discovered that a hydrophobically modified, associative polymer can be employed to provide the dual function of being substantially the sole hair setting agent and rheology modifier, in aqueous hair setting compositions. Particularly preferred polymers are the polymerization products of a monomer mixture containing an acidic vinyl monomer or salt thereof and an associative monomer. The term "hair setting agent" as used herein refers to the foregoing polymerization products having hair styling and/or hair fixative properties.

Hydrophobically modified, alkali-swellable and alkali-soluble associative polymers comprising the foregoing polymerization product suitable for use in this invention are water-swellable or water-soluble and include: (i) associative polymers referred to herein as ASAP, and (ii) polymers selected from the class commonly referred to as HASE polymers. It has been surprisingly discovered that the foregoing ASAP and HASE polymers are suitable for use as the sole (i.e., active or principal) hair setting agent in aqueous hair setting compositions while concurrently providing rheology modification, such as thickening, gelation, or foam stabilization to the aqueous medium.

Aqueous hair setting compositions of this invention can contain, on a total composition weight basis, an effective amount of rheology modifying, hair setting (RMHS) polymer, calculated on an active polymer weight percent basis, preferably of greater than about 0.1%, more preferably greater than about 0.3%. The RMHS polymers were found to provide a broad range of Brookfield viscosities ranging from pourable liquids, suitable for rinses, sprays, spritzes, and the like, to non-runny gels, and non-flowable viscous compositions, suitable as squeezable gels, emulsions (e.g., in cream, paste, and liquid form), pressurized sprays, foams, mousses, pomades, and the like. The aqueous hair setting compositions can have a pH in the range of about 2.5 to above pH 12, more preferably in the range of about pH 5 to about pH 7.5. Aqueous hair setting compositions containing RMHS polymers imparted good to excellent high humidity curl resistance (HHCR). Surprisingly, good to excellent hair setting efficacy was achieved based on a demonstrated HHCR of at least about 70% curl retention at about 90% relative humidity (RH) over periods in the range of at least about 0.75 hours to as long as about 3 hours or more, particularly with ASAP hair setting agents.

Particularly preferred rheology modifying, hair setting polymers are alkali-swellable and alkali-soluble associative polymers (ASAP) which are the polymerization product of a monomer mixture comprising (a) at least one acidic vinyl monomer; (b) at least one nonionic vinyl monomer; (c) a first associative monomer having a first hydrophobic end group; (d) at least one monomer selected from the group consisting of a second associative monomer having a second hydrophobic end, a semihydrophobic monomer and a combination thereof; and, optionally, (e) one or more crosslinking monomers or chain transfer agents. When monomer (d) is an associative monomer, the first and second hydrophobic end groups of monomers (c) and (d) preferably have significantly different hydrophobic and/or steric character from one another.

The ASAP rheology modifying, hair setting polymers of this invention, in addition to concurrently providing rheology modification, provide clarity to gel products, provide a surprisingly long lasting, cosmetic hair style retention, remain non-tacky under high humidity conditions, leave no unwanted flaking residue on the hair, provide control of static fly away on hair, impart luster, body, and a natural feel to the hair, and are removable from the hair as by washing with shampoo.

It was surprisingly found that alkali-swellable ASAP can be used in combination with anionic polymeric thickener, such as carbomer polymer or hydrophobically modified carbomer polymer, to provide a viscosity that is unexpectedly higher than the sum of the viscosity of the individual polymers at the same concentration.

The present invention also embodies methods of setting hair with the RMHS polymers applied to the hair employing various product forms, or employing hair setting aids containing the RMHS polymer impregnated therein or coated thereon.

In one preferred hair setting aspect, the RMHS polymers can be provided in a kit form comprising, in a first container, an effective hair setting amount of RMHS polymer, and, optionally, in a second container, an effective pH adjusting amount of pH adjusting agent to provide an aqueous hair setting composition when the contents of the two containers are admixed in an aqueous medium. The present invention also embodies methods of setting hair with the RMHS polymer employing the kit embodiments.

Beneficially, hair setting efficacy can be obtained with the aqueous hair setting compositions of this invention by employing the rheology modifying, hair setting polymers as substantially the sole, principal hair setting agent without requiring additional gellants, thickeners or foam stabilizers. Further, the aqueous hair setting compositions were easy to prepare for use and provided product characteristics that were aesthetically and cosmetically acceptable. Another benefit is that the rheology modifying, hair setting polymers can be manufactured and provided in a liquid form, which is easy to disperse and handle during processing, thereby resulting in savings in manufacturing time and formulation costs.

DESCRIPTION OF THE PREFERRED EMBODIMENTS

The term "hair setting" as used herein refers to styling or fixing hair into a desired configuration, such as imparting a temporary curl or set (straight or curly) to human hair and retaining or maintaining (grooming, restyling) a desired set or curl configuration. The term "aqueous" means that sufficient water is present in the formulation or medium to at least swell or dissolve a rheology modifying, hair setting (RMHS) polymer included therein. The term "hair setting composition", encompasses products comprising at least one RMHS polymer as a hair setting agent that are applied to the hair (wet or dry) before, during or after configuring the hair into the shape (curly or straight) desired, without limitation as to product form. The terms "hair styling and hair fixative" as commonly understood in the hair care arts, and as used herein, refer collectively to hair setting agents that are hair fixatives and film formers and which are topically applied to the hair to actively contribute to the ease of styling and/or holding of a hair set, and to maintain the restylability of the hair set. Hence, the present hair setting compositions can include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, mousses, foams, shampoos, solids, such as sticks, semisolids and the like, or are applied from a hair setting aid having the hair setting composition impregnated therein or coated thereon, to leave the hair setting agent in contact on the hair for some period until removed, as by washing.

In one hair setting aspect, the efficacy of a hair setting composition is judged herein by its ability to provide high humidity curl resistance or retention (HHCR) to the hair. HHCR refers to the resistance of a hair set to relaxation (i.e., reversion to its original configuration) or loss of curl when exposed to a high humidity in the range of about 90% relative humidity, measured in terms of % curl retention (CR) over selected time intervals as described in more detail herein. In another aspect, hair setting efficacy is judged by the subjective properties of the hair setting composition, such as its clarity, ease of spreadability and sensory characteristics during use, and the appearance of the resulting hair set as described in more detail herein.

The term "rheology modifying" as used herein in reference to polymers refers to the property of the polymer to change the theological properties of a composition (e.g. solution viscosity, gelation, viscosity changes under shear stress, foam stabilization, gel pick-up, and the like) in which the polymer is present.

The terms, "rheology-modifying, hair setting polymer" and "RMHS polymer", as used interchangeably herein in either the singular or plural form, refer to hydrophobically modified, alkali-swellable and alkali soluble associative polymers that provide the dual function of providing hair setting efficacy and concurrently modifying the rheological and/or aesthetic properties of a water-based or hydro-alcoholic medium. The term "aesthetic property", and grammatical variations thereof, as applied to hair setting compositions refers to visual and tactile psychosensory product properties, such as color, clarity, smoothness, tack, lubricity, texture, and the like. Suitable rheology-modifying, hair setting polymers are hydrophobically modified associative polymers comprising the polymerization product of a monomer mixture comprising: (a) an acidic vinyl monomer or salt thereof; and (b) an associative monomer. Particularly preferred hydrophobically modified associative polymers include water-swellable or water-soluble, associative polymers referred to herein as (i) ASAP as described in detail below, and (ii) polymers selected from the class commonly referred to as HASE polymers.

As used herein, the term ASAP includes the singular or plural form and refers to acidic/anionic alkali-swellable and alkali-soluble associative polymers, and salts thereof, which contain two or more non-identical fatty hydrophobically modified polyoxyethylene groups derived from associative monomers, or which contain at least one hydrophobically modified polyoxyalkylene group derived from an associative monomer and at least one non-hydrophobically modified polyoxyalkylene group derived from a semihydrophobic monomer. The ASAP may also optionally contain other monomer units, such as crosslinking monomer units, or chain transfer agent units.

It has been surprisingly discovered that the hydrophobically modified ASAP and HASE polymers disclosed herein, individually, are suitable as the sole hair setting agents and for concurrently providing or attenuating rheology modification while retaining and enhancing the desired performance and aesthetic properties of the rheology modifying, hair setting (RMHS) polymer containing products. Surprisingly, the alkali-swellable ASAP hair setting polymers were found to be more efficient thickeners than conventional HASE polymers and also provided sustained hair setting efficacy at high humidity. If desired;-a combination-of ASAP and-HASE polymers can be employed. The alkali-soluble ASAP polymers are particularly useful for their low viscosity, sprayability and foam stabilization properties.

The RMHS polymers useful in the present invention are associative polymers derived from at least one acidic vinyl monomer and at least one associative monomer. The associative monomer component as defined and used herein comprises three interconnected segments: a polymerizable unsaturated end group, a hydrophobic end group, and a polyoxyalkylene segment connecting the two end groups. In preferred embodiments, the RMHS polymers are prepared from a monomer mixture containing the acidic vinyl monomer, the associative monomer, and other monomers, such as nonionic vinyl monomers, crosslinking monomers, semihydrophobic monomers and chain transfer agents.

A preferred RMHS polymer of the present invention is an ASAP, which is prepared by polymerizing a monomer mixture containing: (a) at least one acidic vinyl monomer or salt thereof; (b) at least one nonionic vinyl monomer; (c) a first associative monomer having a first hydrophobic end group; (d) at least one monomer selected from the group consisting of a second associative monomer having a second hydrophobic end group, a semihydrophobic monomer, and a combination thereof; and, optionally (e) one or more crosslinking monomers or chain transfer agents. When monomer (d) is a second associative monomer having a second hydrophobic end group, the first and second hydrophobic end groups of monomers (c) and (d) are each independently selected from the same or different hydrocarbon classes, with the proviso that when the first and second hydrophobic end groups are chosen from the same hydrocarbon class, the molecular formulas of the two hydrophobic end groups preferably differ from one another by at least about 8 carbon atoms. When monomers (c) and (d) comprise two or more associative monomers, the weight ratio of at least two of the associative monomers to one another in the monomer mixture preferably is in the range of about 1:1 to about 100:1, more preferably 1:1 to about 20:1, most preferably 1:1 to about 10:1.

In a preferred embodiment, the ASAP is the polymerization product of a monomer mixture comprising, on a total monomer mixture weight basis: (a) about 10 to about 75 weight percent of at least one acidic vinyl monomer or a salt thereof; (b) about 10 to about 90 weight percent of at least one nonionic vinyl monomer; (c) about 0.1 to about 25 weight percent of a first associative monomer having a first hydrophobic end group; (d) about 0.1 to about 25 weight percent of at least one monomer selected from the group consisting of a second associative monomer having a second hydrophobic end group, a semihydrophobic monomer and a combination thereof; and, optionally, (e) about 0.01 to about 20 weight percent of one or more monomers selected from the group consisting of a crosslinking monomer, a chain transfer agent, and a combination thereof.

Preferably, the hydrophobic end groups of the associative monomers utilized in the ASAP hair setting agents of the present invention are selected from the group consisting of a $C_8$–$C_{40}$ linear alkyl, a $C_8$–$C_{40}$ branched alkyl, a $C_8$–$C_{40}$ carbocyclic alkyl, an aryl-substituted $C_2$–$C_{40}$ alkyl, a $C_2$–$C_{40}$ alkyl-substituted phenyl, and a $C_8$–$C_{80}$ complex ester. The first and second hydrophobic end groups of the associative monomers (c) and (d) can be selected from the same or different hydrocarbon classes. However, when monomer (d) is a second associative monomer, and both the first and second associative monomers have hydrophobic end groups belonging to the same hydrocarbon class (e.g., both hydrophobic end groups are $C_8$–$C_{40}$ linear alkyl groups) then, the molecular formulas of the hydrophobic end groups are selected to differ from each other preferably by at least about 12 carbon atoms, more preferably by at least about 10 carbon atoms, and most preferably by at least about 8 carbon atoms.

A particularly preferred RMHS polymer useful in the compositions of the present invention is an alkali-swellable ASAP, which is the product of polymerization of a monomer mixture comprising, on a total monomer mixture weight basis: (a) about 30 to about 75 weight percent of at least one acidic vinyl monomer or a salt thereof; (b) at least about 25 weight percent, but not more than 60 weight percent of at least one nonionic vinyl monomer; (c) about 0.5 to about 20 weight percent of a first associative monomer having a first hydrophobic end group; (d) about 0.5 to about 20 weight percent of at least one monomer selected from the group consisting of a second associative monomer having a second hydrophobic end group, a semihydrophobic monomer, and a combination thereof; and, optionally, (e) up to about 20 weight percent of a crosslinking monomer. When monomer (d) is a second associative monomer, the first and second hydrophobic end groups of associative monomers (c) and (d) are each independently selected from the same or different hydrocarbon classes. When the first and second hydrophobic end groups are selected from the same hydrocarbon class, the molecular formulas of the hydrophobic end groups differ by at least about 8 carbon atoms. The associative polymers of this preferred embodiment are alkali-swellable and provide excellent rheology modifying characteristics, providing relatively high viscosity to alkaline aqueous systems in which the polymer is present. Examples of these preferred alkali-swellable polymers are provided in Tables 4A–4C, below.

In a particularly preferred alkali-swellable ASAP embodiment, at least one of associative monomers (c) or (d) has a hydrophobic end group which is a $C_8$–$C_{40}$ linear alkyl group, more preferably a $C_{12}$–$C_{40}$ linear alkyl group. When more than two associative monomers are utilized to prepare the ASAP of the present invention, preferably at least two of the associative monomers have hydrophobic end groups selected from different hydrocarbon classes. When more than two associative monomers are utilized to prepare the ASAP of the present invention, and all of the utilized associative monomers have hydrophobic end groups selected from the same hydrocarbon class, the molecular formula of the hydrophobic end group having the largest number of carbon atoms preferably has at least about 12 more carbon atoms, more preferably at least about 10 more carbon atoms, and most preferably at least about 8 more carbon atoms, than the molecular formula of the hydrophobic end group having the least number of carbon atoms.

However, when monomer (d) of the ASAP comprises a combination of a second associative monomer having a second hydrophobic end group and a semihydrophobic monomer, there is no limitation as to the molecular formulas of the first and second hydrophobic end groups. When monomer (d) is such a combination, the first and second associative monomers can comprise any combination of first and second hydrophobic end groups, without limitation as to hydrocarbon class or number of carbon atoms in molecular formulas of their respective hydrophobic end groups.

In another preferred embodiment of the present invention, the RMHS polymer is an alkali-soluble, relatively low viscosity ASAP. The alkali-soluble associative polymer of this preferred embodiment is the product of polymerization of a monomer mixture comprising, on a total monomer mixture weight basis: (a) about 10 to about 30 weight percent of at least one acidic vinyl monomer or a salt thereof; (b) more than about 60 weight percent of at least one nonionic vinyl monomer; (c) about 0.5 to about 5 weight percent of at least one associative monomer having a hydrophobic end group; (d) about 0.5 to about 5 weight percent of at least one semihydrophobic monomer having a polymerizable, unsaturated end group and a polyoxyalkylene group covalently bonded thereto; and (e) about 0.5 to about 5 weight percent of at least one chain transfer agent. The alkali-soluble associative polymers of this preferred embodiment provide good film-forming and humidity resistance properties making them suitable for compositions such as pumpable or sprayable hydro-alcoholic compositions where thin viscosity is desirable. Examples of these preferred alkali-soluble ASAP are provided in Table 4D, below.

The terms "first" and "second" as used herein in relation to ASAP associative monomers (c) and (d) and their respective hydrophobic end groups means that two or more different associative monomers are employed, and are not intended to imply any temporal relationship in the addition of the monomers to the reaction mixture, nor are the terms-intended to connote any functional difference between the monomers or hydrophobic end groups. The term "(meth) acrylate" includes, alternatively, acrylate or methacrylate.

As used herein the term "alkyl" means a substituted or unsubstituted aliphatic hydrocarbon moiety; the term "carbocyclic alkyl" means an alkyl group comprising one or more carbocyclic rings of from 3 to about 12 carbon atoms in size; and the term "aryl" means a substituted or unsubstituted phenyl or naphthyl moiety.

Modifiers of the form "$C_x$–$C_y$" designate that the alkyl or carbocyclic alkyl groups have molecular formulas containing a total of x to y carbon atoms, where x and y are specified integers.

The terms "halogen-substituted", "hydroxy-substituted", "carboxy-substituted", "polyoxyalkylene-substituted", "alkyl-substituted", and "aryl-substituted" as used herein in reference to alkyl or aryl groups, and the like, mean that at least one hydrogen atom on an alkyl, aryl, or like group has been replaced by at least one halogen atom, hydroxyl group, carboxyl group, polyoxyalkylene group, alkyl group, or aryl group, respectively.

Suitable monomers useful in the preparation of the dual purpose RMHS polymers of the present invention are as described below.

Acidic Vinyl Monomer

Acidic vinyl monomers suitable for use in the preparation of the RMHS polymers of the present invention are acidic, polymerizable, ethylenically unsaturated monomers preferably containing at least one carboxylic acid, sulfonic acid, or phosphonic acid group to provide an acidic or anionic functional site. These acid groups can be derived from monoacids or diacids, anhydrides of carboxylic acid, monoesters of diacids, and salts thereof.

Suitable acidic vinyl carboxylic acid-containing monomers include, but are not limited to: acrylic acid, methacrylic acid, itaconic acid, citraconic acid, maleic acid, fumaric acid, crotonic acid, aconitic acid, and the like; and $C_1$–$C_{18}$ alkyl-monoesters of maleic, fumaric, itaconic, or aconitic acid, such as methyl hydrogen maleate, monoisopropyl maleate, butyl hydrogen fumarate, and the like. Anhydrides of dicarboxylic acids, such as maleic anhydride, itaconic anhydride, citraconic anhydride, and the like, can also be utilized as acidic vinyl monomers. Such anhydrides generally hydrolyze to the corresponding diacids upon prolonged exposure to water, or at elevated pH.

Suitable sulfonic acid group-containing monomers include, but are not limited to: vinyl sulfonic acid, 2-sulfoethyl methacrylate, styrene sulfonic acid, 2-acrylamido-2-methylpropane sulfonic acid (AMPS), allyloxybenzene sulfonic acid, and the like. Particularly preferred are the sodium salt of styrene sulfonic acid (SSSA) and AMPS.

Suitable phosphonic acid group-containing monomers include vinyl phosphonic acid, allyl phosphonic acid, 3-acrylamidopropyl phosphonic acid, and the like.

The foregoing monomers or salts thereof can be used as the acidic vinyl monomer component of the RMHS polymers, individually, or in mixtures of two or more. Acrylic acid, methacrylic acid, the sodium salt of styrene sulfonic acid (SSSA), as well as maleic acid, fumaric acid, itaconic acid, and monoesters or monoamides thereof, are preferred. Particularly preferred acidic vinyl monomers are acrylic acid, methacrylic acid, SSSA and AMPS.

The acidic vinyl monomer preferably comprises about 10 to about 75 weight percent of the total monomer mixture utilized to prepare the polymer, more preferably about 25 to about 65 weight percent, and most preferably about 30 to about 60 weight percent, on a total monomer mixture weight basis.

Nonionic Monomer

Nonionic vinyl monomers suitable for use in the preparation of the RMHS polymers are a copolymerizable, nonionic, ethylenically unsaturated monomers having either of the following formulas (I) or (II):

$$CH_2\!=\!C(X)Z \qquad (I)$$

$$CH_2\!=\!CH\!-\!OC(O)R \qquad (II)$$

wherein, in each of formulas (I) and (II), X is H or methyl; Z is —C(O)OR$^1$, —C(O)NH$_2$, —C(O)NHR$^1$, —C(O)N-(R$^1$)$_2$, —C$_6$H$_4$R$^1$, —C$_6$H$_4$OR$^1$, —C$_6$H$_4$Cl, —CN, —NHC(O)CH$_3$, —NHC(O)H, N-(2-pyrrolidonyl), N-caprolactamyl, —C(O)NHC(CH$_3$)$_3$, —C(O)NHCH$_2$CH$_2$—N-ethyleneurea, —SiR$_3$, —C(O)O(CH$_2$)$_x$SiR$_3$, —C(O)NH(CH$_2$)$_x$SiR$_3$, or —(CH$_2$)$_x$SiR$_3$; x is an integer in the range of 1 to about 6; each R is independently C$_1$–C$_{18}$ alkyl; each R$^1$ is independently C$_1$–C$_{30}$ alkyl, hydroxy-substituted C$_2$–C$_{30}$ alkyl, or halogen-substituted C$_1$–C$_{30}$ alkyl.

Non-limiting examples of suitable water-insoluble, nonionic vinyl monomers include C$_1$–C$_{30}$ alkyl(meth)acrylates; C$_1$–C$_{30}$ alkyl(meth)acrylamides; styrene; substituted styrenes, such as vinyl toluene, butyl styrene, isopropyl styrene, p-chloro styrene, and the like; vinyl esters, such as vinyl acetate, vinyl butyrate, vinyl caprolate, vinyl pivalate, vinyl neodecanoate, and the like; unsaturated nitriles, such as methacrylonitrile, acrylonitrile and the like; and unsaturated silanes, such as trimethylvinylsilane, dimethylethylvinylsilane, allyldimethylphenylsilane, allytrimethylsilane, 3-acrylamidopropyltrimethylsilane, 3-trimethylsilylpropyl methacrylate, and the like.

Non-limiting examples of suitable water-soluble nonionic vinyl monomers are C$_2$–C$_6$ hydroxyalkyl(meth)acrylates; glycerol mono(meth)acrylate; tris(hydroxymethyl)ethane mono(meth)acrylate; pentaerythritol mono(meth)acrylate; N-hydroxymethyl(meth)acrylamide; 2-hydroxyethyl(meth) acrylamide; 3-hydroxypropyl(meth)acrylamide; (meth)acrylamide; N-vinyl caprolactam; N-vinyl pyrrolidone; methacrylamidoethyl-N-ethyleneurea (e.g., CH$_2$=C(CH$_3$)C(O) NHCH$_2$CH$_2$—N-ethyleneurea), C$_1$–C$_4$ alkoxy-substituted (meth)acrylates and (meth)acrylamides, such as methoxyethyl (meth)acrylate, 2-(2-ethoxyethoxy)ethyl(meth)acrylate, and the like; and combinations thereof.

Particularly preferred nonionic vinyl monomers include C$_1$–C$_8$ alkyl esters of acrylic acid and of methacrylic acid, methacrylamidoethyl-N-ethylene urea, and combinations thereof.

The nonionic vinyl monomer (b) preferably comprises about 10 to about 90 weight percent of the total monomer mixture, more preferably about 25 to about 75 weight percent, and most preferably about 30 to about 60 weight percent, on a total monomer mixture weight basis.

Associative Monomer

Associative monomers suitable for use in the production of the RMHS polymers are compounds preferably having an ethylenically unsaturated end group portion (i) for addition polymerization with the other monomers of the system; a polyoxyalkylene midsection portion (ii) for imparting selective hydrophilic properties to the product polymer and a hydrophobic end group portion (iii) for providing selective hydrophobic properties to the polymer.

The portion (i) supplying the ethylenically unsaturated end group preferably is derived from an α,β-ethylenically unsaturated mono or di-carboxylic acid or the anhydride thereof, more preferably a $C_3$ or $C_4$ mono- or di-carboxylic acid or the anhydride thereof. Alternatively, portion (i) of the associative monomer can be derived from an allyl ether or vinyl ether; a nonionic vinyl-substituted urethane monomer, such as disclosed in U.S. Reissue Pat. Nos. 33,156 or 5,294,692; or a vinyl-substituted urea reaction product, such as disclosed in U.S. Pat. No. 5,011,978; the relevant disclosures of each being incorporated herein by reference.

The midsection portion (ii) is preferably a polyoxyalkylene segment of about 5 to about 250, more preferably about 10 to about 120, and most preferably about 15 to about 60 repeating $C_2$–$C_7$ alkylene oxide units. Preferred midsection portions (ii) include polyoxyethylene, polyoxypropylene, and polyoxybutylene segments comprising about 5 to about 150, more preferably about 10 to about 100, and most preferably about 15 to about 60 ethylene, propylene or butylene oxide units, and random or non-random sequences of ethylene oxide, propylene oxide and or butylene oxide units.

The hydrophobic end group portion (iii) of the associative monomers is preferably a hydrocarbon moiety belonging to one of the following hydrocarbon classes: a $C_8$–$C_{40}$ linear alkyl, an aryl-substituted $C_2$–$C_{40}$ alkyl, a $C_2$–$C_{40}$ alkyl-substituted phenyl, a $C_8$–$C_{40}$ branched alkyl, a $C_8$–$C_{40}$ carbocyclic alkyl; and a $C_8$–$C_{80}$ complex ester.

As used herein and in the appended claims, the term "complex ester" means a di-, tri-, or poly-ester of a polyol such as a sugar, having at least one hydroxyl group capable of being alkylated with a $C_2$–$C_7$ alkylene oxide. The term "complex ester" includes, in particular, the complex hydrophobes described by Jenkins et al. in U.S. Pat. No. 5,639,841, the relevant disclosure of which is incorporated herein by reference.

Non-limiting examples of suitable hydrophobic end group portions (iii) of the associative monomers are linear or branched alkyl groups having about 8 to about 40 carbon atoms, such as capryl ($C_8$), isooctyl (branched $C_8$), decyl ($C_{10}$), lauryl ($C_{12}$), myristyl ($C_{14}$), cetyl ($C_{16}$), cetearyl ($C_{16}$–$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), lacceryl ($C_{32}$), and the like.

Examples of linear and branched alkyl groups having about 8 to about 40 carbon atoms that are derived from a natural source include, without being limited thereto, alkyl groups derived from hydrogenated peanut oil, soybean oil and canola oil (all predominately $C_{18}$), hydrogenated tallow oil ($C_{16}$–$C_{18}$), and the like; and hydrogenated $C_{10}$–$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$–$C_{40}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Suitable $C_8$–$C_{40}$ carbocylic alkyl groups-include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials, such as pinene, hydrogenated retinol, camphor, isobornyl alcohol, and the like.

Exemplary aryl-substituted $C_2$–$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non-limiting examples of suitable $C_8$–$C_{80}$ complex esters include hydrogenated castor oil (predominately the triglyceride of 12-hydroxystearic acid); 1,2-diacyl glycerols, such as 1,2-distearyl glycerol, 1,2-dipalmityl glycerol, 1,2-dimyristyl glycerol, and the like; di-, tri-, or poly-esters of sugars, such as 3,4,6-tristearyl glucose, 2,3-dilauryl fructose, and the like; and sorbitan esters, such as those disclosed in U.S. Pat. No. 4,600,761 to Ruffner et al., the pertinent disclosures of which are incorporated herein by reference.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

Examples of preferred associative monomers include those having formula (III).

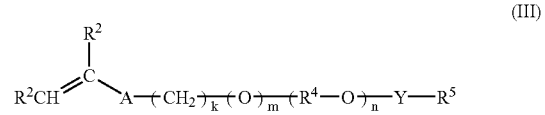

(III)

wherein, each $R^2$ is independently H, methyl, —C(O)OH, or —C(O)OR$^3$; $R^3$ is $C_1$–$C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; ($R^4$—O)$_n$ is a polyoxyalkylene, which is a homopolymer, a random copolymer or a block copolymer of $C_2$–$C_4$ oxyalkylene units, wherein $R^4$ is $C_2H_4$, $C_3H_6$, or $C_4H_8$, and n is an integer in the range of about 5 to about 250, preferably about 5 to about 100, more preferably about 10 to about 80, and most preferably about 15 to about 60; Y is —R$^4$O—, —R$^4$NH—, —C(O)—, —C(O)NH—, —R$^4$NHC(O)NH—, or —C(O)NHC(O)—; $R^5$ is a substituted or unsubstituted alkyl selected from the group consisting of a $C_8$–$C_{40}$ linear alkyl, a $C_8$–$C_{40}$ branched alkyl, a $C_8$–$C_{40}$ carbocyclic alkyl, a $C_2$–$C_{40}$ alkyl-substituted phenyl, an aryl-substituted $C_2$–$C_{40}$ alkyl, and a $C_8$–$C_{80}$ complex ester; wherein the $R^5$ alkyl group optionally comprises one or more substituents selected from the group consisting of a hydroxyl group, an alkoxyl group, and a halogen group.

Particularly preferred associative monomers of formula (III) include cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), cerotyl polyethoxylated (meth)acrylate, montanyl polyethoxylated (meth)acrylate, melissyl polyethoxylated (meth)acrylate, lacceryl polyethoxylated (meth)acrylate, tristyrylphenol polyethoxylated methacrylate (TEM), hydrogenated castor oil polyethoxylated methacrylate (HCOEM), canola polyethoxylated (meth)acrylate, and cholesterol polyethoxylated methacrylate (CHEM), where the polyethoxylated portion of the monomer comprises about 5 to about 100, preferably about 10 to about 80, and more preferably about 15 to about 60 ethylene oxide repeating units.

Preferably, the associative monomer components in the monomer mixture independently comprise, on a total monomer mixture weight basis, about 0.1 to about 25 weight percent of the monomer mixture, more preferably about 0.25 to about 20 weight percent, most preferably about 0.5 to about 15 weight percent.

Semihydrophobic Monomer

It was surprisingly found that a semihydrophobic monomer (SH monomer) can moderate the associative properties of polymers containing them, thus producing aqueous gels with highly desirable texture and theological properties. Not wishing to be bound by theory, it is thought that the polyoxyalkylene group of the SH monomer interrupts or shields against non-specific associations between the hydrophobic groups of the associative monomers in the polymer, or external components and thus attenuates the associative properties of the polymers. Such SH monomers can tailor the thickening efficiency and foam stabilizing properties of the resulting polymers to customize the rheological properties of the polymer as desired for a selected application. Most surprisingly, alkali-swellable ASAP containing the SH monomers were generally found to impart desirable theological, and aesthetic properties to aqueous gels, generally providing softer, smoother and more spreadable gels at all polymer concentrations than did alkali-swellable associative polymers containing no SH monomer and provided a Brookfield viscosity that remained substantially unchanged over a period of 24 hours.

Surprisingly, incorporation of a SH monomer into an alkali-swellable ASAP can reduce gel viscosity at low shear stress, minimize or eliminate viscosity reduction as shear stress is increased, and minimize or decrease shear thinning behavior of the gels. For example, Polymer CP-5, described in Example 1 below, incorporating about 3% BEM25 associative monomer, when measured by a complex viscosity technique at an active polymer weight concentration of about 1.2%, had a viscosity of 178 Pa·s at a shear stress of 1 Pa; and increasing the shear stress to 5 Pa led to a reduction in complex viscosity to 43.6 Pa·s. Adding a SH monomer to the polymer, e.g. as in Polymer AG, Example 1, which contains 3% BEM25 associative monomer and 5% of the SH monomer R307, had two effects. First, the complex viscosity measured at an active polymer concentration of about 1.2% at 1 Pa shear stress was reduced to 106 Pa·s. Second, upon increasing the shear stress to 5 Pa, the complex viscosity measurement remained almost unchanged (105.5 Pa·s).

Similarly, when 15% of SH monomer was incorporated (e.g., as in Polymer AI, Example 1), the complex viscosity measured at an active polymer concentration of about 1.2% at 1 Pa shear stress was 46.5 Pa·s, whereas the complex viscosity measured at 5 Pa shear stress was 36 Pa·s.

As used herein and in the appended claims, the terms "semihydrophobic monomer" and "SH monomers" refer to compounds having two portions: (i) an ethylenically unsaturated end group portion for addition polymerization with the other monomers of the reaction mixture, and (ii) a polyoxyalkylene portion for attenuating the associations between the hydrophobic groups of the polymer or hydrophobic groups from other materials in a composition containing the polymer. A SH monomer is similar to an associative monomer, but has a substantially non-hydrophobic end group and does not impart associative properties to polymers in which it is incorporated.

The unsaturated end group portion (i) supplying the vinyl or other ethylenically unsaturated end group for addition polymerization is preferably derived from an α,β-ethylenically unsaturated mono or di-carboxylic acid or the anhydride thereof, preferably a $C_3$ or $C_4$ mono- or di-carboxylic acid, or the anhydride thereof. Alternatively, the end group portion (i) can be derived from an allyl ether, vinyl ether or a nonionic urethane monomer.

The polymerizable unsaturated end group portion (i) can also be derived from a $C_8$–$C_{30}$ unsaturated fatty acid group containing at least one free carboxy-functional group. This $C_8$–$C_{30}$ group is part of the unsaturated end group portion (i) and is different from the hydrophobic groups pendant to the associative monomers, which are specifically separated from the unsaturated end group of the associative monomer by a hydrophilic "spacer" portion.

The polyoxyalkylene portion (ii) specifically comprises a long-chain polyoxyalkylene segment, which is substantially similar to the hydrophilic portion of the associative monomer. Preferred polyoxyalkylene portions (ii) include polyoxyethylene, polyoxypropylene, and polyoxybutylene units comprising about 2 to about 250, and preferably about 10 to about 100 ethylene oxide, propylene oxide, or butylene oxide units, or random or non-random sequences of ethylene oxide, propylene oxide, and/or butylene oxide units.

Preferred SH monomers include those having either of the following formulas (IV) or (V):

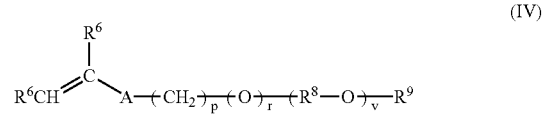

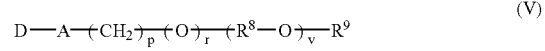

wherein, in each of formulas (IV) and (V), each $R^6$ is independently H, $C_1$–$C_{30}$ alkyl, —C(O)OH, or —C(O)O$R^7$; $R^7$ is $C_1$–$C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; p is an integer in the range of 0 to about 30, and r is 0 or 1, with the proviso that when p is 0, r is 0, and when p is in the range of 1 to about 30, r is 1; ($R^8$—O)$_v$ is a polyoxyalkylene, which is a homopolymer, a random copolymer or a block copolymer of $C_2$–$C_4$ oxyalkylene units, wherein $R^8$ is $C_2H_4$, $C_3H_6$, or $C_4H_8$, and v is an integer in the range of about 5 to about 250, preferably about 5 to about 100, more preferably about 10 to about 80, and most preferably about 15 to about 60; $R^9$ is H or $C_1$–$C_4$ alkyl; and D is a $C_8$–$C_{30}$ unsaturated alkyl or a carboxy-substituted $C_8$–$C_{30}$ unsaturated alkyl.

Particularly preferred semihydrophobic monomers include monomers having the following chemical formulas:

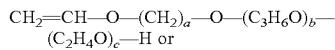

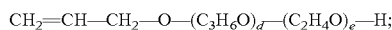

wherein a, preferably, is 2, 3, or 4; b, preferably, is an integer in the range of 1 to about 10, more preferably about 2 to about 8, most preferably about 3 to about 7; c, preferably, is an integer in the range of about 5 to about 50, more preferably about 8 to about 40, most preferably about 10 to about 30; d, preferably, is an integer in the range of 1 to about 10, more preferably about 2 to about 8, most preferably about 3 to about 7; and e, preferably, is an integer in the range of about 5 to about 50, more preferably about 8 to about 40.

Examples of preferred SH monomers include polymerizable emulsifiers commercially available under the trade names EMULSOGEN® R109, R208, R307, RAL109, RAL208, and RAL307 sold by Clariant Corporation; BX-AA-E5P5 sold by Bimax, Inc.; and MAXEMUL® 5010 and 5011 sold by Uniqema. Particularly preferred SH monomers include EMULSOGEN® R109, R208, and R307, BX-AA-E5P5, MAXEMUL® 5010 and 5011, and combinations thereof.

According to the manufacturers:

EMULSOGEN® R109 is a randomly ethoxylated/propoxylated 1,4-butanediol vinyl ether having the empirical formula $CH_2=CH-O(CH_2)_4O(C_3H_6O)_4(C_2H_4O)_{10}H$; EMULSOGEN® R208 is a randomly ethoxylated/propoxylated 1,4-butanediol vinyl ether having the empirical formula $CH_2=CH-O(CH_2)_4O(C_3H_6O)_4(C_2H_4O)_{20}H$; EMULSOGEN® R307 is a randomly ethoxylated/propoxylated 1,4-butanediol vinyl ether having the empirical formula $CH_2=CH-O(CH_2)_4O(C_3H_6O)_4(C_2H_4O)_{30}H$; EMULSOGEN® RAL109 is a randomly ethoxylated/propoxylated allyl ether having the empirical formula $CH_2=CH-CH_2O(C_3H_6O)_4(C_2H_4O)_{10}H$; EMULSOGEN® RAL208 is a randomly ethoxylated/propoxylated allyl ether having the empirical formula $CH_2=CH-CH_2O(C_3H_6O)_4(C_2H_4O)_{20}H$; EMULSOGEN® RAL307 is a randomly ethoxylated/propoxylated allyl ether having the empirical formula $CH_2=CH-CH_2O(C_3H_6O)_4(C_2H_4O)_{30}H$; MAXEMUL® 5010 is a carboxy-functional $C_{12}$–$C_{15}$ alkenyl hydrophobe, ethoxylated with about 24 ethylene oxide units; MAXEMUL® 5011 is a carboxy-functional $C_{12}$–$C_{15}$ alkenyl hydrophobe, ethoxylated with about 34 ethylene oxide units; and BX-AA-E5P5 is a randomly ethoxylated/propoxylated allyl ether having the empirical formula $CH_2=CH-CH_2O(C_3H_6O)_5(C_2H_4O)_5H$.

The amount of semihydrophobic monomers utilized in the preparation of the RMHS polymer can vary widely and depends, among other things, on the final rheological and aesthetic properties desired in the polymer. When utilized, the monomer reaction mixture preferably contains one or more semihydrophobic monomers in amounts in the range of about 0.1 to about 25 weight percent based on the total monomer mixture weight, more preferably about 0.5 to about 20 weight percent, most preferably about 1 to about 15 weight percent.

Crosslinking Monomer

The RMHS polymers can optionally be prepared from a monomer mixture comprising one or more crosslinking monomer (e) for introducing branching and controlling molecular weight. Suitable polyunsaturated crosslinkers are well known in the art. Mono-unsaturated compounds carrying a reactive group that is capable of causing a formed copolymer to be crosslinked before, during, or after polymerization has taken place can also be utilized. Other useful crosslinking monomers include polyfunctional monomers containing multiple-reactive groups, such as epoxide groups, isocyanate groups, and hydrolyzable silane groups. Various polyunsaturated compounds can be utilized to generate either a partially or substantially cross-linked three dimensional network.

Examples of suitable polyunsaturated crosslinking monomer components include, without being limited thereto, polyunsaturated aromatic monomers, such as divinylbenzene, divinyl naphthalene, and trivinylbenzene; polyunsaturated alicyclic monomers, such as 1,2,4-trivinylcyclohexane; di-functional esters of phthalic acid, such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers include polyalkenyl ethers, such as triallyl pentaerythritol, diallyl pentaerythritol, diallyl sucrose, octaallyl sucrose, and trimethylolpropane diallyl ether; polyunsaturated esters of polyalcohols or polyacids, such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, triethyleneglycol di(meth)acrylate; polyunsaturated silanes, such as dimethyldivinylsilane, methyltrivinylsilane, allyldimethylvinylsilane, diallydimethylsilane and tetravinylsilane; polyunsaturated stannanes, such as tetraallyl tin, diallyldimethyl tin; and the like.

Useful monounsaturated compounds carrying a reactive group include N-methylolacrylamide; N-alkoxy(meth)acrylamide, wherein the alkoxy group is a $C_1$–$C_{18}$ alkoxy; and unsaturated hydrolyzable silanes, such as triethoxyvinylsilane; tris-isopropoxyvinylsilane, 3-triethoxysilylpropyl methacrylate, and the like.

Useful polyfunctional crosslinking monomers containing multiple reactive groups include, but are not limited to, hydrolyzable silanes, such as ethyltriethoxysilane and ethyltrimethoxysilane; epoxy substituted hydrolyzable silanes, such as 2-(3,4-epoxycyclohexyl)ethyltriethoxysilane and 3-glycidoxypropyltrimethyoxysilane; polyisocyanates, such as 1,4-diisocyanatobutane, 1,6-diisocyanatohexane, 1,4-phenylenediisocyanate, and 4,4'-oxybis(phenylisocyanate); unsaturated epoxides, such as glycidyl methacrylate and allylglycidyl ether; and polyepoxides, such as diglycidyl ether, 1,2,5,6-diepoxyhexane and ethyleneglycoldiglycidyl ether; and the like.

Particularly useful are polyunsaturated crosslinkers derived from ethoxylated polyols, such as diols, triols and bis-phenols, ethoxylated with about 2 to about 100 moles of ethylene oxide per mole of hydroxyl functional group and end-capped with a polymerizable unsaturated group, such as a vinyl ether, allyl ether, acrylate ester, methacrylate ester, and the like. Examples of such crosslinkers include bisphenol A ethoxylated dimethacrylate; bisphenol F ethoxylated dimethacrylate, trimethylol propane ethoxylated trimethacrylate, and the like. Other ethoxylated crosslinkers useful in the RMHS polymers of the present invention include ethoxylated polyol-derived crosslinkers disclosed in U.S. Pat. No. 6,140,435 to Zanotti-Russo, the pertinent disclosures of which are incorporated herein by reference.

Examples of particularly preferred crosslinkers are acrylate and methacrylate esters of polyols having at least two acrylate or methacrylate ester groups, such as trimethylolpropane triacrylate (TMPTA), trimethylolpropane dimethacrylate, polyethylene glycol dimethacrylate, ethoxylated (30) bisphenol A dimethacrylate (EOBDMA), and the like.

When utilized, crosslinking monomers are present in the monomer reaction mixture preferably in an amount in the range of about 0.01 to about 2 weight percent, based on the total monomer mixture weight, more preferably about 0.05 to about 1.5 weight percent, most preferably about 0.1 to about 1 weight percent of the monomer mixture.

Chain Transfer Agent

The RMHS polymer can optionally be prepared from a monomer mixture comprising one or more chain transfer agents, which are well known in the polymer arts.

Suitable chain transfer agents for use in this invention, without being limited thereto, are selected from a variety of thio and disulfide containing compounds, such as $C_1$–$C_{18}$ alkyl mercaptans, mercaptocarboxylic acids, mercaptocarboxylic esters, thioesters, $C_1$–$C_{18}$ alkyl disulfides, aryldisulfides, polyfunctional thiols, and the like; phosphites and hypophosphites; haloalkyl compounds, such as carbon tetrachloride, bromotrichloromethane, and the like; and unsaturated chain transfer agents, such as alpha-methylstyrene.

Polyfunctional thiols include trifunctional thiols, such as trimethylolpropane-tris-(3-mercaptopropionate), tetrafunctional thiols, such as pentaerythritol-tetra-(3-mercaptopropionate), pentaerythritol-tetra-(thioglycolate), and pentaerythritol-tetra-(thiolactate); hexafunctional thiols, such as dipentaerythritol-hexa-(thioglycolate); and the like.

Alternatively, the chain transfer agent can be any catalytic chain transfer agent which reduces molecular weight of addition polymers during free radical polymerization of vinyl monomers. Examples of catalytic chain transfer agents include, for example, cobalt complexes (e.g., cobalt (II) chelates). Catalytic chain transfer agents can often be utilized in relatively low concentrations relative to thiol-based CTAs.

Examples of preferred chain transfer agents include octyl mercaptan, n-dodecyl mercaptan (DDM), t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, dodecyl thioglycolate, and the like. The chain transfer agents can be added to a monomer reaction mixture preferably in amounts of up to about 10 weight percent of polymerizable monomer mixture, based on total monomer mixture weight.

The ASAP and HASE polymers useful in the compositions of the present invention can be manufactured by conventional polymerization techniques, such as emulsion polymerization, as is known in the polymer art. Typically the polymerization process is carried out at a reaction temperature in the range of about 30 to about 95° C., however, higher or lower temperatures can be used. To facilitate emulsification of the monomer mixture, the emulsion polymerization can be carried out in the presence of anionic surfactants, such as fatty alcohol sulfates or alkyl sulfonates, nonionic surfactants, such as linear or branched alcohol ethoxylates, amphoteric surfactants, or mixtures thereof. The emulsion polymerization reaction mixture also includes one or more free radical initiators, preferably in an amount in the range of about 0.01 to about 3 weight percent based on total monomer weight. The polymerization can be performed in an aqueous or aqueous alcohol medium at a low pH, i.e., preferably not more than about pH 4.5.

Anionic surfactants suitable for facilitating emulsion polymerizations are well known in the polymer art, and include sodium lauryl sulfate, sodium dodecyl benzene sulfonate, sodium dioctyl sulfosuccinate, sodium di-sec-butyl naphthalene sulfonate, disodium dodecyl diphenyl ether sulfonate, disodium laureth-3 sulfosuccinate, disodium n-octadecyl sulfosuccinate, phosphate esters of branched alcohol ethoxylates, and the like.

Exemplary free radical initiators include, without being limited thereto, the water-soluble inorganic persulfate compounds, such as ammonium persulfate, potassium persulfate, and sodium persulfate; peroxides, such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid and perbenzoic acid (optionally activated with reducing agents, such as sodium bisulfite or ascorbic acid); and oil soluble, free radical producing agents, such as 2,2'-azobisisobutyronitrile, and the like. Particularly suitable free-radical polymerization initiators include water soluble azo polymerization initiators, such as 2,2'-azobis(tert-alkyl) compounds having a water solubilizing substituent on the alkyl group. Preferred azo polymerization catalysts include the VAZO® free-radical polymerization initiators, available from DuPont, such as VAZO® 44 (2,2'-azobis(2-(4,5-dihydroimidazolyl)propane), VAZO® 56 (2,2'-azobis(2-methylpropionamidine)dihydrochloride), and VAZO® 68 (4,4'-azobis(4-cyanovaleric acid)).

Optionally, other emulsion polymerization additives, which are well known in the emulsion polymerization art, such as buffering agents, chelating agents, inorganic electrolytes, chain terminators, and pH adjusting agents can be included in the polymerization system.

A preferred general emulsion polymerization procedure that can be employed for the preparation of ASAP and HASE polymers, is provided below:

A monomer emulsion is prepared in a first reactor equipped with a nitrogen inlet and an agitator, by combining a desired amount of each of monomer in water containing an emulsifying amount of an anionic surfactant under a nitrogen atmosphere and with mixing agitation. To a second reactor equipped with an agitator, nitrogen inlet and feed pumps, are added a desired amount of water and additional anionic surfactant, if desired, under a nitrogen atmosphere, and the contents of the second reactor are heated with mixing agitation. After the contents of the second reactor reach a temperature in the range of about 65–98° C., a free radical initiator is injected into the so-formed aqueous surfactant solution in the second reactor, and the monomer emulsion from the first reactor is then gradually pumped into the second reactor over a period typically in the range of about one to about four hours at a controlled reaction temperature in the range of about 65–95° C. After completion of the monomer addition, an additional quantity of free radical initiator can be added to the second reactor, if desired, and the resulting reaction mixture is typically held at a temperature of about 75–95° C. for a time period sufficient to complete the polymerization reaction. The resulting polymer emulsion can then be cooled and discharged from the reactor.

One skilled in the polymer arts will recognize that the amounts of each monomer component can be adjusted to obtain polymers having any desired type and ratio of monomers. Larger or smaller proportions of water may also be utilized, as desired. Water miscible solvents, such as alcohols, and other polymerization additives, as described above, may also be included in the reaction mixture. Non-ionic surfactants, such as linear or branched alcohol ethoxylates, can also be added as is known in the emulsion polymerization art.

The product polymer emulsions can be prepared to preferably contain about 1 percent to about 60 percent total polymer solids, more preferably about 10 percent to about 50 percent total polymer solids, most preferably about 15 percent to about 45 percent total polymer solids (TS) based on the weight of the polymer. Prior to any neutralization, the polymer emulsions, as produced, typically have a pH in the range of about 2 to not more than about 5.5, a Brookfield viscosity of not more than about 100 milli-Pascal seconds (mPa·s) at ambient room temperature (spindle #2, 20 rpm) and a glass transition temperature (Tg) of not more than about 150° C. as determined by Method C below.

Optionally, the produced polymer emulsions can be further processed by adjustment of pH to a value preferably in the range of above about 3 to about 7.5 or adjusted to greater than about pH 12, with alkaline materials, preferably alkali metal hydroxides, organic bases, and the like. The inventive alkali-swellable associative polymer emulsions typically swell to a viscosity greater than about 100 mPa·s and form viscous solutions or gels at neutral to alkaline pH, and the polymers are generally substantially stable at such pH values, even at pH values greater than about 12. The alkali-soluble associative polymers generally maintain a thin viscosity at alkaline pH. The polymer emulsions can also be diluted with water or solvent, or concentrated by evaporation of a portion of the water. Alternatively, the obtained polymer emulsion may be substantially dried to a powder or crystalline form by utilizing equipment well known in the art, such as, for example, a spray drier, a drum drier, or a freeze drier.

The RMHS polymers can be prepared by emulsion polymerization and utilized by incorporating various known additives and conventional adjuvants, and solvents other than water, into the RMHS polymer emulsion product, as needed, to achieve the intended form for use of the final composition without altering or adversely affecting the performance or properties of the polymer. Alternatively, the RMHS polymers can be incorporated as an ingredient into a formulation, preferably in a liquid form, employing conventional mixing equipment.

Examples of some commercially available preferred HASE polymers, which have been surprisingly found suitable as RMHS polymers include, without being limited thereto, polymeric thickeners sold under the trade names, SALCARE® SC 80 by Ciba Specialty Chemicals Corp.; STRUCTURE® 2001 and STRUCTURE® 3001, by National Starch and Chemical Company; SYNTHALEN® W2000, by 3V Inc., and ACULYN® 22 and ACULYN® 28, by ISP, Inc.

SALCARE® SC80 is described in U.S. Pat. No. 6,074,439 to De La Mettrie, et al. as a copolymer of about 40 weight percent methacrylic acid (MAA), about 50 weight percent ethyl acrylate (EA) and about 10 weight percent steareth-10 allyl ether (associative monomer).

STRUCTURE® 2001 is described by the manufacturer as a copolymer of acrylic acid, acrylate esters and steareth-20 itaconate (associative monomer). STRUCTURE® 3001 is described by the manufacturer as a copolymer of acrylic acid, acrylate esters and ceteth-20 itaconate (associative monomer).

ACULYN® 28 is described by the manufacturer as a copolymer of acrylic acid, methacrylic acid, acrylate esters and beheneth-25 methacrylate (associative monomer). ACULYN® 22 is described by the manufacturer as a copolymer of an acrylic acid, methacrylic acid, acrylate ester, and steareth-20 methacrylate (associative monomer).

SYNTHALEN® W2000 is described by the manufacturer as a copolymer of acrylates and palmeth-25 acrylate (associative monomer).

The foregoing commercial HASE polymers have the physical properties shown in Table 1:

TABLE 1

| Polymer | Acid Value** | Wt. % Acid Monomer | % TS* | pH* | Tg |
|---|---|---|---|---|---|
| SALCARE® SC 80 | 242 | 37† (40‡) | 30 | 3 | 60.7 |
| STRUCTURE® 3001 | 324 | 42†† | 28–30 | 2.2–3.5 | 114.7 |
| STRUCTURE® 2001 | 285 | 37†† | 28–30 | 2.2–3.5 | 68.7 |
| SYNTHALEN® W2000 | 301 | 46† (39††) | 30–32 | 2–3 | 83.6 |
| ACULYN® 28 | 257 | 40† (33††) | 19–21 | 2.5–3.5 | 55.4 |
| ACULYN® 22 | 267 | 41† (34††) | 29–31 | 2.5–3.5 | 74.4 |

*As supplied and reported by the manufacturer.
**Active polymer basis, calculated by titration of polymer with KOH; values in mg KOH/g active polymer.
†Estimated as methacrylic acid based on the acid value.
††Estimated as acrylic acid based on the acid value.
‡% Methacrylic acid according to U.S. Pat. No. 6,074,439.

The amount of RMHS agents employed in hair setting compositions of this invention is not limited, as the amount is determined by the type of hair setting efficacy and rheological property desired. One skilled in the formulation arts can readily select the amount of hair setting agent to provide the desired hair setting efficacy and rheological characteristic. All references to weight % RMHS polymer means active weight % polymer on a total formulation weight basis. Thus, a hair setting composition of this invention can contain, on a total composition basis, RMHS polymer in an active polymer weight amount in the range of about 0.1% to about 15%, preferably in the range of about 0.3% to about 12%, and more preferably in the range of about 0.5% to about 10%. A preferred hair setting amount of active polymer weight percent of ASAP preferably is in the range of about 0.1% to about 10%, more preferably in the range of about 0.5% to about 5%, and most preferably in the range of about 0.75% to about 3%. A preferred hair setting amount of active polymer weight percent of HASE polymer preferably is in the range of about 0.1% to about 10%, more preferably in the range of about 0.5% to about 5%, and most preferably in the range of about 0.6% to about 3%. Hair setting compositions comprising RMHS polymers preferably have a Brookfield viscosity of greater than about 100 mPa·s.

Concentrated additives, adjuvant ingredients, products or materials that can be employed with the inventive polymers discussed herein are referred to by their commonly used chemical names or by the international nomenclature commonly referred to as INCI name given them in the *Interna-*

*tional Cosmetic Ingredient Dictionary*, Volumes 1 and 2, Sixth Edition, (1995) or *International Cosmetic Ingredient Dictionary and Handbook*, Volumes 1–3, Seventh Edition (1997), both published by the Cosmetic, Toiletry, and Fragrance Association, Washington D.C. (both hereafter INCI Dictionary). Numerous commercial suppliers of materials listed by INCI name, trade name or both can be found in the INCI Dictionary and in numerous commercial trade publications, including but not limited to, the 2001 *McCutcheon's Directories*, Volume 1: Emulsifiers & Detergents and Volume 2: Functional Materials, published by McCutcheon's Division, The Manufacturing Confectioner Publishing Co. Glen Rock, N.J. (2001); and 2001 *Cosmetic Bench Reference*, edition of COSMETICS & TOILETRIES® 115 (13), published by Allured Publishing Corporation, Carol Stream, Ill. (2001), the relevant disclosures of the INCI Dictionary and each of the foregoing publications being incorporated herein by reference.

Hair setting product formulations comprising RMHS polymer can contain various additives and cosmetic adjuvants, conventionally or popularly included in hair setting compositions, as are well known in the art, including, without being limited thereto, acidifying or alkalizing pH adjusting agents and buffering agents; auxiliary hair fixatives and film formers, such as nonionic, anionic, cationic or amphoteric polymers of synthetic or natural origin, and the like; auxiliary rheology modifiers, such as viscosity-increasing polymeric, gum, or resin thickeners or gellants; additives, such as emulsifiers, emulsion stabilizers, waxes, dispersants, and the like, and viscosity control agents, such as solvents, electrolytes, and the like; hair conditioning agents, such as antistatic agents, synthetic oils, vegetable or animal oils, silicone oils, monomeric or polymeric quaternized ammonium salts, hair sheen enhancers, emollients, lubricants, sunscreen agents, and the like; chemical hair waving or straightening agents; hair colorants, such as pigments and dyes for temporary, semipermanent, or permanent colorant hair setting; surfactants, such as anionic, cationic, nonionic, amphoteric and zwitterionic surfactants; polymer film modifying agents, such as plasticizers, humectants, tackifiers, detackifiers, wetting agents, and the like, product finishing agents, such as chelating agents, opacifiers, pearlescing agents, proteinaceous materials and derivatives thereof, vitamins and derivatives thereof, preservatives, fragrances, solubilizers, colorants, such as pigments and dyes, UV absorbers, and the like; propellants (water-miscible or water-immiscible), such as fluorinated hydrocarbons, liquid volatile hydrocarbons, compressed gases, and the like; and mixtures thereof. An extensive listing of cosmetic ingredients and their functions appears in the INCI Dictionary, generally, and in Vol. 2, Section 4 of the Seventh Edition, in particular, incorporated herein by reference. Those skilled in the hair setting art recognize that some ingredients are multifunctional and, hence, can serve more than one purpose in the formulation. Thus, the amount of RMHS (ASAP and/or HASE) polymer employed as the sole hair setting agent and additional product components is not limited, as long as the purpose and properties of the hair setting composition performs its intended function.

While the RMHS polymer minimizes or eliminates the need for added thickeners, the RMHS polymer can be used in combination with conventional polymeric thickeners, such as natural gums, resins, and synthetic nonionic or anionic polymeric thickeners, popularly used in the art. It is known that the viscosity obtained with the anionic, alkali-swellable carbomer polymer, commonly employed as a thickener, can be negatively affected by the presence of anionic polymer. Surprisingly, it was found that the alkali-swellable ASAP were compatible with either traditional carbomer polymer or with hydrophobically-modified carbomer polymer and the viscosity produced by such combinations was unexpectedly higher than the sum of the viscosities of alkali-swellable ASAP and carbomer polymer by themselves at the same concentrations. This beneficially allows the use of alkali-swellable ASAP in formulations containing carbomer polymer or hydrophobically modified carbomer polymer, if desired, to further enhance the aesthetic and rheological properties of the formulation, including enhanced electrolyte (i.e., salt) tolerance and gel pickup.

Hair setting compositions requiring rheology modification are well known from the cosmetic literature and can include, without being limited thereto, hair waving and hair straightening products, as well as hair style maintenance products, and can be applied in the form of liquid rinses, pressurized aerosol and non-pressurized aerosol sprays, spritzes, mousses, foams, gels, emulsions in lotion and cream form, styling shampoos, solids, such as styling sticks, semi solids, and the like, and employing any aqueous or water-containing formulation medium that requires modification of rheology. Hair setting compositions are commonly commercialized in varying efficacy strengths, identified, for example, as "extra hold", "firm hold", or "soft hold", and in varying product forms, i.e., liquids, sprays, lotions, creams, gels, mousses, spritzes, foams, and the like. While the RMHS polymer beneficially can be the sole hair setting agent, it can be combined, if desired, with auxiliary conventional polymeric hair fixatives and film formers known in the art, such as natural gums, resins, neutral, or anionic, or cationic or amphoteric polymers of synthetic design.

Hair setting formulations containing the RMHS polymers can be delivered from water, water/organic solvent mixtures, or solvent/propellant systems. Preferably, the RMHS polymers are dissolved in a polar solvent, such as water or water-ethanol mixture. The RMHS polymer can be employed in unneutralized form or the pH can be adjusted with an organic or inorganic base to above about 3. Where clarity of the product is important or desirable, the pH is adjusted until the product is substantially clear or translucent, preferably in the range of about 5 to about 7.5. Preferred organic solvents are $C_2$–$C_6$ monohydric alcohols, such as ethanol, propanol, isopropanol, benzyl alcohol and the like, and $C_3$–$C_8$ polyols, such as propylene glycol, glycerin, hexylene glycol, butylene glycol, inositol, sorbitol, mannitol, and the like.

The hair setting compositions of the invention can be provided and dispensed from assorted package forms known in the art, i.e., pressurized and non-pressurized containers, such as cans, bottles, packets, ampoules, jars, tubes, and the like. In another packaged form embodiment, the hair setting compositions can be dispensed to the hair from a hair setting aid impregnated with the hair setting composition or coated with the hair setting composition. The term "hair setting aid", as used herein, refers to wipes, pads, towlettes, sponges, curling papers, hair combs, hair brushes, hair curlers, such as sponge hair rollers, and the like, that can serve as substrates for holding and delivering RMHS polymer to hair. The hair setting aid can be impregnated with hair setting composition, such as by soaking, immersing, saturating, and the like, or the hair setting aid can be coated with the hair setting composition, such as by brushing, spraying, dipping, and the like, and then packaged, while wet or in substantially dried form. In still another packaged form embodiment, the hair setting compositions can be provided as a kit, as discussed in more detail below.

Hair setting spray compositions can be dispensed from finger-actuated pump devices, either as pressurized aerosol sprays, mousses, spritzes, and foams containing propellant, or as non-pressurized, mechanically propelled sprays and foams. When an RMHS polymer of the invention is formulated into a pressurized aerosol composition, the propellant can be any environmentally and physiologically tolerable fluorinated hydrocarbon, such as difluoroethane and tetrafluoroethane, hexafluoroethane, and the like; dimethyl ether; liquid volatile hydrocarbons, such as propane, isobutane, n-butane and mixtures thereof; and compressed gas, such as carbon dioxide, nitrous oxide and nitrogen. The amount of propellant is governed by the spray characteristic and pressure factors desired as is well known in the aerosol art. Pressurized aerosol hair setting compositions preferably contain concentrations of environmentally and physiologically acceptable solvent/propellant combinations that meet legislated federal and state governmental requirements for volatile organic compounds (VOC). For low VOC compositions, the solvent system preferably is water or includes at least about 20 to about 50 weight percent water, and preferably contains not more than about 25 weight percent of organic solvent. For mousse products, the level of propellant can be in the range of about 1 to about 30 weight percent, preferably from about 3 to about 15 weight percent of the total composition.

Foam hair setting compositions can be of a "postfoaming" gel to mousse type product where volatile liquid hydrocarbon is dispersed in the hair setting composition and then packaged in a container, such as a bag-in-can, SEPRO-can, sealed and pressurized on the outside of the bag, as known in the art. Alternatively, foam hair setting compositions can be a gel or mousse formulation that is mechanically aerosolized by placing it in a finger-actuated nonpressurized pump dispenser.

The hair setting compositions can be hair cosmetic type products containing hair colorants, such as colorant styling gels or styling sticks for concurrently providing temporary hair color.

The hair setting compositions can also contain, without limitation thereto, additives that modify the polymer character, such as plasticizers, humectants, tackifiers, detackifiers, wetting agents and antistatic agents, preservatives, fragrance and fragrance solubilizer. The hair setting compositions of this invention can be formulated as water-in-oil, oil-in-water, or multiphase emulsions in the form of liquids, creams, pastes, ointments and the like. The hair setting compositions of this invention are unlimited as to product form and can be clear, translucent or opaque.

The hair setting compositions can include, without being limited thereto, as hair conditioning agents, volatile and nonvolatile silicone compounds, silicone gums and rigid silicones polymers. A description of rigid silicone polymers is found in U.S. Pat. No. 4,902,499, and is incorporated herein by reference.

In one preferred hair setting composition embodiment of this invention, the hair setting composition can be prepared by the user, such as a beautician or a customer, by providing them with a packaged hair setting amount of RMHS polymer, in an unneutralized or partly neutralized form, and optionally, a packaged liquid, or solid, composition containing an effective amount of pH adjusting agent and all or a portion of the remaining ingredients, if any. For use, the user can mix together all or a portion of the contents of the two packages in an aqueous medium. Mixing can be performed in a container, such as with a wooden spatula or like simple mixing device, or by placing the contents in a jar and mixing with shaking, or hand stirring; to tailor the viscosity of the hair setting composition to the consistency desired.

A hair setting kit embodiment, without being limited thereto, can comprise at least one container, such as a bottle, ampoule, squeezable tube, packet, and the like, and instructional information for preparation and use of the product. For example, a useful kit embodiment can provide one container comprising an aqueous RMHS emulsion product in concentrated or diluted liquid form; and a second container can comprise a base, such as AMP. For use, the contents of the first container can be added to a selected amount of water, preferably distilled, deionized, or soft tap water, mixed with stirring or shaking, and then gradually mixed with the contents of the second container, blending until the desired consistency is achieved. Alternatively, the contents of the first container can include sufficient water to provide a concentrate of the RMHS emulsion product, so that the only the contents of the second container need be added. A useful kit can also include a hand-held manual mixing device, such as a wood or plastic spatula, disposable gloves, mixing container, comb, hair curlers and the like, for the convenience of the customer. Additionally, a useful kit can further include auxiliary cosmetic hair care adjuvants, such as conditioners and additives for providing marketing appeal, incorporated either as ingredients to the contents of one or both of the containers or provided in a separate container or package.

The instructional material can be printed media, aural media, visual aids, electronic media or a combination thereof, which instruct the user on how to prepare and/or use the hair setting compositions of the invention. Printed media includes, but is not limited to, labels, pamphlets, books, flyers and the like. Aural media includes, but is not limited to, tape recordings, audio compact disks, records, and the like. Visual aids include, but are not limited, to photographs, slides, movies, videos, DVDs and the like. Electronic media includes all forms of electronic data storage media, such as, but not limited to, diskettes, interactive CD-ROMs, interactive DVD-ROMs, and the like. In addition, the contents of the kit are preferably packaged in a box, carton, and the like, with instructional indicia printed thereon or affixed thereto.

Thus, whether provided to the user as a finished hair setting composition, or prepared by the user by mixing together the contents provided in a kit embodiment, as previously described, a set can be imparted to hair by the method of applying an effective amount of hair setting composition of this invention to the hair before, during, or after shaping the hair in a desired configuration. When the hair setting composition is provided as an impregnated hair setting aid or coated hair setting aid, the packaged hair setting aid can be provided as a stand-alone product or in a kit form, with auxiliary cosmetic hair care adjuvants, such as discussed above. When the hair setting aid is provided to the customer in a moist or wet form, the customer can contact the-dry hair with the hair setting aid to deliver the hair setting composition thereto. Alternatively, when the hair setting aid is provided to the customer in a substantially dried form, the customer can first wet the hair, such as with water, and then contact the hair setting aid with the wet hair to deliver the hair setting composition thereto. Thus, in the method of setting hair with the hair setting aid, hair setting composition also can be applied to the hair before, during, or after styling the hair into a desired configuration, by contacting the hair with the hair setting aid for a period sufficient to apply hair setting composition to the hair, depending on the form of hair setting aid, and can be readily determined by those skilled in the hair setting art. For example, and not by way of limitation, impregnated or coated wipes, pads, curling papers, towlettes, sponges, and the like, can be used to apply hair setting composition to the hair by contacting the hair on a tress by tress basis before wrapping the tress on a curler or roller or while shaping the configuration of the hair style, and impregnated or coated combs and brushes can be used to apply hair setting composition to the hair before, during, or after styling the hair, whereas impregnated curlers are more suitable for applying the hair setting composition during shaping of the desired configuration.

The following examples further illustrate the preparation and use of preferred embodiments but are not intended to be limiting.

Materials and Procedures

The materials are generally commercially available from chemical supply houses known to those skilled in the chemical arts or from the supplier indicated.

| 1. Materials Abbreviations and Trade Names | |
|---|---|
| EA | Ethyl acrylate |
| WAM | Methacrylamidoethyl-N-ethyleneurea (SIPOMER ® WAM II, Rhodia, Inc.) |
| MAA | Methacrylic acid |
| MMA | Methyl methacrylate |
| AA | Acrylic acid |
| SSSA | Sodium salt of styrene sulfonic acid |
| BEM25 | Beheneth-25 methacrylate |
| LEM23 | Laureth-23 methacrylate |
| HCOEM25 | Hydrogenated castor oil ethoxylated (25) methacrylate |
| HCOEM16 | Hydrogenated castor oil ethoxylated (16) methacrylate |
| TEM25 | Tristyrylphenol ethoxylated (25) methacrylate |
| CHEM24 | Choleth-24 methacrylate |
| CEM24 | Ceteth-24 methacrylate |
| CSEM25 | Ceteareth-25 methacrylate |
| EOBDMA | Ethoxylated (30) bisphenol A dimethacrylate |
| TMPTA | Trimethylolpropane triacrylate |
| IMP | Isooctyl 3-mercaptopropionate |
| DDM | Dodecyl mercaptan |
| ODM | Octadecyl mercaptan |
| R307 | A randomly ethoxylated/propoxylated 1,4-butanediol vinyl ether having the empirical formula $CH_2=CH-O-(CH_2)_4-O-(C_3H_6O)_4-(C_2H_4O)_{30}-H$ (EMULSOGEN ® R307, Clariant Corporation) |
| BX-AA | A randomly ethoxylated/propoxylated allyl ether having the empirical formula $CH_2=CH-CH_2-O-(C_3H_6O)_5-(C_2H_4O)_5-H$ (BX-AA-E5P5, Bimax, Inc.) |
| M5010 | A carboxy-functional $C_{12}-C_{15}$ alkenyl hydrophobe, ethoxylated with about 24 ethylene oxide units (MAXEMUL ® 5010, Uniqema) |
| MPEG35 | Methoxy ethoxylated (35) methacrylate |
| MPEG55 | Methoxy ethoxylated (55) methacrylate |
| PVP | Polyvinylpyrrolidone (K-30, BASF Corp.) |
| PVP/VA | Polyvinylpyrrolidone/vinylacetate copolymer (LUVISKOL ® VA-64, BASF Corp.) |

2. Methods.

A. Viscosity. The reported viscosity of each polymer containing composition was measured in milli-Pascal seconds (mPa·s), employing a Brookfield rotating spindle viscometer, (Brookfield, Model RVT) at about 20 revolutions per minutes (rpm), at ambient room temperature of about 20–25° C. (hereafter referred to as Brookfield viscosity). Viscosity was measured on freshly prepared compositions (referred to as "initial viscosity"), and re-measured after allowing the composition to age for at least about 24 hours at ambient room temperature (referred to as "24-hour viscosity"). Where only one viscosity value is shown below, the viscosity value is the 24-hour viscosity, unless otherwise indicated.

A "thin viscosity" typically refers to a pourable, runny, sprayable product having a viscosity of up to about 1,000 mPa·s; a "medium viscosity" refers to a product having a viscosity of above 1,000 to up to about 3,000 mPa·s; a "high viscosity" refers to a product having a viscosity of above 3,000 to up to about 10,000 mPa·s; and gel refers to a product having a viscosity greater than 10,000 mPa·s, unless otherwise indicated.

B. Clarity. When reported, the % clarity of the polymer-containing composition was measured in % T (transmittance) by Brinkmann PC-920 calorimeter at least about 24 hours after the composition was made. Clarity measurements were taken against deionized water (clarity rating of 100%). Compositions having a clarity of about 60% or more were substantially clear; compositions having a clarity in the range of about 45–59% were judged substantially translucent. For gel compositions, clarity was preferably greater than about 20%, more preferably greater than about 50%, and most preferably about 70% or greater.

C. Glass Transition Temperature. When reported, the glass transition temperature (Tg) of the associative polymer was determined by casting a portion of the product emulsion on a MYLAR® (polyethylene terephthalate) film substrate using a 10 mil opening draw-down bar, drying the cast film at ambient room temperature (about 25° C.) for about 24 hours, and then measuring the $T_g$ by well known Differential Scanning Calorimetry (DSC) technique.

D. Gloss. When reported, the gloss of the associative polymer film was determined by casting a film of the polymer product on a Leneta Form 2C-opacity chart (Leneta Co.) using a 10 mil opening draw down bar, drying the cast film at about 25° C. for about 24 hours, and then instrumentally measuring the specular gloss of the dried film at a reflectance angle of 20° and 60° geometry employing a Micro-Tri-Gloss glossmeter, (Byk/Gardner, Silver Spring, Md.) using the Standard Test Method for Specular Gloss, ASTM 523-89 (Reapproved 1994). A specular gloss value of 100 units was assigned to the standard for each geometry. A specular gloss value unit reading of at least about 30 at an angle of 20° and at least about 80 at an angle of 60° was judged glossy and a unit value of less than 25 at either angle was judged dull.

E. Turbidity. When reported, the turbidity of a polymer-containing composition was determined in Nephelometric Turbidity Units (NTU) employing a nephelometric turbidity meter with distilled water (NTU=0) as the standard. Compositions having NTU values of about 90 or higher were judged visibly turbid.

F. Humidity Resistance—Percent Curl Retention. The hair setting efficacy of a composition was evaluated by the retention of the hair set at high humidity of about 90% Relative Humidity (RH). The ability to hold a curl set on hair after absorption of water from the applied composition and from the surrounding atmosphere was measured employing the well known technique commonly referred to as high humidity curl retention (HHCR). Descriptions of the HHCR methodology are readily found in the cosmetic literature. See, for example, Ch. 30, *Harry's Cosmeticology, 8th Ed.*, M. J. Rieger, Ph.D. (ed.), 666–667, Chemical Publishing Co., Inc., New York, N.Y. (2000), and Diaz et al., *J. Soc. Cosmet. Chem.*, 34, 205–212 (July 1983), the relevant disclosures of each are incorporated herein by reference.

Tresses of commercially blended Caucasian, untreated (virgin) human hair were prepared employing natural brown or black color European hair supplied by International Hair Importers and Products Inc., New York. Each hair tress (about 3 grams weight) was about 7 inches (about 18 cm) in length and was securely anchored with glue at the scalp (root) end portion. Prior to use, each hair tress was pre-cleaned by washing with a dilute aqueous solution of sodium lauryl sulfate (10% SLS), rinsing thoroughly with deionized water at ambient room temperature and drying with towel blotting. The initial extended length of the hair ($L_e$) was measured. About 0.8 grams of polymer-containing composition to be evaluated was applied to the hair tress and distributed from the scalp to end portion. The treated hair tress was then wrapped around a hair curler having an outer diameter of about 3 cm, and allowed to dry on the curler overnight at an ambient room temperature of about 21–23° C. After drying, the curler was carefully removed, leaving the hair styled into a single curl, the initial length of the hair curl ($L_i$) was measured, and the curled hair tress was vertically hung in a humidity chamber set at an ambient temperature of about 26–27° C. and ambient high humidity of about 90% RH.

High humidity curl retention (HHCR) was determined by measuring the length of the hair curl as the curl relaxed after selected intervals ($L_t$) of exposure to humidity. The following equation was used to calculate percent curl retention, relative to the initial curl length ($L_i$) and initial extended length of the hair ($L_e$).

$$\% \text{ Curl Retention} = \frac{L_e - L_t}{L_e - L_i} \times 100$$

The change in curl length (droop, helix formation) was periodically measured and visually observed. Measurements were taken initially, and at 0.25 hour intervals over a total exposure period of about 1.25 to 1.75 hours, and then at hourly intervals thereafter over a total exposure period of up to about 8 hours, with a final reading being taken after a total exposure period of about 24 hours. HHCR efficacy of about 70% or more curl retention (CR) for a minimum period of at least about 0.75 hours at about 90% RH is referred to herein as "T@70% CR", and is a conventional benchmark for good high humidity resistance and is referred to herein as good hair setting efficacy. HHCR efficacy reported herein for a selected time interval is identified as "% CR @T—x ", where x is the hourly interval or fraction thereof. Hair setting efficacy of 70% CR @T—1.25 hours or longer was judged very good, and 70% CR @T—3 hours or longer was judged as excellent. Hair setting efficacy was judged weak when % curl retention was not more than about 50%.

The restylability efficacy of the hair setting composition was evaluated by determining the HHCR following the above procedure (Cycle 1), then thoroughly wetting the hair with water, squeezing excess water out of the hair by hand, resetting and restyling the hair into a single curl as described above and repeating the HHCR procedure (Cycle 2).

G. Subjective Properties Assessment. The tactile-aesthetic and mechanical properties of hair treated with hair setting composition, such as feel, flaking, ease of combing, curl memory and static flyaway were subjectively assessed. The feel and spreadability of the hair setting composition was assessed by the sensory tactile character of the hair setting composition while being hand applied to the hair. The subjective properties of the set hair, such as residue on the hair, if any, was assessed by inspecting the hair for visible deposit (coating) on the hair surface and by combing the treated hair about five times with the fine tooth portion of a hard rubber comb, and then inspecting the tines of the comb for visible residue (flakes). Combing ease and static flyaway of the hair was subjectively assessed during combing by noting hair tangles, flyaway fibers and difficulty in combing through the hair. Curl memory was subjectively assessed after being combed by visually observing the bouncy, curl-up appearance of the hair curl pattern (i.e., complete curl, open helix or spiraling or lack of curl) remaining in the hair after exposure to high humidity of about 90% RH for about 24 hours, unless otherwise indicated.

Where indicated, numerical ratings on a scale of 0–5 were given to the subjective properties based on the following general criteria (Table 2).

TABLE 2

| | Product Characteristics | | Set Hair Characteristics | | |
|---|---|---|---|---|---|
| Rating | Feel | Spreadability | Curl Memory | Residue | Combing |
| 5 | Very slick, non-tacky | Very easy, uniform coating | Complete curl | None | Very, very easy |
| 4 | Smooth, non-tacky | Easy, uniform coating | Good, slightly helical | Trace on comb | Very easy |
| 3 | Very slight tack | Easy, slightly uneven spreading | Uniform helix | Very slight on comb | Easy |
| 2 | Slight tack | Easy, uneven spreading | Non-uniform helix, spiraling | Slight, on comb only | Some tangles, hair soft |
| 1 | Tacky | Difficult, uneven coating | Poor, only end tip curl | Slight, noticeable on comb and hair surface | Static fly-away, hair soft |
| 0 | Very tacky | Poor, very uneven coating | None, no curl | Visible dulling coating | Difficult to comb, tangling |

H. Instrumental Texture Analysis Evaluations

1. Hair Loop Test: The crispness (stiffness), curl retention and restylability of hair treated with the hair setting composition was determined instrumentally employing a texture analysis instrument and hair tresses were configured into an omega-shaped loop (i.e., shaped like the Greek letter (Ω)). The preparation of omega-shaped hair loops and instrumental procedures for determining the mechanical behavior of such preshaped hair were generally based on the description of this test methodology found in J. Jachowicz et al., *J. Soc. Cosmet. Chem.*, 47, 73–84, (1996), the disclosures of which are incorporated herein by reference. This hair loop test assesses fixative hair setting efficacy.

Texture Analysis Instrument: Texture Analyser, Model TA-XT2I (Texture Technologies Corp.), with a load sensitivity of 0.1 gram was placed inside a humidity chamber set at the relative humidity and ambient temperature indicated below. Texture Expert Software, version 1.17 from Stable Microsystems Limited, was used to collect and display the data.

Preparation of Hair Loop: Tresses of commercially blended, Caucasian, untreated (virgin) human hair were prepared employing European hair of natural brown color. Tresses of about 0.3 g weight and about 3.5 inch (about 8.9 cm) length were secured to tabs at both ends by glue, leaving about 1.5 inches (about 3.8 cms) of hair fibers between the tabs as generally described by Jachowicz et al. The tabbed hair was then precleaned as described in method F, towel blotted and about 0.1 of hair setting composition to be evaluated was applied evenly to the hair tress. The treated tress was then shaped into an omega (Ω) loop (hereafter hair loop) using a wooden dowel rod about 0.5 inch (about 1.27 cm) in diameter and the tress was dried in this geometrical shape and conditioned for about 12 hours at an ambient temperature and relative humidity of about 25° C. and 80% RH. The rod was then removed from the hair and the mechanical properties of the hair loop were determined with the Texture Analyser at an ambient temperature and humidity of about 25° C. and about 80% RH— by the following force measurement procedure.

Force Measurement Procedure: The mechanical properties of the conditioned hair loop were measured by positioning the tress under the acrylic cylindrical probe (2.5 cm in diameter) of the Texture Analyser instrument. Each test was performed by oscillating the cylindrical probe (in compression mode) between the fiber surface and the calibration height of about 1 mm above the hair surface. The probe touches the hair surface initially and sensing a force then compresses the hair surface to deform the hair loop downwardly by about 8 mm before rising to the calibration height. An 8 mm penetration produces about 75% deformation of the hair loop to simulate a hair style experiencing aggressive conditions. The deformation of the hair loop was repeated about 5–6 times per minute and the maximum force in each cycle was recorded. The test run time was about 2400 to about 3000 seconds (about 40 to about 50 minutes). For baseline information, an untreated hair loop (control) was also tested. The values of force (peak force, mass in grams) required to deform 75% of the hair loop were plotted as a function of time. The initial force is directly related to the stiffness or crispness of the hair attributed to the fixative hair setting polymer before any deformation occurs. Thus, the higher the force, the stiffer the hair.

Restylability: For evaluating restylability, a hair loop which had been evaluated by the above Hair Loop Test, was reshaped into an omega loop by wetting the tress with deionized water, the steps of Method H for drying and conditioning the hair were repeated and then the Force Measurement Procedure was repeated.

2. Instrumental Comb-Through Measurement: Hair tresses were prepared and pre-cleaned as described in Method F, except that the scalp end portions of the tresses were anchored by a crimped metal band. Typically about 0.1 grams of composition was applied to and distributed through a tress and wet comb-through was instrumentally measured employing the Texture Analyser instrument described above and the measurement procedure described below. For measuring dry comb-through, the treated tress was dried overnight in a humidity chamber set at an ambient temperature of about 23° C. and a relative humidity of about 50% RH. Baseline values for the untreated hair (control) were also measured.

Instrumental Comb-Through Measurement Procedure: The Texture Analyser instrument described above and it's A/TG Tensile Grip accessories were placed in the humidity chamber and equilibrated at an ambient temperature of about 23° C. and about 50% RH. A hard rubber comb (Model 220041, Sally's Beauty Supply) was affixed to a specially designed aluminum plate on the base of the Texture Analyser so that about 30 mm of the fine-tooth portion of the comb was horizontally attached to the aluminum plate. The banded portion of the tress was then placed in the Tensile Grip. The Tensile Grip was lowered and all but the top ¾ inch (about 1.9 cm) of the tress was positioned within the exposed teeth of the comb. The tress was then combed by raising the Tensile Grip to pull the hair through the teeth of the comb at a rate of about 3 mm/s until the full length of the tress had been completely passed through. The work force (grams) needed to raise the tress was recorded as a function of distance. The comb-through procedure was repeated four times on the same tress, for a total of five comb-through pulls. For baseline measurement, each hair tress was measured five times for both wet and dry comb through before applying test composition, and both wet and dry measurements were repeated after applying test composition. For each tress, an "Easy Comb-Through Factor" (ECF) value was calculated as follows from the recorded values collected for force and distance employing the Texture Expert Software, version 1.17 and corrected for offset.

The five force values collected after the wet and dry comb-through measurements for each tress were averaged. Baseline values were calculated as average work force in grams for untreated hair and substituted in the equation below to determine the ECF value.

$$ECF = \frac{\text{Average work force in grams for treated hair}}{\text{Average work force in grams for untreated hair}}$$

An ECF value in the range of 1 to 1.5 is considered as very easy. For a given polymer or formulation, therefore, the lower the value, the easier the comb-through, which further reflects good manageability of the hair.

I. Method of Preparing RMHS Polymer. For illustration, and not by limitation, product ASAP emulsions shown in Tables 4A, 4B, 4C and 4D, and the HASE polymer product emulsions shown in Table 3 of Example 1 were prepared according to the following general Method.

A monomer emulsion is prepared in a first reactor equipped with a nitrogen inlet and an agitator, by combining a desired amount of each monomer in water containing an emulsifying amount of an anionic surfactant under a nitrogen atmosphere, with mixing agitation. To a second reactor equipped with a mixing agitator, nitrogen inlet and feed pumps, are added a desired amount of water and additional anionic surfactant, if desired, and the contents are heated under a nitrogen atmosphere with mixing agitation. After the second reactor reaches a temperature in the range of about 80–90° C., a desired amount of a free radical initiator is injected into the surfactant solution in the second reactor, and the monomer emulsion from the first reactor is then gradually pumped into the second reactor over a period in the range of about one to about four hours, at a controlled reaction temperature in the range of about 80–90° C. After completion of the monomer addition, an additional quantity of free radical initiator can be added to the second reactor, if desired, and the resulting reaction mixture is held at a temperature of about 90–95° C. for a time period sufficient to complete the polymerization reaction, typically about 90 minutes. The resulting polymer emulsion can then be cooled, discharged from the reactor and collected.

J. Methods for Preparing Hair Setting Compositions. Unless otherwise indicated, the HASE and ASAP product emulsions prepared by Method I, as supplied, were diluted with water to obtain the desired polymer concentration or were added to a formulation with the water soluble ingredients in an amount sufficient to provide the desired polymer concentration in the finished formulation. Commercial HASE polymer emulsions, as supplied, were similarly diluted with water to obtain the active polymer weight % indicated, based on the technical information available from the manufacturer's technical data sheets or the literature. All references to weight % polymer means active weight % polymer on a total formulation weight basis. Unless otherwise indicated, formulations were prepared employing conventional formulation equipment and techniques well known to those skilled in the cosmetic formulation arts.

EXAMPLE 1

RMHS Polymers

The alkali-swellable ASAP, identified as Polymer A in Table 4A, was prepared according to the general procedure described as Method I, and as described in detail below.

A monomer reaction mixture was prepared in a first reactor, under a nitrogen atmosphere, using an agitator mixer rotating at about 500 rpm, by combining about 117 parts by weight of methacrylic acid, about 172 parts by weight of ethyl acrylate, about 25.5 parts by weight of BEM25, and about 3.2 parts by weight of LEM23 into about 92 parts by weight of deionized water containing about 10.6 parts by weight of 30% aqueous sodium lauryl sulfate. To a second reactor, equipped with a mixing agitator, nitrogen inlet and feed pumps, were added about 570 parts by weight of deionized water and about 3.2 parts by weight of 30% aqueous sodium lauryl sulfate. The contents of the second reactor were heated with mixing agitation at a rotation speed of about 200 rpm under a nitrogen atmosphere. After the contents of the second reactor reached a temperature in the range of about 85–88° C., about 6.3 parts of 3.5% ammonium persulfate solution (a free radical initiator) was injected into the so-formed hot surfactant solution in the second reactor. The aqueous emulsion of the monomer mixture from the first reactor was gradually pumped into the second reactor over a period of about 60 minutes at a controlled reaction temperature in the range of about 85–88° C. At the completion of the monomer mixture addition, about 9.4 parts by weight of 0.7% ammonium persulfate solution was added to the reaction mixture in the second reactor and the temperature of the reaction was maintained at about 90° C. for an additional one and half hours to complete polymerization. The resulting product emulsion was cooled to room temperature, discharged from the reactor and collected.

HASE Polymers H-1, H-2, H-3, H-4, and H-5, each having the monomer components shown in Table 3, alkali-swellable ASAP, Polymers B-M, N-Z and AA-AW, and alkali-soluble ASAP, Polymers BA through BL, each having the monomer components, as shown, respectively, in Tables 4A, 4B, 4C and 4D were prepared following the general method for the preparation of Polymer A, above. All monomers listed for a given polymer, were included in the monomer reaction mixture in the first reactor and the relative amounts of the monomers were adjusted, as needed, to achieve the monomer weight percent values listed in Tables 3, 4A, 4B, 4C and 4D; all % values in the tables are weight percent, based on total monomer mixture weight.

All of the polymers were prepared as aqueous solutions having total solids levels in the range of about 30 to about 45%. In most cases, sodium lauryl sulfate (SLS) was utilized as the emulsifying surfactant for the polymerization reaction. In addition, Polymer AV was also successfully prepared according to the foregoing procedure utilizing a combination of SLS and nonionic emulsifying surfactant, i.e., Ceteareth-20 (INCI name for polyoxyethylene (20) cetyl/stearyl ether). In the preparations of Polymers BH, BK, and BL, the following surfactants were utilized in place of SLS, respectively: RHODAFAC® 610 (a complex phosphate ester of a branched alcohol ethoxylate, available from Rhodia, Inc., Cranbury, N.J.), disodium laureth-3-sulfosuccinate, and sodium dioctyl sulfosuccinate.

TABLE 3

HASE Polymer Compositions

| Polymer No. | Acidic Vinyl Monomer (%) | Nonionic Vinyl Monomer (%) | Associative Monomer(s) (%) | Other Monomer(s) (%) |
|---|---|---|---|---|
| H-1 | MAA (37) | EA (53.7) | BEM25 (9) | EOBDMA (0.3) |
| H-2 | MAA (37) | EA (53) | BEM25 (10) | |
| H-3 | MAA (37) | EA (59.7) | BEM25 (3) | TMPTA (0.3) |
| H-4 | MAA (37) | EA (53.55) | BEM25 (8); CSEM25 (1) | EOBDMA (0.3); IMP (0.15) |
| H-5 | MAA (36) | EA (60.9) | BEM25 (3) | TMPTA (0.1) |

TABLE 4A

Alkali-Swellable ASAP Compositions

| Poly. No. | Acidic Vinyl Monomer(s) (%) | Nonionic Vinyl Monomer(s) (%) | Associative Monomer(s) (%) | Optional Monomer(s) (%) |
|---|---|---|---|---|
| A | MAA (37) | EA (54) | BEM25 (8); LEM23 (1) | |
| B | MAA (34); AA (2) | EA (55.85); WAM (3) | BEM25 (4); LEM23 (1) | TMPTA (0.1); EOBDMA (0.05) |
| C | MAA (37) | EA (53.7) | BEM25 (8); LEM23 (1) | EOBDMA (0.3) |
| D | MAA (37) | EA (53.7) | BEM25 (8); HCOEM25 (1) | EOBDMA (0.3) |
| E | MAA (37) | EA (53.7) | BEM25 (8); HCOEM16 (1) | EOBDMA (0.3) |
| F | MAA (37) | EA (53.7) | BEM25 (8); TEM25 (1) | EOBDMA (0.3) |
| G | MAA (37) | EA (53.85) | BEM25 (8); LEM23 (1) | IMP (0.15) |
| H | MAA (37) | EA (53.55) | BEM25 (8); LEM23 (1) | EOBDMA (0.3); IMP (0.15) |
| I | MAA (37) | EA (53.85) | BEM25 (8); LEM23 (1) | ODM (0.15) |
| J | MAA (37) | EA (53.55) | BEM25 (8); LEM23 (1) | ODM (0.15); EOBDMA (0.3) |
| K | MAA (37) | EA (57.9) | BEM25 (4); LEM23 (1) | TMPTA (0.1) |
| L | MAA (37) | EA (53.7) | BEM25 (6); LEM23 (3) | EOBDMA (0.3) |
| M | MAA (37) | EA (57.7) | BEM25 (4); LEM23 (1) | TMPTA (0.15); EOBDMA (0.15) |

TABLE 4B

Alkali-Swellable ASAP Compositions

| Poly. No. | Acidic Vinyl Monomer (%) | Nonionic Vinyl Monomer (%) | Associative Monomer(s) (%) | SH Monomer (s) (%) | Optional Monomer(s) (%) |
|---|---|---|---|---|---|
| N | MAA (37) | EA (59.7) | | CHEM24 (1.5); CEM24 (1.5) | EOBDMA (0.3) |
| O | MAA (37) | EA (56.7) | BEM25 (3); | CHEM24 (1.5); CEM24 (1.5) | EOBDMA (0.3) |
| P | MAA (37) | EA (59.9) | BEM25 (2); LEM23 (1) | | TMPTA (0.1) |

TABLE 4B-continued

Alkali-Swellable ASAP Compositions

| Poly. No. | Acidic Vinyl Monomer (%) | Nonionic Vinyl Monomer (%) | Associative Monomer(s) (%) | SH Monomer(s) (%) | Optional Monomer(s) (%) |
|---|---|---|---|---|---|
| Q | MAA (36) | EA (58.1) | BEM25 (2); LEM23 (1) | R307 (2.8) | TMPTA (0.1) |
| R | MAA (35) | EA (58.9) | BEM25 (2); LEM23 (1) | M5010 (3) | TMPTA (0.1) |
| S | MAA (35) | EA (56.9) | BEM25 (2); LEM23 (1) | R307 (3); M5010 (2) | TMPTA (0.1) |
| T | MAA (37) | EA (42.8) | BEM25 (15); LEM23 (5) |  | TMPTA (0.05); EOBDMA (0.15) |
| U | MAA (37) | EA (57.8) | BEM25 (4); LEM23 (1) |  | TMPTA (0.2) |
| V | MAA (37) | EA (53.7) | BEM25 (3); LEM23 (6) |  | EOBDMA (0.3) |
| W | MAA (37) | EA (53.7) | BEM25 (4.5); LEM23 (4.5) |  | EOBDMA (0.3) |
| X | MAA (36) | EA (55.9) | BEM25 (2); LEM23 (1) | BX-AA (5) | TMPTA (0.1) |
| Y | MAA (36) | EA (54.9) | BEM25 (3); LEM23 (1) | R307 (5) | TMPTA (0.1) |
| Z | MAA (36) | EA (55.9) | BEM25 (2); LEM23 (1) | R307 (5) | TMPTA (0.1) |

TABLE 4C

Alkali-Swellable ASAP Compositions

| Poly. No. | Acidic Vinyl Monomer(s) (%) | Nonionic Vinyl Monomer(s) (%) | Associative Monomer(s) (%) | SH Monomer (%) | Optional Monomer (%) |
|---|---|---|---|---|---|
| AA | MAA (37); SSSA (5) | EA (51) | BEM25 (6); LEM23 (1) |  |  |
| AB | MAA (36) | EA (55.2) | BEM25 (2.5); CHEM24 (0.5); CEM24 (0.5) | R307 (5) | EOBDMA (0.3) |
| AC | MAA (52); AA (2) | EA (42.7) | BEM25 (2); LEM23 (1) |  | EOBDMA (0.3) |
| AD | MAA (36) | EA (48.7) | BEM25 (10); LEM23 (5) |  | EOBDMA (0.3) |
| AE | MAA (37) | EA (59.7) | BEM25 (2); LEM23 (1) |  | EOBDMA (0.3) |
| AF | MAA (36) | EA (58.4) | BEM25 (3) | R307 (2.5) | TMPTA (0.1) |
| AG | MAA (36) | EA (55.9) | BEM25 (3) | R307 (5) | TMPTA (0.1) |
| AH | MAA (36) | EA (53.4) | BEM25 (3) | R307 (7.5) | TMPTA (0.1) |
| AI | MAA (36) | EA (45.9) | BEM25 (3) | R307 (15) | TMPTA (0.1) |
| AJ | MAA (37) | EA (53.7) | BEM25 (8) | MPEG35 (1) | EOBDMA (.3) |
| AK | MAA (37) | EA (53.7) | BEM25 (8) | MPEG55 (1) | EOBDMA (.3) |
| AL | MAA (2.5); AA (31) | EA (57.5) | BEM25 (8) | MPEG55 (1) |  |
| AM | MAA (36) | EA (57.9) | BEM25 (2); CHEM24 (0.5); CEM24 (0.5) | R307 (3) | TMPTA (0.1) |
| AN | MAA (35) | EA (56.9) | BEM25 (4); LEM23 (1) | M5010 (3) | TMPTA (0.1) |
| AO | MAA (36) | EA (52.9) WAM (3) | BEM25 (4); LEM23 (1) | BX-AA (3) | TMPTA (0.1) |
| AP | MAA (36) | EA (50.9) WAM (3) | BEM25 (4); LEM23 (1) | BX-AA (5) | TMPTA (0.1) |
| AQ | MAA (36) | EA (53.85) | BEM25 (4); LEM23 (1) | BX-AA (5) | TMPTA (0.15) |
| AR | MAA (37) | EA (48.8) | CSEM25 (9) | BX-AA (5) | TMPTA (0.2) |
| AS | MAA (36) | EA (54.7) | BEM25 (8); LEM23 (1) |  | TMPTA (0.3) |
| AT | MAA (37) | EA (51.8) | CSEM25 (10) | BX-AA (1) | TMPTA (0.2) |
| AU | MAA (37) | EA (51.8) | CSEM25 (10) | R-307 (1) | TMPTA (0.2) |
| AV | MAA (37) | EA (52.8) | CSEM25 (8) | BX-AA (2) | TMPTA (0.2) |
| AW | MAA (47) | EA (46.8) | CSEM25 (4) | BX-AA (2) | TMPTA (0.2) |

TABLE 4D

Alkali-Soluble ASAP Compositions

| Poly. No. | Acidic Vinyl Monomer(s) (%) | Nonionic Vinyl Monomer(s) (%) | Associative Monomer(s) (%) | SH Monomer (%) | Chain Transfer Agent (%) |
|---|---|---|---|---|---|
| BA | MAA (29); | EA (43.2); MMA (19.5) | BEM25 (2.5); LEM23 (1) | R307 (2); M5010 (2) | DDM (0.8) |
| BB | MAA (28.64) | EA (44.44); MMA (19.26) | BEM25 (2.47) | R307 (1.975); M5010 (1.975) | DDM (1.24) |
| BC | MAA (28.64) | EA (44.44); MMA (19.26) | LEM25 (2.47) | R307 (1.975); M5010 (1.975) | DDM (1.24) |
| BD | MAA (28.64) | EA (44.44); MMA (19.26) | CSEM25 (2.47) | R307 (1.975); M5010 (1.975) | DDM (1.24) |
| BE | MAA (25) | EA (47.74); MMA (19.5) | BEM25 (2.5) | R307 (2); M5010 (2) | DDM (1.26) |
| BF | MAA (29) | EA (43.74); MMA (19.5) | LEM25 (2.5) | R307 (2); M5010 (2) | DDM (1.26) |
| BG | MAA (29) | EA (43.74); MMA (19.5) | CSEM25 (2.5) | R307 (2); M5010 (2) | DDM (1.26) |
| BH | MAA (24.78) | EA (48.56); MMA (19.33) | BEM25 (2.48) | R307 (1.98); M5010 (1.98) | DDM (0.89) |
| BI | MAA (25) | EA (50.74); MMA (19.5) | BEM25 (2.5) | M5010 (1) | DDM (1.26) |
| BJ | MAA (25) | EA (50.74); MMA (19.5) | BEM25 (2.5) | BX-AA (1) | DDM (1.26) |
| BK | MAA (17.5) | EA (52.74); MMA (25) | BEM25 (2.5) | BX-AA (1) | DDM (1.26) |
| BL | MAA (25) | EA (50.74); MMA (19.5) | CSEM25 (2.5) | BX-AA (1) | DDM (1.26) |

After preparation, each of the resultant HASE polymer emulsions shown in Table 3 and the ASAP polymer emulsions shown in Tables 4A, 4B and 4C, were analyzed to determine the pH, percent total solids (TS) based on active polymer content, and Brookfield viscosity (spindle #2, 20 rpm, ambient room temperature). Additionally, the glass transition temperature (Tg) of selected product polymers were determined by Method C above. The unneutralized product polymer emulsions generally had a pH of not more than about 5.5, typically in the range of about pH 2.5–4.5; total solids (TS) in the range of about 15 to about 45 weight percent; a Brookfield viscosity in the range of about 10 to not more than about 100 mPa·s, and a Tg in the range of about 35° C. to about 150° C. The pH of the polymer emulsions can be adjusted with acidic agents or alkaline agents to a pH preferably in the range of about 5 to about 7.5, or until the composition is substantially clear or translucent, as desired. Where clarity is not a problem or where a more alkaline pH is desired, the pH of the composition can be adjusted to an alkaline pH of even greater than 12 and remain alkali stable.

Alkali-soluble associative polymers of the present invention, exemplified by Polymers BA through BL in Table 4D, above, are useful in a variety of applications as foam enhancers, foam stabilizers, and as film formers in products where relatively low, thin viscosity is desired.

Aqueous solutions of Polymers BE, BF, BG, BI, BJ and BK, each of which contain one associate monomer, were prepared at active polymer weight concentrations of about 3, 5, and 10%, and were neutralized to a pH in the range of about 6.5 to about 7.5 with AMP (95%). At a concentration of about 3% by weight, the Brookfield viscosities of the solutions was too low to measure. At about 5% by weight, each of the polymers afforded a solution having a Brookfield viscosity of not more than about 25 mPa·s. Even at about 10% concentration, the polymers all afforded aqueous solutions with Brookfield viscosities of not more than about 300 mPa·s.

Aqueous solutions of Polymer BA, which has two associative monomers, were similarly prepared as described above. The Brookfield viscosity, at a concentration of about 3% was less than about 15 mPa·s, at about 5% was about 61 mPa ·s and at about 10% was about 850 mPa ·s.

In contrast, a 5% solution of a polymer similar to Polymers BI and BJ, but lacking the semihydrophobic monomer (i.e., a polymer comprising 48.2% EA, 19.5% MMA, 29% MAA, 2.5% BEM25, and 0.8% DDM) had a Brookfield viscosity of greater than about 3000 mPa·s and an undesirable stringy texture. Likewise, a 5% solution of another similar polymer having neither a semihydrophobic monomer nor a chain transfer agent (i.e., a polymer comprising 49% EA, 19.5% MMA, 29% MAA and 2.5% BEM25) had a Brookfield viscosity of greater than about 300,000 mPa·s and an undesirable lumpy texture.

The alkali-soluble associative polymers of the present invention are judged as excellent film formers, foam enhancers, and foam stabilizers for aqueous, and hydro-alcoholic, pump hair spray and spray foam hair setting products, such as foaming hair fixatives, mousses and the like. The polymers are compatible and soluble in aqueous alcohol solutions containing up to at least about 55% by volume ethanol, at polymer concentrations of at least about 5% by weight making them suitable for low VOC and high VOC compositions.

The alkali-soluble associative polymers of the present invention are also compatible with hydrocarbons, making the polymers useful in high VOC spray applications (up to at least about 85% VOC) as well. For example, the solubility of Polymer BJ in a solution of 20% by volume cyclohexane and ethanol (95%, q.s. to about 100% volume) was about 5% by weight at room temperature and about 2% by weight at a temperature of about 4° C. based on clarity (i.e., no cloud).

In a solution of 50% by volume cyclohexane and 50% by volume ethanol (95%), Polymer BJ was soluble at a concentration of about 1% by weight at both room temperature and at about 4° C.

Polymers BG and BI were also formulated in 55% aqueous ethanol at a level of about 5% by weight polymer and neutralized with AMP (95%) to a pH in the range of about 7 to about 8. Each polymer provided a solution having a Brookfield viscosity of about 5 mPa·s. Polymer BG provided a fine mist spray when manually pumped from a finger-actuated pump sprayer. Polymer BI afforded a rich, thick, glossy foam when dispensed from a non-pressurized, foam dispenser (e.g. such as mechanical foam dispensers available from Airspray International, Inc., Pompano Beach, Fla.). Both formulations provided excellent high humidity resistance and curl retention (at 90% RH) when applied to hair. The polymers did not leave a flaky residue on the hair and washed out easily. Both polymers provided a HHCR T@70% CR of greater than about 8 hours.

The alkali-soluble ASAP are judged useful for hydrocarbon-based (n-butane, pentane, and isobutane) pressurized aerosol and non-pressurized aerosol formulations.

EXAMPLES 2–8

Aqueous Hair Setting Compositions

Examples 2–8 illustrate the rheology modification and % clarity achieved in aqueous hair setting compositions containing HASE polymers H-1 and H-4 (Ex. 2–3 and 7–8, respectively), and ASAP (Ex. 4–6) in the amounts shown in Table 5, with the HHCR hair setting efficacy of the compositions shown in Table SA, as determined by Method F. HASE Polymers H-1 and H-4 of Example 1 are crosslinked, hydrophobically modified alkali-swellable emulsion polymers, having one and two associative monomers, respectively. The ASAP hair setting agents, Polymers C and D, each employ one associative monomer (BEM25) that is the same associative monomer of the HASE Polymers H-1 and H-4, and various different associative monomers (i.e., a linear alkyl group (LEM23), or complex ester (HCOEM25)).

The aqueous hair setting compositions were each prepared by diluting the indicated product polymer emulsion of Example 1 with deionized water to obtain the desired active polymer concentration and then neutralizing the diluted polymer emulsion with 2-amino-2-methyl-1-propanol (AMP, 95%) to a pH of about 5.8 to about 7.5, or until the composition was substantially clear. The % clarity value was obtained by Method B, the viscosity was measured by Method A.

TABLE 5

| Ex. No. | Poly. No. | Wt % Poly. | pH | % Clarity | Viscosity mPa·s Immed. | Viscosity mPa·s 24 hrs. |
|---|---|---|---|---|---|---|
| 2 | H-1 | 1 | 7.4 | 67.5 | 14,300 | 18,400 |
| 3 | H-1 | 1.2 | 7.3 | 67.1 | 21,750 | 36,800 |
| 4 | C | 1 | 6.6 | 68.0 | 14,100 | 30,600 |
| 5 | C | 1.2 | 6.6 | 68.3 | 28,900 | 51,400 |
| 6 | D | 1 | 6.5 | 83.6 | 7,800 | 11,750 |
| 7 | H-4 | 1 | 6.2 | 94.7 | 1,000 | 1,440 |
| 8 | H-4 | 1.2 | 6.3 | 92.6 | 10,300 | 12,060 |

TABLE 5A

| | | | HHCR@90% RH | | | |
|---|---|---|---|---|---|---|
| Ex. No. | T@ 70% CR | % CR@T-0.75 | % CR@ T-1.25 | % CR@ T-4 | % CR@ T-8 | % CR@ T-24 |
| 2 | 4 | 92 | 88 | 76 | 44 | 36 |
| 3 | 7 | 100 | 96 | 84 | 67 | 63 |
| 4 | 24 | 100 | 96 | 92 | 88 | 84 |
| 5 | 24 | 100 | 100 | 97 | 97 | 97 |
| 6 | 3 | 81 | 77 | 66 | 50 | 47 |
| 7 | 24 | 100 | 100 | 89 | 81 | 81 |
| 8 | 24 | 96 | 96 | 92 | 92 | 92 |

CR = Curl Retention, as described in Method F.

As shown in Table 5 each of the aqueous compositions containing the ASAP hair setting agent, Polymer C, achieved an initial gel viscosity substantially similar to that of HASE Polymer H-1 at corresponding active polymer concentrations of about 1 and about 1.2 weight %. After 24 hours, the viscosities of the ASAP hair setting gels increased, however, to a substantially greater viscosity than that of the hair setting gels containing HASE Polymer H-1 at the corresponding concentration. Further, the aqueous hair setting gels made with ASAP, Polymers C and D, achieved clarity at a lower pH (pH<7) than did HASE Polymer H-1 (pH>7). HASE Polymer H-4 provided a significantly lower viscosity hair setting composition at about 1% than at about 1.2%, but clarity was similar. As shown in Table 5A, the HHCR hair setting efficacy of all of the hair setting compositions was excellent and surprisingly long-lasting. Based on subjective combing evaluations, curl memory was also judged good.

EXAMPLES 9–11

Aqueous Hair Setting Gels

The procedure of Examples 2–8 was followed, except that the polymers employed were the ASAP hair setting agents, Polymer A (Ex. 9), K (Ex. 10) and L (Ex. 11), each at an active polymer weight concentration of about 1.2%, as shown in Table 6 below with the HHCR hair setting efficacy of the compositions shown in Table 6A. Polymer A is a non-crosslinked analog of Polymer C of Examples 4–5. Polymers K and L illustrate crosslinked polymers having different crosslinkers and varying hydrophobe content.

TABLE 6

| Ex. No. | Poly. No. | Wt % Poly. | pH | % Clarity | Viscosity mPa·s Immed. | Viscosity mPa·s 24 hrs. |
|---|---|---|---|---|---|---|
| 9 | A | 1.2 | 6.8 | 79.9 | 49,980 | 116,200 |
| 10 | K | 1.2 | 6.6 | 77.7 | 30,500 | 62,600 |
| 11 | L | 1.2 | 7.2 | 80.1 | 39,800 | 86,800 |

TABLE 6A

| | | | HHCR@90% RH | | | |
|---|---|---|---|---|---|---|
| Ex. No. | T@ 70% CR | % CR@T-0.75 | % CR@ T-1.25 | % CR@ T-4 | % CR@ T-8 | % CR@ T-24 |
| 9 | 24 | 100 | 97 | 81 | 81 | 81 |
| 10 | 24 | 100 | 97 | 97 | 97 | 97 |
| 11 | 24 | 100 | 100 | 92 | 88 | 84 |

As shown in Table 6A, the hair setting gels containing non-crosslinked ASAP hair setting agent Polymer A (Ex. No. 9) had better clarity and higher viscosity than the hair setting gel containing non-crosslinked ASAP, Polymer C of Example 5. The aqueous hair setting gels made with ASAP, Polymers K and L (Ex. Nos. 10 and 11), also demonstrated good thickening and clarity. As shown in Table 6A, the hair setting efficacy of all the compositions was very good to excellent and sustained. Based on subjective combing evaluations, curl memory was also judged excellent.

EXAMPLES 12–13

Aqueous Hair Setting Gels

The procedure of Examples 2–8 was followed, except that the RMHS polymers employed were ASAP, Polymer N (Ex. 12A, 12B) and Polymer O (Ex. 13A, 13B, 13C), employed at the various active polymer weight % indicated in Table 7, with the HHCR hair setting efficacy of the compositions shown in Table 7A. Polymer O has three different associative monomers, two of which have linear alkyl hydrophobic end groups, and one of which has a carbocyclic alkyl hydrophobic end group; and Polymer N has two associative monomers, one having a linear alkyl hydrophobic end group, and the other a carbocyclic alkyl hydrophobic end group.

TABLE 7

| Ex. No. | Poly. No. | Wt % Polymer | pH | % Clarity | Viscosity mPa · s Immed. | Viscosity mPa · s 24 hrs. |
|---|---|---|---|---|---|---|
| 12A | N | 1.5 | 6.5 | 79.9 | 23,450 | 32,400 |
| 12B | N | 2 | 6.3 | 79.2 | 34,350 | 51,600 |
| 13A | O | 1 | 6.6 | 52.9 | 17,790 | 30,400 |
| 13B | O | 1.5 | 6.6 | 54 | 66,800 | 85,800 |
| 13C | O | 2 | 6.5 | 52.2 | 122,800 | 164,800 |

TABLE 7A

| | HHCR@90% RH | | | | | |
|---|---|---|---|---|---|---|
| Ex. No. | T@ 70% CR | % CR@ T-0.75 | % CR@ T-1.25 | % CR@ T-4 | % CR@ T-8 | % CR@ T-24 |
| 12A | 24 | 100 | 100 | 96 | 96 | 96 |
| 12B | 24 | 100 | 100 | 93 | 93 | 93 |
| 13A | 24 | 100 | 97 | 97 | 97 | 97 |
| 13B | 4 | 96 | 92 | 80 | 50 | 38 |
| 13C | 24 | 100 | 100 | 96 | 96 | 96 |

Table 7 shows that, at the same active polymer concentration, Polymer O provided hair setting gels with greater viscosities than Polymer N. Compositions containing Polymer N also gave the hair a softer feel than compositions containing Polymer O. Excellent sustained HHCR hair setting efficacy was provided by all the Examples.

EXAMPLES 14–15

Aqueous Hair Setting Compositions

Examples 14–15 illustrate the rheology modification and % clarity in aqueous hair setting compositions containing 1, 1.2 or 1.5 active weight percent of ASAP, Polymer AB (Ex. 14A, 14B, 14C) or Polymer AM (Ex. 15A, 15B, 15C) of Example 1, and the HHCR hair setting efficacy of the compositions. Polymers AB and AM each have three different associative monomers, two of which have linear alkyl hydrophobic end groups and one of which has a carbocyclic alkyl hydrophobic end group. The polymers have the same type of semihydrophobic monomer and different types of crosslinking monomers.

The compositions were prepared by diluting the product emulsion with water to provide the active polymer weight % indicated, employing the formulation shown in Table 8.

TABLE 8

| Ingredient | Wt % |
|---|---|
| Polymer, as indicated in Table 9 | 1–1.5 |
| Propylene glycol | 0.5 |
| Metal ion Chelating Agent | 0.1 |
| Preservative | 0.5 |
| AMP to pH indicated below | q.s. |
| Deionized Water to 100% | q.s. | q.s. = Quantity sufficient to meet the requirement

The viscosity was measured by Method A, the % clarity was obtained by Method B, and HHCR hair setting efficacy was determined by Method F. The results are shown in Table 9.

TABLE 9

| | Polymer AB | | | Polymer AM | | |
|---|---|---|---|---|---|---|
| | Ex. 14A | Ex. 14B | Ex. 14C | Ex. 15A | Ex. 15B | Ex. 15C |
| Polymer % (active) | 1 | 1.2 | 1.5 | 1 | 1.2 | 1.5 |
| pH | 6.7 | 6.5 | 6.5 | 6.8 | 6.7 | 6.7 |
| % Clarity | 78.1 | 77.2 | 76.3 | 86.8 | 83.8 | 81.2 |
| Viscosity (mPa · s) | | | | | | |
| Immediate | 2,620 | 4,740 | 13,460 | 13,300 | 21,150 | 39,550 |
| 24 hour | 5,500 | 7,400 | 16,650 | 15,500 | 30,800 | 39,800 |
| HCCR @90% RH | | | | | | |
| T@70% CR | 24 | 24 | 24 | 1.75 | 24 | 24 |
| % CR@T-0.75 | 96 | 100 | 100 | 91 | 100 | 100 |

TABLE 9-continued

|  | Polymer AB | | | Polymer AM | | |
| --- | --- | --- | --- | --- | --- | --- |
|  | Ex. 14A | Ex. 14B | Ex. 14C | Ex. 15A | Ex. 15B | Ex. 15C |
| % CR@T-1.25 | 96 | 100 | 100 | 87 | 100 | 100 |
| % CR@T-4 | 96 | 100 | 100 | 64 | 100 | 97 |
| % CR@T-8 | 96 | 100 | 100 | 60 | 100 | 89 |
| % CR@T-24 | 96 | 100 | 96 | 60 | 96 | 77 |

At the same active polymer concentration, Polymer AM provided hair setting gels with greater viscosity than Polymer AB. Very good clarity and very good (Ex. 15A) to excellent (Exs. 14A, 14B, 14C, 15B, 15C) sustained HHCR hair setting efficacy was provided.

EXAMPLES 16–28

Aqueous Hair Setting Gels

The procedure of Examples 2–8 was followed, except that the polymers employed were crosslinked ASAP, Polymers E (Exs. 16A,B), F (Exs. 17A,B), H (Exs. 19A–C), J (Exs. 21A,B), K (Exs. 22A,B), L (Exs. 23A,B), M (Exs. 24A–C), AT (Exs. 25A–D), AU (Exs. 26A–C), AV (Exs. 27A,B), AW (Exs. 28A,B) and non-crosslinked ASAP, Polymers G (Exs. 18A–C) and I (Exs. 20A,B) at various active weight % concentrations as indicated in Table 10 below. Crosslinked Polymers H and J and non-crosslinked Polymers G and I contain chain transfer agents. Polymer M contains two crosslinking agents, one of which is ethoxylated. Polymers AT, AU, AV and AW contain semihydrophobic monomer.

TABLE 10

| Ex. No. | Poly. No. | Wt % polymer | pH | % Clarity | Viscosity mPa · s Immed. | Viscosity mPa · s 24 hr |
| --- | --- | --- | --- | --- | --- | --- |
| 16A | E | 1.5 | 6.8 | 65 | 73,200 | 109,800 |
| 16B | E | 1.8 | 6.8 | 64.7 | 120,800 | 144,600 |
| 17A | F | 1.5 | 6.5 | 69.2 | 49,800 | 94,800 |
| 17B | F | 1.8 | 6.4 | 68.7 | 73,400 | 117,600 |
| 18A | G | 1.5 | 6.4 | 92.1 | 27,550 | 34,000 |
| 18B | G | 1.8 | 6.3 | 91.8 | 27,350 | 36,200 |
| 18C | G | 2 | 6.3 | 91 | 45,650 | 66,800 |
| 19A | H | 1.5 | 6.3 | 95.9 | 30,950 | 37,200 |
| 19B | H | 1.8 | 6.3 | 94.2 | 46,450 | 57,800 |
| 19C | H | 2 | 6.4 | 94 | 79,800 | 86,600 |
| 20A | I | 1 | 6.4 | 96.5 | 23,800 | 35,050 |
| 20B | I | 1.2 | 6.2 | 95 | 42,600 | 79,200 |
| 21A | J | 1 | 6.2 | 94.6 | 19,600 | 25,850 |
| 21B | J | 1.2 | 6.1 | 97 | 35,900 | 68,200 |
| 22A | K | 1.5 | 6.6 | 75.2 | 65,200 | 96,200 |
| 22B | K | 1.8 | 6.6 | 70.3 | 103,200 | 136,200 |
| 23A | L | 1.5 | 7 | 83.3 | 58,200 | 97,200 |
| 23B | L | 1.8 | 7.1 | 79.9 | 136,600 | 164,800 |
| 24A | M | 1.5 | 6.6 | 60.3 | 39,600 | 56,200 |
| 24B | M | 1.8 | 6.6 | 55.9 | 49,400 | 84,600 |
| 24C | M | 2 | 6.7 | 48.7 | 93,600 | 119,400 |
| 25A | AT | 1 | 6.5 | 86.2 | 9,700 | 11,200 |
| 25B | AT | 1.2 | 6.5 | 84.3 | 13,850 | 14,000 |
| 25C | AT | 1.5 | 6.5 | 82.5 | 36,200 | 44,400 |
| 25D | AT | 2 | 6.5 | 85.8 | 71,600 | 78,200 |
| 26A | AU | 1 | 6.3 | 89.1 | 6,720 | 7,850 |
| 26B | AU | 1.2 | 6.3 | 87.2 | 8,100 | 9,300 |
| 26C | AU | 1.5 | 6.2 | 86.6 | 12,400 | 13,050 |
| 27A | AV | 1.5 | 6.5 | 92.3 | — | 23,200 |
| 27B | AV | 2 | 6.5 | 93.6 | — | 50,000 |
| 28A | AW | 1.5 | 6.5 | 86.2 | — | 18,500 |
| 28B | AW | 2 | 6.5 | 97.6 | — | 32,700 |

The results in Table 10 show that the viscosities of all the aqueous hair setting gels containing Polymers E-M (Exs. 16–24) underwent a substantial increase as these aqueous compositions age over 24 hours or so. Polymers G, H, I, J and K demonstrated a surprisingly enhanced clarity and viscosity, greater than even that of Polymers E, F, L and M at similar concentration. Surprisingly, Polymers AT-AU provided viscosities that were substantially unchanged over 24 hours or so. Polymers AT-AW were judged suitable for either high viscosity or gel hair setting compositions.

The HHCR hair setting efficacy of the compositions of Exs. 16–24 is shown in Table 10A.

TABLE 10A

| | HHCR@90% RH | | | | | |
| --- | --- | --- | --- | --- | --- | --- |
| Ex. No. | T@ 70% CR | % CR@ T-0.75 | % CR@ T-1.25 | % CR@ T-4 | % CR@ T-8 | % CR@ T-24 |
| 16A | 7 | 90 | 90 | 73 | 66 | 60 |
| 16B | 24 | 100 | 96 | 96 | 96 | 96 |
| 17A | 24 | 100 | 93 | 80 | 73 | 73 |
| 17B | 24 | 96 | 96 | 93 | 93 | 90 |
| 18A | 5 | 89 | 85 | 74 | 66 | 66 |
| 18B | 24 | 100 | 100 | 100 | 96 | 96 |
| 18C | 24 | 100 | 100 | 100 | 96 | 96 |
| 19A | 2 | 92 | 92 | 67 | 63 | 59 |
| 19B | 24 | 100 | 100 | 97 | 97 | 97 |
| 19C | 24 | 100 | 96 | 84 | 80 | 76 |
| 20A | 24 | 100 | 97 | 93 | 93 | 93 |
| 20B | 24 | 100 | 100 | 96 | 96 | 96 |
| 21A | 24 | 100 | 96 | 96 | 96 | 96 |
| 21B | 24 | 96 | 96 | 96 | 92 | 92 |
| 22A | 24 | 100 | 100 | 100 | 100 | 100 |
| 22B | 24 | 100 | 97 | 97 | 97 | 97 |
| 23A | 24 | 100 | 97 | 93 | 86 | 82 |
| 23B | 24 | 100 | 100 | 97 | 93 | 93 |
| 24A | 24 | 100 | 100 | 100 | 100 | 100 |
| 24B | 24 | 100 | 100 | 100 | 96 | 96 |
| 24C | 24 | 100 | 96 | 100 | 92 | 92 |

The results in Table 10A show that hair setting efficacy of the compositions of Exs. 16–24 was very good to excellent. The hair setting compositions were judged to be suitable as "medium-firm hold" at polymer concentrations of about 1 to about 1.2% and judged as "firm hold" at concentrations of about 1.5 to about 2%, based on the subjective properties of the treated hair after the compositions had dried on the hair.

The hair setting efficacy of the compositions of Exs. 25–28 was excellent (T@70% CR≧8).

EXAMPLES 29–35

Aqueous Hair Setting Gels

These examples demonstrate the use of ASAP, Polymer AT of Example 1, in combination with commercial hydrophobically modified carbomer polymer, CARBOPOL® Ultrez 21 polymer or CARBOPOL® ETD 2020 polymer (both available from Noveon, Inc., Cleveland Ohio) in beneficially achieving hair setting gels having an unexpected increase in viscosity while maintaining and enhancing the desirable aesthetic, electrolyte (salt) tolerance, and gel pick-up product properties associated with hair setting gels produced with such commercially available polymer.

Aqueous hair setting gels were prepared containing the varying amounts of each polymer shown in Table 11 below. The hair setting gels were prepared by adding the commercial polymer to a portion of the water content, pre-dispersing the polymer by admixing with stirring for about 15 minutes, avoiding entraining air, and allowing the admixture to stand without stirring for about 30 minutes to provide a polymer dispersion. The requisite amount of aqueous Polymer AT emulsion was then admixed into the foregoing polymer dispersion and sufficient AMP (95%) was added to the polymeric mixture to adjust the pH to a range of about 6.4–6.8 to form a gel.

One series of hair setting gels was prepared containing, on a composition weight basis, either a total polymer content of about 1.25 active weight % ASAP, alone (Control 1), commercial polymer alone (Control 2), or comprised of varying combinations of ASAP and commercial polymer (Exs. 29, 29A, 30, 30A, 31, and 32). A second similar series of gels were prepared, except that the total polymer content was about 1 active weight % (Control 3, Control 4, Control 5, Exs. 33, 34, 34A, and 35).

The viscosity of each hair setting gel was determined by Method A. Gel pick-up was subjectively evaluated by hand dipping several fingers into the gel to scoop out a dollop of product to simulate actual usage of a hair setting gel and observing the cushioning properties of the hair setting gel that adheres to the fingers. The term "cushioning" refers generally to the firmness of a gel and the ability of a dollop of gel to adhere to the fingers and hold a firm peak (i.e., a peaking gel). Gel pick-up was subjectively rated on the basis of observed cushioning as follows: excellent=pronounced and sustained peak, very good=medium and sustained peak, good=slight to medium peak, marginal=slight peak, and weak=no peak, smooth. Gel pick-up is a desirable sensory product attribute that a consumer expects when the user physically scoops up an amount of hair setting gel from a jar with the fingers or squeezes the hair setting gel out of a tube onto the fingers for application to the hair. The results of the viscosity and gel pick-up evaluations are shown in Table 11.

TABLE 11

| Example No. | Weight % Polymer AT, (Ex. 1) | Weight % Commercial Polymer (*) CARBOPOL ® Ultrez 21 (**) CARBOPOL ® ETD 2020 | Brookfield Viscosity (mPa · s) | Gel Pick-Up |
| --- | --- | --- | --- | --- |
| Control 1 | 1.25 | — | 21,200 | Weak |
| 29 | 1 | 0.25* | 60,400 | Good |
| 30 | 0.75 | 0.5* | 97,600 | Very Good |
| 31 | 0.5 | 0.75* | 125,000 | Excellent |
| 32 | 0.25 | 1* | 125,000 | Excellent |
| Control 2 | — | 1.25* | 93,600 | Excellent |
| Control 3 | 1 | — | 11,400 | Marginal |
| 33 | 0.75 | 0.25* | 21,800 | Good |
| 34 | 0.5 | 0.5* | 67,200 | Very Good |
| 35 | 0.25 | 0.75* | 93,800 | Excellent |
| Control 4 | — | 1* | 76,600 | Excellent |
| Control 5 | — | 1** | 44,200 | Excellent |
| 34A | 0.5 | 0.5** | 53,200 | Good |

TABLE 11-continued

| Example No. | Weight % Polymer AT, (Ex. 1) | Weight % Commercial Polymer (*) CARBOPOL ® Ultrez 21 (**) CARBOPOL ® ETD 2020 | Brookfield Viscosity (mPa · s) | Gel Pick-Up |
| --- | --- | --- | --- | --- |
| 30A | 0.75 | 0.5** | 79,000 | Excellent |
| 29A | 1 | 0.25** | 53,400 | Excellent |

The results show an unexpected increase in viscosity was achieved at a total polymer content of about 1.25 weight % when the weight ratio of ASAP: commercial polymer was about 3:2 (Exs. 30, 30A), 2:3 (Ex. 31) and 1:4 (Ex. 32). At a total polymer content of about 1 weight %, an unexpected increase in viscosity was achieved when the weight ratio of ASAP: commercial polymer was about 1:3 (Ex. 34).

The gel pick-up of all the ASAP/commercial polymer combinations was judged good to excellent, indicating compatibility.

EXAMPLE 36

Aqueous Hair Setting Compositions

This example illustrates the hair setting efficacy of ASAP at varying concentrations. Five aqueous hair setting compositions were separately prepared each containing, on a total composition weight basis, Polymer AT of Example 1, at a concentration of respectively about 0.2 active weight % (Ex. 36A); about 0.4 active weight % (Ex. 36B); about 0.6 active weight % (Ex. 36C); about 0.8 weight % (Ex. 36D) and about 1 weight % (Ex. 36E), and sufficient AMP (95) to obtain a pH in the range of about 6.6–7.2. The Brookfield viscosity (Method A), % clarity (Method B) and hair setting efficacy (HHCR, Method F) was determined for each composition.

All of the hair setting compositions were clear (% clarity was in the range of about 72 to about 83). The Brookfield viscosity of hair setting compositions ranged from thin for Exs. 36A and 36B (about 15 mPa·s and about 220 mPa·s respectively), to medium for Ex. 36C (about 1,330 mPa·s), to high for Exs. 36D and 36E (about 3,880 mPa·s and about 9,750 mPa·s, respectively). All the hair setting compositions, except Ex. 36A, had excellent HHCR efficacy (T@70CR of >8 hours). The hair setting efficacy of the composition of Ex. 36A was substantially temporary (T@?70CR of 0.25 hours).

EXAMPLE 37

Comparative Hair Setting Gels

This comparative example illustrates the rheology, clarity and hair setting efficacy of conventional hair setting compositions containing either PVP (Ex. 37A) or PVP/VA (Ex. 37B) and a carbomer gellant in the activity weight % amounts indicated in Table 12. The viscosity was measured by Method A, the % clarity was obtained by Method B. The hair setting efficacy was determined by Method F, and the subjective properties were rated as described in Method G, as shown in Table 12A.

TABLE 12

| Ingredient | Ex. 37A Weight % | Ex. 37B Weight % |
|---|---|---|
| PVP | 3 | — |
| PVP/VA | — | 3 |
| Carbomer (Note 1) | 0.5 | 0.5 |
| AMP (95%) to pH | q.s. | q.s. |
| Deionized water to 100% | q.s. | q.s. |
| pH | 6.2 | 6 |
| % Clarity | 79.5 | 92.5 |
| Viscosity, mPa · s | | |
| Immediate | 36,800 | 27,100 |
| 24-hours | 57,800 | 38,000 |

Note 1.
CARBOPOL ® 980 polymer, Noveon, Inc.

TABLE 12A

| HHCR @ 90% RH | Ex. 37A | Ex. 37B |
|---|---|---|
| T @ 70% CR | 1.25 | 0.5 |
| CR @ T-0.75 | 92 | 24 |
| CR @ T-1.25 | 76 | 8 |
| CR @ T-1.75 | 36 | 8 |
| Subjective Property Rating | | |
| Spreadability | 4 | 4 |
| Feel | 4 | 4 |
| Combing | 4 | 4 |
| Curl Memory | 0 | 0 |
| Residue | 4 | 3 |

The data in Table 12A show that PVP afforded very good hair setting efficacy for about 1.25 hours and then weakened rapidly within a half hour thereafter; whereas the hair setting efficacy provided by PVP/VA was weak within 0.75 hours. The product compositions had good spreadability and feel characteristics and the treated hair had good combing characteristics. Some residue was noted, however, and the hair had no curl memory.

EXAMPLES 38–40

Aqueous Hair Setting Formulations

The procedure of Examples 14–15 were followed, except that ASAP, Polymer P (Ex 38A, 38B, 38C), Polymer Q (Ex. 39A, 39B, 39C), and Polymer R (Ex. 40A, 40B, 40C) of Example 1, were employed in the amounts shown in Table 13. Each of Polymers P, Q, and R has the same two associative monomers and crosslinker; and Polymers Q and R also contain different semihydrophobic monomers.

Additionally, the hair setting gel texture was assessed by spreading a portion of the gel or viscous formulation over a MYLAR® film substrate employing a 10 mil opening draw down applicator and observing its smoothness and spreadability characteristic. When the texture of the gel coating was smooth and spreadable, it was rated as "S"; when the gel coating appeared grainy, it was rated as "G". The viscosity and % clarity obtained by Methods A and B, respectively, are shown in Table 13 below, and the HHCR hair setting efficacy of the compositions obtained by Method F is shown in Table 13A.

TABLE 13

| Ex. No. | Poly. No. | Wt % Poly. | pH | % Clarity | Visc. mPa · s Immed. | Visc. mPa · s 24 hrs. | Gel Texture |
|---|---|---|---|---|---|---|---|
| 38A | P | 1 | 6.8 | 88.2 | 13,500 | 14,800 | S |
| 38B | P | 1.2 | 6.8 | 84.6 | 24,500 | 26,750 | S |
| 38C | P | 1.5 | 6.8 | 81.7 | 39,750 | 42,500 | G |
| 39A | Q | 1 | 6.8 | 71.8 | 8,800 | 9,200 | S |
| 39B | Q | 1.2 | 6.8 | 63.6 | 13,750 | 13,500 | S |
| 39C | Q | 1.5 | 6.9 | 65 | 26,250 | 27,000 | S |
| 40A | R | 1 | 6.9 | 94.9 | 9,500 | 10,000 | S |
| 40B | R | 1.2 | 6.9 | 92.8 | 19,500 | 19,500 | S |
| 40C | R | 1.5 | 6.8 | 93.8 | 27,250 | 29,000 | S |

TABLE 13A

HHCR@90% RH

| Ex. No. | T@ 70% CR | % CR@ T-0.75 | % CR@ T-1.25 | % CR@ T-4 | % CR@ T-8 | % CR@ T-24 |
|---|---|---|---|---|---|---|
| 38A | 7 | 96 | 96 | 92 | 68 | 52 |
| 38B | 8 | 100 | 100 | 96 | 74 | 57 |
| 38C | 8 | 100 | 100 | 96 | 92 | 42 |
| 39A | 24 | 100 | 100 | 92 | 92 | 92 |
| 39B | 24 | 100 | 100 | 96 | 88 | 76 |
| 39C | 24 | 96 | 96 | 96 | 96 | 96 |
| 40A | 24 | 96 | 96 | 92 | 75 | 71 |
| 40B | 3 | 92 | 92 | 67 | 55 | 38 |
| 40C | 8 | 100 | 96 | 92 | 80 | 64 |

As shown in Table 13, all the polymers produced "S" gel textures, except for the crosslinked Polymer P at 1.5% (Ex. 38C). The texture of the gels obtained with Polymers Q and R, which contain a semihydrophobic monomer, were judged to be soft, smooth, and spreadable, even as the concentration of the polymer increased, compared to the texture of the gels obtained with Polymer P, containing no semihydrophobic monomer which had a "G" texture at 1.5% concentration. All compositions had good clarity and viscosity.

As shown in Table 13A, at all concentrations, Polymers P, Q and R demonstrated excellent hair setting efficacy.

EXAMPLE 41–44

Aqueous Hair Setting Formulations

In Examples 41–44, the procedure of Examples 38–40 was followed, except that the RMHS polymers employed were ASAP, Polymers AF (Ex. 41A, B), AG (Ex. 42A, B), AH (Ex. 43A, B) and AI (Ex. 44A, B) of Example 1, at the amounts shown in Table 14. The polymers have varying amounts of the same type of semihydrophobic monomer. The viscosity, % clarity and texture results are in Table 14, with the HHCR hair setting efficacy of the compositions shown in Table 14A.

TABLE 14

| Ex. No. | Poly. No. | Wt % Poly. | pH | % Clarity | Visc. mPa · s Immed. | Visc. mPa · s 24 hrs. | Gel Texture |
|---|---|---|---|---|---|---|---|
| 41A | AF | 1 | 7 | 83.6 | 18,600 | 26,650 | S |
| 41B | AF | 1.2 | 6.9 | 82.9 | 23,650 | 34,900 | S |
| 42A | AG | 1 | 6.9 | 67 | 13,550 | 18,350 | S |
| 42B | AG | 1.2 | 6.9 | 65.8 | 21,050 | 32,400 | S |
| 43A | AH | 1 | 7 | 85.5 | 16,700 | 25,450 | S |
| 43B | AH | 1.2 | 6.9 | 86.4 | 22,950 | 36,400 | S |
| 44A | AI | 1 | 6.7 | 93.6 | 16,550 | 23,500 | S |
| 44B | AI | 1.2 | 6.6 | 92.8 | 21,700 | 28,800 | S |

TABLE 14A

| | | HHCR@90% RH | | | |
|---|---|---|---|---|---|
| Ex. No. | T@ 70% CR | % CR@ T-0.75 | % CR@ T-1.25 | % CR@ T-4 | % CR@ T-8 | % CR@ T-24 |

| Ex. No. | T@ 70% CR | % CR@ T-0.75 | % CR@ T-1.25 | % CR@ T-4 | % CR@ T-8 | % CR@ T-24 |
|---|---|---|---|---|---|---|
| 41A | 24 | 96 | 96 | 92 | 88 | 88 |
| 41B | 24 | 100 | 100 | 96 | 96 | 96 |
| 42A | 24 | 92 | 92 | 87 | 87 | 87 |
| 42B | 8 | 96 | 92 | 84 | 80 | 67 |
| 43A | 6 | 96 | 92 | 87 | 61 | 53 |
| 43B | 24 | 96 | 96 | 96 | 92 | 92 |
| 44A | 7 | 96 | 92 | 83 | 66 | 61 |
| 44B | 24 | 100 | 100 | 96 | 92 | 92 |

The data in Tables 14 and 14A show that, at all concentrations, the texture of the gel produced was smooth and spreadable ("S"). Each of the hair setting gels provided excellent, sustained hair setting efficacy. Surprisingly, varying the amount of semihydrophobic monomer from 2.5 weight percent (Polymer AF) up to about 15 weight percent (Polymer AI) had no adverse effect on the rheology modification achieved in the hair setting gels at each polymer concentration.

EXAMPLES 45–50

Aqueous Hair Setting Gels

The procedure of Examples 14–15 was followed except that the ASAP hair setting agents employed were Polymer X (Ex. 45A, 45B, 45C), Polymer Y (Ex. 46A, 46B, 46C), Polymer Z (Ex. 47A, 47B, 47C), Polymer AO (Ex. 48A, 48B), Polymer AP (Ex. 49A, 49B), and Polymer AQ (Ex. 50A, 50B) at the concentrations shown in Table 15. Each of the ASAP contain a semihydrophobic monomer and two associative monomer components; and Polymers AO and AP each also have two nonionic vinyl monomer components.

The % clarity and viscosity are shown in Table 15 and the HHCR hair setting efficacy is shown in Table 15A.

TABLE 15

| Ex. No. | Poly. No. | Wt % Poly. | pH | % Clarity | Visc. mPa · s Immed. | Visc. mPa · s 24 hrs. |
|---|---|---|---|---|---|---|
| 45A | X | 1 | 6.9 | 90.4 | 11,600 | 12,800 |
| 45B | X | 1.2 | 6.9 | 90.9 | 20,000 | 20,500 |
| 45C | X | 1.5 | 6.8 | 88.1 | 38,750 | 38,250 |
| 46A | Y | 1 | 6.8 | 81.4 | 12,800 | 14,100 |
| 46B | Y | 1.2 | 6.9 | 83.3 | 24,750 | 28,500 |
| 46C | Y | 1.5 | 6.8 | 86.3 | 59,000 | 63,000 |
| 47A | Z | 1 | 6.8 | 79 | 7,700 | 7,760 |
| 47B | Z | 1.2 | 6.9 | 78.5 | 15,500 | 14,960 |
| 47C | Z | 1.5 | 6.8 | 78 | 27,500 | 31,350 |
| 48A | AO | 1 | 6.4 | 80.2 | 8,230 | 11,650 |
| 48B | AO | 1.5 | 6.8 | 81.7 | 22,790 | 37,850 |
| 49A | AP | 1 | 6.9 | 89.2 | 9,780 | 14,890 |
| 49B | AP | 1.5 | 6.9 | 88.7 | 20,960 | 38,970 |
| 50A | AQ | 1 | 7 | 78.1 | 9,440 | 13,990 |
| 50B | AQ | 1.5 | 7.2 | 78 | 27,940 | 47,700 |

TABLE 15A

| | | HHCR @ 90% RH | | | | |
|---|---|---|---|---|---|---|
| Ex. No. | T@ 70% CR | % CR@ T-0.75 | % CR@ T-1.25 | % CR@ T-4 | % CR@ T-8 | % CR@ T-24 |
| 45A | 6 | 96 | 96 | 92 | 48 | 35 |
| 45B | 8 | 100 | 100 | 93 | 80 | 39 |
| 45C | 24 | 100 | 100 | 100 | 96 | 96 |
| 46A | 24 | 100 | 100 | 100 | 100 | 84 |
| 46B | 24 | 97 | 97 | 97 | 93 | 74 |
| 46C | 24 | 100 | 100 | 100 | 96 | 84 |
| 47A | 24 | 100 | 97 | 81 | 81 | 74 |
| 47B | 24 | 96 | 96 | 92 | 92 | 92 |
| 47C | 24 | 96 | 96 | 92 | 92 | 92 |
| 48A | 8 | 100 | 100 | 100 | 72 | 44 |
| 48B | 6 | 100 | 96 | 96 | 60 | 32 |
| 49A | 4 | 100 | 100 | 84 | 38 | 25 |
| 49B | 24 | 100 | 100 | 96 | 92 | 92 |
| 50A | 24 | 96 | 92 | 92 | 88 | 84 |
| 50B | 24 | 100 | 100 | 100 | 92 | 88 |

The data show that, at all concentrations, the Polymers provided good clarity, viscosity and excellent, sustained hair setting efficacy.

EXAMPLE 51

Aqueous Silicone Hair Setting Gels

This example illustrates aqueous silicone-containing hair setting gels prepared employing ASAP, Polymer K (Ex. 51A) and Polymer M (Ex. 51 B) of Example 1 in the formulation shown in Table 16, along with hair setting efficacy, determined by Method F.

TABLE 16

| Ingredients | Ex. 51A Weight % | Ex. 51B Weight % |
|---|---|---|
| Polymer | 1 | 1.5 |
| AMP (95%) | To pH 7.4 | To pH 6.4 |
| Dimethicone PEG-7 phthalate (Note 2) | 1.5 | 1 |
| Preservative | q.s. | q.s. |
| Fragrance | q.s. | q.s. |
| Deionized water to 100% | q.s. | q.s. |
| Viscosity (24 hrs.) | 33,000 | 39,200 |
| HHCR@90% RH | | |
| T@70% CR | 24 | 8 |
| CR@T-8 | 80 | 83 |
| CR@T-24 | 70 | 63 |

Note 2.
INCI name for a water-soluble, anionic silicone carboxy compound sold under the trade name ULTRASIL ™ CA-1 by Noveon Inc.

The hair setting efficacy was excellent. The hair treated with the hair setting compositions, based on subjective evaluations, had a natural, moderate crisp feel, was easy to comb, had good curl memory, and no residue or static fly-away was noted on combing.

EXAMPLES 52

Hydro-Alcoholic Fixative Hair Setting Sprays

Example 52 illustrates the use of ASAP, Polymer M of Example 1 at active polymer weight concentrations of about 1.5% (Ex. 52A) and about 2% (Ex. 52B), and Polymer BG of Example 1 at an active polymer weight concentration of about 5% (Ex. 52C) in fixative hair setting spray compositions having a low volatile organic compounds (VOC) content. A hydro-alcoholic solvent system comprising ethanol and water, neutralizing amine (AMP), preservative and fragrance was employed as indicated in Table 17, along with hair setting efficacy, determined by Method F.

TABLE 17

| Ingredients | Ex. 52A Weight % | Ex. 52B Weight % | Ex. 52C Weight % |
|---|---|---|---|
| Polymer M, Ex. 1 | 1.5 | 2 | — |
| Polymer BG, Ex. 1 | — | — | 5 |
| Ethanol, SD 40 | 55 | 55 | 55 |
| AMP (95%) to pH | 6.9 | 6.7 | 7–8 |
| Preservative | q.s. | q.s. | — |
| Deionized water to 100% | q.s. | q.s. | q.s. |
| Fragrance | q.s. | q.s. | — |
| HHCR@ 90% RH | | | |
| T@70% CR | 24 | 24 | >8 |
| CR@T-8 | 100 | 96 | — |
| CR@T-24 | 93 | 90 | — |

The HHCR hair setting efficacy was excellent and curl memory was good. The hair set with Polymer M (Ex. 52A and 52B) was subjectively evaluated and had a natural, moderate crisp feel, was easy to comb, and no residue or static fly-away was observed on combing. The hair sprayed with Polymer BG (Ex. 53C) had no dulling residue and washout of the polymer from the hair was excellent.

The formulations of Exs. 52A, 52B and 52C showed a good, substantially uniform fine spray pattern when dispensed from a manually actuated pump spray and were suitable for use as low VOC (55%) hair sprays.

The low VOC formulation of Ex. 52C was repeated, except that ASAP, Polymer BI (Ex. 52D) of Example 1 was used and the product was dispensed from a mechanical, non-aerosol "instant foamer" unit to provide a thick, glossy and rich hair setting foam. The hair setting efficacy of the Polymer BI foam (Ex. 52D) was excellent (T@70% CR >8 hours), curl memory was good, no dulling residue was noted, and washout from the hair was excellent. The polymers were judged useful for mechanical, non-aerosol foamers and spray systems that do not employ chemical or gaseous propellants.

EXAMPLE 53

Comparative Hair Gels

This comparative example illustrates the HHCR at 90% RH, determined by Method F, of a hair fixative composition containing a commercial neutralizable, polymer having no polyoxyalkylene segment connecting a polymerizable end group with a hydrophobic end group, and thus no associative monomer component as defined herein. The polymer has the INCI name: VP/Acrylates/Lauryl Methacrylate Copolymer, and is sold as a hair fixative polymer by International Specialty Products (ISP), Wayne, N.J. under the trade name STYLEZE™ 2000. This polymer reportedly has a Tg of 150° C. and an acid Number of 160–190 as described by R. Rigoletto, et al, in articles appearing in *Soap & Cosmetics*, 43–46 (July/August 2001) and 39–43, (September 2001), the relevant disclosures of which are incorporated herein by reference. The polymer was evaluated as the sole hair fixative at an active polymer weight of 2% (Ex. 53A), 4% (Ex. 53B) and 6% (Ex. 53C) in water, neutralized with AMP (95%) to the pH indicated in the following table. As a comparison control, a concentrated aqueous gel (Ex. 53D) was similarly prepared containing STYLEZE™ 2000 and ACULYN® 28 as a gellant, each at an active polymer weight of 0.5% as recommended in the literature, and neutralized with AMP to about pH 6.4. The viscosity and clarity were determined by Method A and B, respectively, HHCR hair setting efficacy at 90% RH was determined by Method F and subjective properties were rated by Method G. The results are shown in Table 18.

TABLE 18

| | Ex. 53A | Ex. 53B | Ex. 53C | Ex. 53D |
|---|---|---|---|---|
| Polymer % | 2 | 4 | 6 | 0.5 |
| Thickener % | — | — | — | 0.5 |
| pH | 7.3 | 6.8 | 6.8 | 6.4 |
| % Clarity | 76.5 | 50.2 | 9.8 | 78.4 |
| Viscosity (mPa · s) Immed. | 900 | 35,200 | 104,300 | 20,000 |
| HCCR @ 90% RH | | | | |
| T @ 70% CR | 0.5 | 0.5 | 1.75 | 0.5 |
| % CR @ T-0.75 | 50 | 48 | 92 | 63 |
| % CR @ T-1.75 | 38 | 31 | 80 | 38 |
| % CR @ T-3 | 30 | 31 | 46 | 9 |
| % CR @ T-4 | 25 | 22 | 34 | 9 |
| % CR @ T-24 | 21 | 22 | 21 | 9 |
| Subjective Property Rating | | | | |
| Spreadability | 2 | 1 | 0 | 3 |
| Feel | 4 | 3 | 4 | 3 |
| Combing | 1 | 1 | 1 | 4 |
| Curl Memory | 0 | 0 | 0 | 2 |
| Residue | 5 | 4 | 3 | 4 |

The results show that, at an active polymer concentration of 2% (Ex. 53A), the viscosity of the composition was thin and HHCR weakened rapidly after 0.5 hours as did the control (Ex. 53D). Increasing the active polymer weight concentration to 4% (Ex. 53B) increased the viscosity to a gel, but at the expense of clarity, and subjective properties with no increased benefit in curl retention. Increasing the active polymer weight concentration to 6% (Ex. 53C) further increased the viscosity of the composition significantly which produced very good fixative hair setting efficacy for about 1.75 hours at the expense of clarity and aesthetic subjective properties. Thus, the data demonstrate that the commercial polymer was not suitable as a sole hair fixative and rheology modifier due to the high concentrations required for short-lived efficacy and very poor product clarity at high concentration.

EXAMPLES 54–56

Aqueous Hair Setting Gels

The procedure of Examples 14–15 was followed except that the ASAP hair setting agents employed were Polymer B (Ex. 54A, 54B), Polymer AA (Ex. 55A, 55B) and Polymer AC (Ex. 56A, 56B) each at active polymer weight concentrations of 1% and 1.2%. The Polymers B, AA and AC each comprise two acidic vinyl monomer portions and two associative monomers and Polymer B additionally comprises two nonionic vinyl monomers. Polymers B and AC are also crosslinked. The % clarity and the viscosity are shown in Table 19, and the hair setting efficacy, determined by Method F, is shown in Table 19A.

TABLE 19

| Ex. No. | Poly. No. | Wt % Poly. | pH | % Clarity | Visc. mPa·s Immed. | Visc. mPa·s 24 hrs. |
|---|---|---|---|---|---|---|
| 54A | B | 1 | 6.6 | 51.5 | 6,340 | 11,550 |
| 54B | B | 1.2 | 6.8 | 50.2 | 9,840 | 17,200 |
| 55A | AA | 1 | 6.9 | 66.3 | 4,560 | 11,650 |
| 55B | AA | 1.2 | 6.6 | 63.9 | 7,260 | 17,350 |
| 56A | AC | 1 | 6.3 | 78.8 | 5,000 | 9,100 |
| 56B | AC | 1.2 | 6.2 | 78.1 | 7,200 | 10,850 |

TABLE 19A

HHCR @ 90% RH

| Ex. No. | T@ 70% CR | % CR@ T-0.75 | % CR@ T-1.25 | % CR@ T-4 | % CR@ T-8 | % CR@ T-24 |
|---|---|---|---|---|---|---|
| 54A | 5 | 92 | 92 | 79 | 66 | 53 |
| 54B | 24 | 100 | 96 | 96 | 96 | 96 |
| 55A | 1.25 | 96 | 84 | 34 | 34 | 30 |
| 55B | 1.75 | 96 | 88 | 55 | 38 | 34 |
| 56A | 24 | 96 | 96 | 92 | 92 | 87 |
| 56B | 24 | 96 | 92 | 92 | 92 | 88 |

The data show that each of the polymers were rheology modifying, hair setting agents. Polymer AA (Ex. 55A, 55B) provided very good hair setting efficacy and Polymers B and AC (Ex. 54A, 54B and 56A, 56B respectively) provided excellent hair setting efficacy.

EXAMPLE 57

Aqueous Hair Setting Gels

This example illustrates the use of HASE Polymers as the sole rheology modifying, hair setting agents. HASE Polymers, sold commercially under the trade names ACULYN® 22 (Ex. 57A), ACULYN® 28 (Ex. 57B), STRUCTURE® 2001 (Ex. 57C), STRUCTURE® 3001 (Ex. 57D) and SAL-CARE® SC80 (Ex. 57E) were each employed at an active polymer weight concentration of 1.2% calculated on the basis of the total solids of the product as reported in the literature or by the manufacturer. The hair setting gels were prepared and neutralized to the pH indicated below as described in Examples 2–8. The % clarity value was obtained by Method B, and the viscosity was measured by Method A. The hair setting efficacy was determined by Method F and the subjective properties were rated by Method G. The results are shown in Table 20.

TABLE 20

|  | Ex. 57A | Ex. 57B | Ex. 57C | Ex. 57D | Ex. 57E |
|---|---|---|---|---|---|
| pH | 6.5 | 6.4 | 6.6 | 6.5 | 6.6 |
| % Clarity | 84 | 91 | 93.4 | 90 | 92.3 |
| Viscosity mPa·s |  |  |  |  |  |
| Immed. | 8,600 | 40,500 | 13,200 | 3,950 | 4,700 |
| 24 hour | 10,660 | 79,200 | 20,050 | 5,060 | 5,700 |
| HHCR@90% RH |  |  |  |  |  |
| T@70% CR | 1.25 | 0.75 | 0.75 | 3 | 0.75 |
| % CR@T-0.75 | 97 | 76 | 80 | 96 | 84 |
| % CR@T-1.75 | 81 | 32 | 60 | 92 | 42 |
| % CR@T-3 | 70 | 20 | 56 | 76 | 25 |

TABLE 20-continued

|  | Ex. 57A | Ex. 57B | Ex. 57C | Ex. 57D | Ex. 57E |
|---|---|---|---|---|---|
| % CR@T-7 | 54 | 16 | 24 | 36 | * |
| % CR@T-24 | 39 | 4 | * | 28 | * |
| Subjective Properties Rating |  |  |  |  |  |
| Feel | 3 | 2 | 2 | 2 | 3 |
| Spreadability | 3 | 3 | 4 | 3 | 4 |
| Combing | 3 | 3 | 5 | 3 | 5 |
| Curl Memory | 2 | 2 | 0 | 2 | 0 |
| Residue | 4 | 4 | 5 | 4 | 5 |

* Not measured.

The data show that at the 1.2% concentration, the HASE Polymers provided both rheology modification and varying degrees of hair setting efficacy ranging from good (Ex. 57B, 57C, 57E) to very good (Ex. 57A) to excellent (Ex. 57D) based on the T@70% CR. Hair setting efficacy, however, was judged weaker than that achieved with ASAP hair setting agents.

EXAMPLE 58

Aqueous Hair Setting Gels

The procedure of Example 2–8 was followed, except that the RMHS polymers employed were ASAP, Polymer Y (Ex. 58A) or Polymer Z (Ex. 58B), each at an active polymer weight of about 1.2%. These polymers have two associative monomer portions and the same semihydrophobic monomers. The pH, viscosity, % clarity, and hair setting efficacy determined by Method F, and subjective property ratings, determined by Method G, are shown in Table 21.

TABLE 21

|  | Ex. 58A | Ex. 58B |
|---|---|---|
| pH | 6.6 | 6.6 |
| % Clarity | 87 | 81 |
| Viscosity, mPa·s |  |  |
| Immediate | 19,350 | 8,850 |
| 24 hours | 22,400 | 9,890 |
| HHCR@90% RH |  |  |
| T@70% CR | 24 | 24 |
| % CR@T-0.75 | 96 | 96 |
| % CR@T-1.25 | 96 | 96 |
| % CR@T-4 | 92 | 88 |
| % CR@T-8 | 92 | 88 |
| % CR@T-24 | 92 | 84 |
| Subjective Property Ratings |  |  |
| Feel | 5 | 5 |
| Spreadability | 5 | 5 |
| Combing | 4 | 4 |
| Curl Memory | 3 | 3 |
| Residue | 5 | 5 |

The data show that, at 1.2%, the ASAP RMHS polymers, Polymers Y (Ex. 58A) and Z (Ex. 58B), each provided excellent and sustained hair setting efficacy, good viscosity, excellent clarity and aesthetically desirable subjective properties.

EXAMPLE 59

Aqueous Conditioning Hair Setting Gels

This example illustrates the use of ASAP and HASE Polymers as the rheology modifying and sole hair setting polymer at an active polymer weight of about 1.5% in a conditioning formulation, compared to a conventional fixative polymer, PVP/VA (Ex. 59A), at the same concentration. The RMHS polymers employed were ASAP of Example 1, Polymer Y (Ex. 59B), Polymer Z (Ex. 59C) and Polymer AR (Ex. 59F), and two commercial HASE polymers, SYNTHALEN® W2000 (Ex. 59D), and SALCARE® SC80 (Ex. 59E). The composition containing PVP/VA included a carbomer gellant (CARBOPOL® 980 polymer, Noveon, Inc.). The formulation employed is shown in Table 22 and the pH of the compositions was adjusted to a substantially neutral range of about pH 6.5–7 as indicated.

The compositions were prepared by admixing the ingredients of Phase A for about 15 minutes or until the mix was homogenous. The ingredients of Phase B were premixed and then added to Phase A, and stir mixed therein for about 15 minutes or until the mixture was homogeneous. The ingredients of Phase C were premixed and then added to the foregoing mixture and stir mixed for about 15 minutes or until a homogenous stock solution was obtained. The ingredients of Phase D were premixed, employing a sufficient acid-neutralizing amount of triethanolamine (TEA), and the alkaline premix was then added to the stock solution and mixed therein for about 15–30 minutes. The pH was then checked and adjusted, if necessary, with additional TEA, to the desired pH.

The hair setting efficacy, determined by Method F, and subjective property ratings, determined by Method G, are shown in Table 22A.

TABLE 22

| | Weight % (active) | | | | | |
|---|---|---|---|---|---|---|
| Ingredient INCI/Trade Name | Ex. 59A | Ex. 59B | Ex. 59C | Ex. 59D | Ex. 59E | Ex. 59F |
| Phase A | | | | | | |
| Deionized water to 100% | q.s. | q.s. | q.s. | q.s. | q.s. | q.s. |
| Carbomer (Note 1, Ex. 57) | 0.5 | — | — | — | — | — |
| PVP/VA | 1.5 | — | — | — | — | — |
| Polymer Y, Ex. 1 | — | 1.5 | — | — | — | — |
| Polymer Z, Ex. 1 | — | — | 1.5 | — | — | — |
| SYNTHALEN® W2000 | — | — | — | 1.5 | — | — |
| SALCARE® SC80 | — | — | — | — | 1.5 | — |
| Polymer AR, Ex. 1 | — | — | — | — | — | 1.5 |
| Phase B | | | | | | |
| Panthenol | 0.1 | 0.1 | 0.1 | 0.1 | 0.1 | 0.1 |
| Propylene glycol | 0.3 | 0.3 | 0.3 | 0.3 | 0.3 | 0.3 |
| Phase C | | | | | | |
| Oleth-20 | 0.2 | 0.2 | 0.2 | 0.2 | 0.2 | — |
| Fragrance | 0.1 | 0.1 | 0.1 | 0.1 | 0.1 | — |
| Dimethicone copolyol | 0.1 | 0.1 | 0.1 | 0.1 | 0.1 | 0.1 |
| Hydrolyzed wheat protein | 0.05 | 0.05 | 0.05 | 0.05 | 0.05 | 0.05 |
| Part D | | | | | | |
| Preservative | q.s. | q.s. | q.s. | q.s. | q.s. | q.s. |
| TEA to pH indicated | q.s. | q.s. | q.s. | q.s. | q.s. | q.s. |
| pH | 6.9 | 6.6 | 6.7 | 6.8 | 6.9 | 6.2 |
| Viscosity mPa · s | | | | | | |
| Immed. | 39,600 | 65,800 | 45,400 | 67,400 | 34,200 | 16,050 |
| 24 hours | 39,600 | 74,800 | 57,800 | 87,200 | 40,600 | 17,600 |

TABLE 22A

| | Ex. 59A | Ex. 59B | Ex. 59C | Ex. 59D | Ex. 59E | Ex. 59F |
|---|---|---|---|---|---|---|
| HHCR@90% RH | | | | | | |
| T@70% CR | 0.5 | 24 | 3 | 0.75 | 0.75 | 24 |
| % CR@T-0.5 | 82 | 100 | 96 | 88 | 89 | 100 |
| % CR@T-0.75 | 69 | 96 | 92 | 80 | 85 | 100 |
| % CR@T-1.25 | 23 | 96 | 92 | 63 | 47 | 100 |
| % CR@T-3 | 23 | 92 | 84 | 55 | 35 | 100 |
| % CR@T-8 | 23 | 87 | 34 | 38 | 23 | 100 |
| % CR@T-24 | 23 | 83 | 25 | 25 | 20 | 100 |
| Subjective Property Rating | | | | | | |
| Feel | 4 | 5 | 5 | 3 | 3 | — |
| Spreadability | 4 | 5 | 5 | 4 | 4 | — |
| Combing | 4 | 5 | 5 | 3 | 3 | — |
| Curl Memory | 1 | 4 | 4 | 2 | 2 | — |
| Residue | 0 | 0 | 0 | 0 | 0 | — |

The ASAP, Polymer AR (Ex. 59F) provided excellent, sustained hair setting efficacy up to 24 hours, and a lustrous sheen, Polymer Y (Ex. 59B) and Polymer Z (Ex. 59C) provided excellent hair setting efficacy for at least three hours or longer (Ex. 59B). Two of the HASE polymers (Ex.

59D, Ex. 59E) provided good hair setting efficacy for at least 0.75 hours and were more effective than PVP/VA (Ex. 59A) for up to about three hours (Ex. 59E).

In a further evaluation, aqueous hair setting gels of Ex. 59D and 59E in Table 22 were also similarly prepared, except that the active polymer weight was about 1.2% and Phase B contained propylene glycol, glycerin, and hydrolyzed wheat protein, each at a weight of about 0.1%, and all the ingredients of Part D. A similar aqueous hair setting gel was prepared with ASAP, Polymer Z, at about 1.2% active polymer weight. All these aqueous gels had a pH of about 6.7, a % clarity (Method B) in the range of about 91–95% and a viscosity in the range of about 10,000 mPa·s to 38,000 mPa·s. The specular gloss values of these three gels was determined by Method D. At an angle of 20°, the gloss values were in the range of about 40 to about 45 units, and at an angle of 60°, the gloss values were in the range of about 86 to about 95 units. The gels were judged suitable for hair setting and styling maintenance.

EXAMPLE 60

Aqueous Silicone Hair Setting Gels

This example illustrates the use of ASAP RMHS polymers of Example 1, Polymers Q (Ex. 60A), Y— (Ex. 60B) and Z (Ex. 60C) of Example 1, in aqueous silicone-containing hair setting gels employing an active polymer weight of about 1.5% in the formulation shown in Table 23.

TABLE 23

| Ingredient | Weight % |
| --- | --- |
| Polymer, as indicated in Table 24 | 1.5 |
| Deionized Water to 100% | q.s. |
| Solubilized fragrance | q.s. |
| Dimethicone PEG-7 phthalate (Note 2, Table 16) | 0.3 |
| UV Stabilizer | q.s. |
| Preservative | q.s. |
| AMP to pH as indicated in Table 24 | q.s. |

The viscosity, determined by Method A, % clarity determined by Method B and hair setting efficacy results determined by Method —F are shown in Table 24.

TABLE 24

|  | Ex. 60A (Polymer Q) | Ex. 60B (Polymer Y) | Ex. 60C (Polymer Z) |
| --- | --- | --- | --- |
| pH | 6.9 | 7.1 | 7 |
| Immed. Visc. mPa · s | 59,800 | 77,800 | 58,000 |
| 24 Hr. Visc., mPa · s | 60,200 | 77,900 | 58,200 |
| % Clarity | 62.9 | 76.2 | 75.4 |
| HHCR@90% RH | | | |
| T@70% CR | 1.75 | 24 | 24 |
| % CR@T-0.75 | 92 | 100 | 100 |
| % CR@T-1.25 | 80 | 100 | 100 |
| % CR@T-4 | 60 | 100 | 100 |
| % CR@T-8 | 56 | 96 | 100 |
| % CR@T-24 | 56 | 96 | 100 |

The data show that Polymer Q (Ex. 60A) provided very good, long-lasting hair setting efficacy and Polymers Y (Ex. 60B) and Z (Ex. 60C) each provided excellent, sustained hair setting efficacy. All of the polymers provided very good viscosity and good clarity.

EXAMPLE 61

Aqueous Hair Conditioning Gels

This example illustrates the use of ASAP RMHS polymers of Example 1, Polymers Q (Ex. 61A), Y (Ex. 61B) and Z (Ex. 61C), each at an active polymer weight of about 1.2% in aqueous gels containing a cationic conditioning agent employing the following hair setting formulation (Table 25).

TABLE 25

| Ingredient | Weight % |
| --- | --- |
| Polymer, as indicated in Table 26 | 1.2 |
| Deionized Water to 100% | q.s. |
| Panthenol | 0.1 |
| Solubilized fragrance | q.s. |
| Polyquaternium-11 (Note 3) | 0.1 |
| Preservative | q.s. |
| AMP to pH indicated in Table 26 | q.s. |

Note 3.
INCI name for quaternized vinyl pyrrolidone/dimethylaminoethyl methacrylate copolymer, neutralized (GAFQUAT ® 755N, ISP).

The viscosity determined by Method A, % clarity determined by Method B, and hair setting efficacy determined by Method F are shown in Table 26.

TABLE 26

|  | Ex. 61A (Polymer Q) | Ex. 61B (Polymer Y) | Ex. 61C (Polymer Z) |
| --- | --- | --- | --- |
| pH | 7.1 | 7.1 | 7.1 |
| Immed. Visc. mPa · s | 41,200 | 37,800 | 48,200 |
| 24 Hr. Visc., mPa · s | 38,100 | 38,400 | 79,000 |
| % Clarity | 60.5 | 72 | 71.8 |
| HHCR@90% RH | | | |
| T@70% CR | 8 | 1.75 | 24 |
| % CR@T-0.75 | 96 | 88 | 100 |
| % CR@T-1.25 | 96 | 80 | 100 |
| % CR@T-4 | 82 | 42 | 100 |
| % CR@T-8 | 73 | 42 | 100 |
| % CR@T-24 | 64 | 38 | 96 |

The data show that Polymer Y (Ex. 61B) provided very good hair setting efficacy and Polymers Q and Z each provided excellent, sustained hair setting efficacy. All the polymers provided very good viscosity and good clarity.

EXAMPLE 62

Clear Aqueous Hair Spray

This example illustrates the use of ASAP RMHS polymers of Example 1, Polymers A (Ex. 62A), C (Ex. 62B), and Y (Ex. 62C), of Example 1, at an active polymer weight of about 0.8% in clear aqueous hair spray employing the formulation shown in Table 27.

TABLE 27

| Ingredient | Weight % |
| --- | --- |
| Polymer, as indicated in Table 28 | 0.8 |
| Triethanolamine to pH indicated in Table 28 | q.s. |
| Glycerin | 2 |

TABLE 27-continued

| Ingredient | Weight % |
|---|---|
| Preservative | q.s. |
| Metal ion chelating agent | q.s. |
| Deionized Water to 100% | q.s. |

The viscosity determined by Method A, % clarity determined by Method B and hair setting efficacy determined by Method F are shown in Table 28.

TABLE 28

|  | Ex. 62A (Polymer A) | Ex. 62B (Polymer C) | Ex. 62C (Polymer Y) |
|---|---|---|---|
| pH | 6.8 | 7 | 6.5 |
| Immed. Visc. mPa · s | 7,520 | 7,800 | 2,940 |
| 24 Hr. Visc., mPa · s | 9,440 | 8,040 | 4,600 |
| % Clarity | 73 | 69 | 82 |
| HHCR@90% RH | | | |
| T@70% CR | 8 | 5 | 6 |
| % CR@T-0.75 | 100 | 96 | 100 |
| % CR@T-1.25 | 100 | 96 | 96 |
| % CR@T-4 | 100 | 96 | 92 |
| % CR@T-8 | 96 | 25 | 46 |
| % CR@T-24 | 64 | 25 | 25 |

The data show that the hair setting efficacy of all the polymers was excellent, and good viscosity and clarity was achieved.

EXAMPLES 63

Clear Aqueous Hair Spray

This comparative example illustrates the use of the HASE Polymer, commercialized under the trade name, SYNTHALEN® W2000 (Ex. 63A), employed as the sole fixative hair setting agent, at an active polymer weight of about 1.2% in the formulation shown in Table 29. For comparison, PVP/VA (Ex. 63B) was employed in the same formulation, except that a relatively high concentration of about 8% was employed and a carbomer gellant was also included, as indicated in Table 29.

The composition for Ex. 63A was prepared by premixing the preservative and glycerin and adding the premix to about one-third of the water content (Phase A). Separately, the hair setting polymer, and chelating agent were dissolved in the remaining water and triethanolamine (TEA) was added to the polymer solution to neutralize the polymer to about pH 6 or until clear (Phase B). Phase B was then admixed with Phase A, and the pH of the mixture was further adjusted with TEA, if necessary. The composition for Ex. 63B was prepared by following the same procedure, except that the carbomer gellant was dissolved in the water of Phase A, prior to the addition of the premix.

The viscosity determined by Method A, % clarity determined by Method B, hair setting efficacy determined by Method F and subjective property assessment ratings determined by Method G are shown in Table 29.

TABLE 29

|  | Weight % | |
|---|---|---|
| Ingredient | Ex. 63A | Ex. 63 B |
| SYNTHALEN ® W2000 | 1.2 | — |
| PVP/VA | — | 8 |
| Carbomer (Note 4) | — | 0.3 |
| TEA to pH indicated | q.s. | q.s. |
| pH | 6.1 | 5.4 |
| Glycerin | 2 | 2 |
| Preservative | q.s. | q.s. |
| Metal ion chelating agent | q.s. | q.s. |
| Deionized Water to 100% | q.s. | q.s. |
| Viscosity mPa · s | | |
| Immediate | 8,160 | 6,000 |
| 24 hour | 8,820 | 8,650 |
| % Clarity | 73.1 | 95.2 |
| HHCR@90% RH | | |
| T@70% CR | 1.25 | 0.5 |
| % CR@T-0.25 | 92 | 87 |
| % CR@T-0.75 | 88 | 44 |
| % CR@T-1.25 | 88 | 22 |
| % CR@T-3 | 50 | 22 |
| % CR@T-8 | 42 | 22 |
| % CR@T-24 | 38 | 22 |
| Subjective Property Ratings | | |
| Feel | 4 | 4 |
| Spreadability | 5 | 5 |
| Combing | 3.5 | 3.5 |
| Curl Memory | 3 | 0 |
| Residue | 0 | 0 |

Note 4.
CARBOPOL ® Ultrez 10 polymer, Noveon, Inc.

The data show that, at a concentration of 1.2% active polymer weight, the SYNTHALEN® W2000 polymer (Ex. 63A) performed as a rheology modifying fixative hair setting agent, provided very good hair setting efficacy for at least about 1.25 hours and was judged more effective than the high concentration of PVP/VA (Ex. 63B).

EXAMPLE 64

Hydro-Alcoholic Conditioning Hair Setting Gel

This example illustrates the use of three commercial HASE polymers as the sole rheology modifying and fixative hair setting polymer at an active polymer weight of about 3% in a hydro-alcoholic, conditioning formulation, compared to a conventional fixative polymer, PVP/VA (Ex. 64A) at the same concentration. The commercial HASE polymers employed were SYNTHALEN® W2000 (Ex. 64B), STRUCTURE® 2001 (Ex. 64C) and SALCARE® SC80 (Ex. 64D). The composition containing PVP/VA included a carbomer gellant. The formulation employed is shown in Table 30 and the pH of compositions was adjusted with triethanolamine (TEA) to a range of about pH 6–6.5 as indicated.

TABLE 30

| Ingredient INCI/Trade Name | Weight % (active) | | | |
|---|---|---|---|---|
| | Ex. 64A | Ex. 64B | Ex. 64C | Ex. 64D |
| Phase A | | | | |
| Deionized water to 100% | q.s. | q.s. | q.s. | q.s. |
| PVP/VA | 3 | — | — | — |
| STRUCTURE ® 2001 | — | 3 | — | — |
| SYNTHALEN ® W2000 | — | — | 3 | — |
| SALCARE ® SC80 | — | — | — | 3 |
| Carbomer (Note 4, Ex. 63) | 0.5 | — | — | — |
| Phase B | | | | |
| Ethanol SD-40 | 20 | 10 | 10 | 10 |
| Panthenol | 0.1 | 0.1 | 0.1 | 0.1 |
| Phase C | | | | |
| Oleth-20 | 0.4 | 0.4 | 0.4 | 0.4 |
| Fragrance | 0.1 | 0.1 | 0.1 | 0.1 |
| Dimethicone copolyol | 0.1 | 0.1 | 0.1 | 0.1 |
| PEG-45 Palm kernel glycerides | 0.02 | 0.02 | 0.02 | 0.02 |
| Part D | | | | |
| UV Stabilizer | q.s. | q.s. | q.s. | q.s. |
| D&C Green #5 (0.1% Aqueous) | 1.77 | 1.77 | 1.77 | 1.77 |
| TEA to pH indicated | q.s. | q.s. | q.s. | q.s. |
| pH | 6.4 | 6.4 | 6.4 | 6.4 |
| Viscosity mPa · s | | | | |
| Immed. | 38,800 | 48,800 | 60,400 | 73,400 |
| 24 hours | 38,800 | 54,800 | 56,900 | 64,200 |

The compositions were prepared by admixing the ingredients of Phase A for about 15 minutes or until the mixture was homogenous. The ingredients of Phase B were premixed and then added to Phase A, and blended therein for about 15 minutes or until the admixture was homogeneous. The ingredients of Phase C were premixed and then added to the foregoing admixture and blended for about 15 minutes or until a homogenous stock solution was obtained. The ingredients of Phase D were premixed, employing a sufficient acid-neutralizing amount of TEA and the premix was then added to the stock solution and mixed therein for about 15 minutes. The pH was checked and adjusted, if necessary, with additional TEA, to the desired pH.

The hair setting efficacy determined by Method F and subjective property ratings determined by Method G are shown in Table 30A.

TABLE 30A

| | Ex. 64A | Ex. 64B | Ex. 64C | Ex. 64D |
|---|---|---|---|---|
| HHCR@90% RH | | | | |
| T@70% CR | 0.5 | 3 | 0.75 | 0.75 |
| % CR@T-0.5 | 84 | 92 | 84 | 87 |
| % CR@T-0.75 | 63 | 92 | 84 | 83 |
| % CR@T-1.75 | 21 | 92 | 60 | 61 |
| % CR@T-3 | 21 | 79 | 50 | 44 |
| % CR@T-8 | 21 | 57 | 38 | 35 |
| % CR@T-24 | 21 | 53 | 38 | 27 |
| Subjective Property Rating | | | | |
| Feel | 4 | 4 | 4 | 4 |
| Spreadability | 4 | 5 | 5 | 4 |
| Combing | 4 | 4 | 4 | 4 |

TABLE 30A-continued

| | Ex. 64A | Ex. 64B | Ex. 64C | Ex. 64D |
|---|---|---|---|---|
| Curl Memory | 2 | 3 | 3 | 2 |
| Residue | 3 | 4 | 4 | 4 |

The data show that at 3% active polymer concentration, the commercial HASE polymers (Ex. 64C, 64D) provided good hair setting efficacy for at least 0.75 hours and, one case (Ex. 64B) provided excellent hair setting efficacy as long as three hours. All-of the HASE Polymers were more effective than PVP/VA (Ex. 64A) in hair setting efficacy.

In a further example, a series of hydro-alcoholic gels were prepared containing ASAP, Polymer G, H, I, or J at an active polymer weight % of about 3.5–4% ASAP, about 10–30% ethanol and a relatively low total amount (<0.2%) of hair conditioning agents (panthenol and dimethicone copolyol), preservative, solubilized fragrance and product colorant, neutralized with TEA to a pH of about 6–6.5. These compositions had a viscosity in the range of about 7,500 mPa·s to about 90,000 mPa·s. The specular gloss produced by these compositions was determined by Method D. At an angle of 20°, the gloss values were in the range of about 40 to about 60 units and at an angle of 60°, the gloss values were in the range of about 85 to about 90 units. These hydro-alcoholic compositions were also judged suitable for hair setting and set maintenance products.

In contrast, a similar hydro-alcoholic gel containing 8.5% PVP/VA, gelled with carbomer as in Ex. 64A, having about pH 6 and a viscosity of about 43,000 mPa·s had a low gloss value (2.8 at an angle of 20° and 19.6 at an angle of 60°).

EXAMPLE 65

Texture Analysis Evaluation

The crispness or softness of hair tresses treated with the hair setting gels of Ex. 12A and Ex. 21B, respectively containing ASAP, Polymer N (1.5%) and Polymer J (1.2%) was compared to that of hair treated with the hair setting gel of Ex. 37A containing PVP (3%) and untreated hair by the Hair Loop Test and Force Measurement Procedure described in Method H(1) over a time period of about 2400 seconds. Tresses having a peak force of 50 g or more were judged-as crisp, and below 50 g were judged soft.

Initially, the Polymer J gel (Ex. 21B) produced a crispness similar to that of the PVP gel (Ex. 37A) (initial peak force of about 100 g or more). The Polymer J tress, however, sustained its crispness, maintaining a substantially uniform peak force greater than about 75 g throughout the test period whereas the PVP tress softened (peak force) continuously decreased. The Polymer N gel (Ex. 12A) produced a low crisp (initial peak force near 50 g) but was judged more crisp than the untreated hair control. Surprisingly, Polymer N conditioned and softened the tress, yet the tress sustained a substantially uniform peak force of about 40 g throughout the test period. The untreated hair control was soft (initial peak force of about 40 g) and deformed easily with minimal applied peak-force (less than 20 g).

The restylability of the Polymer J and Polymer N set tresses was also evaluated as described in Method H(1) over a test period of about 2400 seconds. Polymer J again produced an initial crispness (initial peak force of more than 10 g), and then maintained a peak force greater than 75 g for about 1500 seconds and greater than about 60 g for the remaining test period. Polymer N again sustained a substantially uniform peak force of above about 30 g.

EXAMPLE 66

Restylability by % Curl Retention

The restylability of hair set with the hair setting gels of Example 5, containing 1.2% Polymer C, and Example 9, containing 1.2% Polymer A, was evaluated by determining high humidity resistance (HHCR), restyling and evaluating HHCR again as described in Method F (Cycles 1 and 2) over a total test period of about 24 hours (Table 31).

TABLE 31

Restylability of ASAP Hair Setting Agents

HHCR@90% RH

| | | Cycle 1 | | | Cycle 2 | |
|---|---|---|---|---|---|---|
| Hair Styling Gel | T@ 70% CR | % CR@ T-8 | % CR@ T-24 | T@70% CR | % CR@ T-8 | % CR@ T-24 |
| Polymer C, Ex. 5 | 24 | 97 | 97 | 24 | 87 | 80 |
| Polymer A, Ex. 9 | 24 | 84 | 84 | 24 | 94 | 90 |

As shown in Table 31, the ASAP RMHS polymers exhibited excellent restylability. After Cycle 2, the restyled hair tresses had a crisp feel. The tresses were combed through several times to evaluate the ease of combing and to evaluate any flaking or residue from the hair setting agent from combing. All hair tresses were judged easy to comb and no flaking residue was visible on the comb or hair after combing. The hair tresses were also very soft and the curl memory was good (bouncy curl).

EXAMPLE 67

Comb-Through by Texture Analysis Evaluation

The ease of combing of hair that was set with hair setting gels containing ASAP, 1.2% Polymer J (Ex. 21B) and 1.2% Polymer K (Ex. 10), was measured instrumentally by the Comb-Through Measurement Procedure of Method H(2) and the ECF value determined. For comparison, untreated hair and hair set with 3% PVP (Ex. 37A) were also measured. The data are shown in Table 32.

TABLE 32

| | Easy Comb-Through Factor (ECF) | |
|---|---|---|
| Hair Setting Gel | Wet Hair | Dry Hair |
| Untreated hair tress | 1 | 1 |
| PVP, Ex. 37A | 1.8 | 4.06 |
| Polymer J, Ex. 21B | 1.45 | 3.81 |
| Polymer K, Ex. 10 | 1.38 | 1.77 |

A lower ECF value equates with better hair manageability for a particular hair setting agent or a particular formulation being tested. Both ASAP hair setting agents provided very easy wet combing, and overall showed easier comb-through and, thus, better manageability, on both wet and dry hair than did the comparative PVP resin.

EXAMPLE 68

Hair Setting Kit

This example illustrates a two-part hair setting kit, containing packaged RMHS emulsion product in an effective hair setting amount in one part (Container A) and an effective amount pH adjusting agent packaged in the second part (Container B).

In one kit embodiment,

Container A can contain aqueous RMHS emulsion product of Example 1 (e.g. about 10 grams of about 30 weight % active polymer emulsion product) and, optionally, fragrance (q.s.); and Container B can contain AMP (95%, e.g., about 1.5 grams).

For use, the contents of Container A are transferred to a jar or bowl (about 14–16 ounce capacity), water, preferably distilled, deionized, or soft tap water, is added e.g. about 340 grams) and the mixture is blended, and then the contents of Container B are added to the mixture, and blended with stirring until a homogeneous viscous consistency is achieved. The resulting hair setting composition is then used immediately or stored for later use.

Alternatively, the contents of Container A and/or B, can also comprise sufficient water so that the contents of one container need only be blended with the contents of the other container.

In one illustrative kit embodiment using ASAP, Polymer AT of Example 1, (about 4.3 parts by weight, about 30% total solids) was placed in one kit container (A), and the pH adjusting agent (AMP (95%), about 0.3 parts by weight) and the remaining cosmetic ingredients were placed in a second container (B), and a finished hair setting composition was prepared by hand mixing with a spatula the contents of the two containers. The resulting hair setting composition comprised, on an active weight basis, about 1.3% ASAP, Polymer AT, about 0.3% AMP, about 0.2% sorbitol, about 0.1% DL panthenol, about 0.1% glyceryl polymethacrylate (and) propylene glycol (INCI name for such a mixture sold under the tradename LUBRAJEL® CG, by Guardian Laboratories), about 0.2% propylene glycol, about 0.05% glycerin, about 0.1% metal ion chelating agent, abut 0.3% preservative, and sufficient deionized water to afford 100% final weight. The hair setting composition had a pH of about 7, a clarity of about 85%, a turbidity of about 14 NTU, and a Brookfield viscosity of about 28,400 mPa·s. Alternatively, all or a portion of the water can be added to the contents of container (A) just before mixing it with the contents of container (B) or can be incorporated in container (A) as a diluent for the polymer.

EXAMPLES 69–73

Aqueous Gels

It is known that the viscosity achieved with the commonly employed alkali-swellable, polyacrylic acid polymeric thickener, carbomer, can be negatively affected by the presence of some conventional anionic polymers. This example illustrates the surprising compatibility of the alkali-swellable ASAP with carbomer polymer, and hydrophobically-modified carbomer polymer, thickeners in aqueous gels.

A first series of aqueous gels (Examples 69–73) were prepared, each gel containing one of the following alkali-swellable ASAP of Example 1, Polymer H (Exs. 69 A–I), Polymer Y (Exs. 70 A–I), Polymer Z (Exs. 71 A–I), Polymer AT (Exs. 72 A–L), Polymer AU (Exs. 73 A–I) and either a carbomer polymer, or hydrophobically-modified carbomer polymer, as identified, and in the amount indicated, in Tables 33–37, respectively. The commercial thickener products employed having the INCI name, carbomer, were: a traditional carbomer polymer, CARBOPOL® 980 polymer, and a hydrophobically-modified carbomer polymer, CARBOPOL® Ultrez 21 polymer, both sold by Noveon, Inc. (Cleveland, Ohio). Other commercial polymers employed were: hydrophobically-modified carbomer polymer, CARBOPOL® ETD 2020 polymer, also sold by Noveon, Inc., having the INCI name, Acrylates/$C_{10-30}$ Alkyl Acrylate Crosspolymer, and STABYLEN® 30, sold by 3V Inc., having the INCI name, Acrylates/Vinyl Isodecanoate.

The aqueous hair setting gels were prepared by dispersing the selected commercial polymeric thickener in a portion of the total water content, neutralizing the dispersion with AMP (95%) to a pH in the range of about 6–6.5, then adding the selected amount of aqueous emulsion of alkali-swellable ASAP of Example 1, and adjusting the water content and pH, if needed, to maintain the foregoing pH or clarity. Alternatively, the polymers can be pre-mixed and then neutralized to provide similar gels. The pH, % clarity, and viscosity (24-hour) of the gels is shown in Tables 33–37.

TABLE 33

| Ex. No. | Polymer in Gel | Active Wt. % | pH | % Clarity | Viscosity mPa·s (24 hours) |
|---|---|---|---|---|---|
| 69A | Polymer H, Ex. 1 | 0.5 | 6.4 | 90.2 | 47,600 |
|  | CARBOPOL® ETD 2020 | 0.5 |  |  |  |
| 69B | Polymer H, Ex. 1 | 0.75 | 6.2 | 84.4 | 64,200 |
|  | CARBOPOL® ETD 2020 | 0.5 |  |  |  |
| 69C | Polymer H, Ex. 1 | 1 | 6.4 | 89.6 | 65,800 |
|  | CARBOPOL® ETD 2020 | 0.25 |  |  |  |
| 69D | Polymer H, Ex. 1 | 0.5 | 6.4 | 92.8 | 42,800 |
|  | CARBOPOL® 980 | 0.5 |  |  |  |
| 69E | Polymer H, Ex. 1 | 0.75 | 6.4 | 90.2 | 52,000 |
|  | CARBOPOL® 980 | 0.5 |  |  |  |
| 69F | Polymer H, Ex. 1 | 1 | 6.5 | 90.9 | 49,200 |
|  | CARBOPOL® 980 | 0.25 |  |  |  |
| 69G | Polymer H, Ex. 1 | 0.5 | 6.4 | 93.7 | 72,200 |
|  | CARBOPOL® Ultrez 21 | 0.5 |  |  |  |
| 69H | Polymer H, Ex. 1 | 0.75 | 6.4 | 92.8 | 88,200 |
|  | CARBOPOL® Ultrez 21 | 0.5 |  |  |  |
| 69I | Polymer H, Ex. 1 | 1 | 6.4 | 93.2 | 76,600 |
|  | CARBOPOL® Ultrez 21 | 0.25 |  |  |  |

TABLE 34

| Ex. No. | Polymer in Gel | Active Wt. % | pH | % Clarity | Viscosity mPa·s (24 hours) |
|---|---|---|---|---|---|
| 70A | Polymer Y, Ex. 1 | 0.5 | 6.4 | 82.6 | 44,600 |
|  | CARBOPOL® ETD 2020 | 0.5 |  |  |  |
| 70B | Polymer Y, Ex. 1 | 0.75 | 6.3 | 79.8 | 57,800 |
|  | CARBOPOL® ETD 2020 | 0.5 |  |  |  |
| 70C | Polymer Y, Ex. 1 | 1 | 6.4 | 78.3 | 55,800 |
|  | CARBOPOL® ETD 2020 | 0.25 |  |  |  |
| 70D | Polymer Y, Ex. 1 | 0.5 | 6.4 | 88.1 | 44,700 |
|  | CARBOPOL® 980 | 0.5 |  |  |  |
| 70E | Polymer Y, Ex. 1 | 0.75 | 6.4 | 84.5 | 55,200 |
|  | CARBOPOL® 980 | 0.5 |  |  |  |
| 70F | Polymer Y, Ex. 1 | 1 | 6.4 | 88 | 50,000 |
|  | CARBOPOL® 980 | 0.25 |  |  |  |
| 70G | Polymer Y, Ex. 1 | 0.5 | 6.5 | 91.9 | 63,600 |
|  | CARBOPOL® Ultrez 21 | 0.5 |  |  |  |
| 70H | Polymer Y, Ex. 1 | 0.75 | 6.5 | 92 | 81,800 |
|  | CARBOPOL® Ultrez 21 | 0.5 |  |  |  |

TABLE 34-continued

| Ex. No. | Polymer in Gel | Active Wt. % | pH | % Clarity | Viscosity mPa·s (24 hours) |
|---|---|---|---|---|---|
| 70I | Polymer Y, Ex. 1 | 1 | 6.5 | 91.3 | 59,800 |
|  | CARBOPOL® Ultrez 21 | 0.25 |  |  |  |

TABLE 35

| Ex. No. | Polymer in Gel | Active Wt. % | pH | % Clarity | Viscosity mPa·s (24 hours) |
|---|---|---|---|---|---|
| 71A | Polymer Z, Ex. 1 | 0.5 | 6.3 | 76.9 | 40,200 |
|  | CARBOPOL® ETD 2020 | 0.5 |  |  |  |
| 71B | Polymer Z, Ex. 1 | 0.75 | 6.5 | 81.2 | 57,200 |
|  | CARBOPOL® ETD 2020 | 0.5 |  |  |  |
| 71C | Polymer Z, Ex. 1 | 1 | 6.4 | 80.9 | 36,200 |
|  | CARBOPOL® ETD 2020 | 0.25 |  |  |  |
| 71D | Polymer Z, Ex. 1 | 0.5 | 6.5 | 88.9 | 34,400 |
|  | CARBOPOL® 980 | 0.5 |  |  |  |
| 71E | Polymer Z, Ex. 1 | 0.75 | 6.4 | 81.8 | 42,000 |
|  | CARBOPOL® 980 | 0.5 |  |  |  |
| 71F | Polymer Z, Ex. 1 | 1 | 6.4 | 82.7 | 40,200 |
|  | CARBOPOL® 980 | 0.25 |  |  |  |
| 71G | Polymer Z, Ex. 1 | 0.5 | 6.5 | 90.5 | 51,200 |
|  | CARBOPOL® Ultrez 21 | 0.5 |  |  |  |
| 71H | Polymer Z, Ex. 1 | 0.75 | 6.5 | 90.1 | 59,800 |
|  | CARBOPOL® Ultrez 21 | 0.5 |  |  |  |
| 71I | Polymer Z, Ex. 1 | 1 | 6.5 | 89.3 | 45,900 |
|  | CARBOPOL® Ultrez 21 | 0.25 |  |  |  |

TABLE 36

| Ex. No. | Polymer in Gel | Active Wt. % | pH | % Clarity | Viscosity mPa·s (24 hours) |
|---|---|---|---|---|---|
| 72A | Polymer AT, Ex. 1 | 0.5 | 6.5 | 87.5 | 56,400 |
|  | CARBOPOL® ETD 2020 | 0.5 |  |  |  |
| 72B | Polymer AT, Ex. 1 | 0.75 | 6.5 | 85.5 | 83,200 |
|  | CARBOPOL® ETD 2020 | 0.5 |  |  |  |
| 72C | Polymer AT, Ex. 1 | 1 | 6.5 | 80.9 | 45,600 |
|  | CARBOPOL® ETD 2020 | 0.25 |  |  |  |
| 72D | Polymer AT, Ex. 1 | 0.5 | 6.5 | 84.7 | 45,800 |
|  | CARBOPOL® 980 | 0.5 |  |  |  |
| 72E | Polymer AT, Ex. 1 | 0.75 | 6.5 | 82.7 | 62,800 |
|  | CARBOPOL® 980 | 0.5 |  |  |  |
| 72F | Polymer AT, Ex. 1 | 1 | 6.5 | 81.1 | 39,200 |
|  | CARBOPOL® 980 | 0.25 |  |  |  |
| 72G | Polymer AT, Ex. 1 | 0.5 | 6.5 | 88.1 | 72,800 |
|  | CARBOPOL® Ultrez 21 | 0.5 |  |  |  |
| 72H | Polymer AT, Ex. 1 | 0.75 | 6.5 | 84.6 | 98,200 |
|  | CARBOPOL® Ultrez 21 | 0.5 |  |  |  |
| 72I | Polymer AT, Ex. 1 | 1 | 6.5 | 84.5 | 67,400 |
|  | CARBOPOL® Ultrez 21 | 0.25 |  |  |  |
| 72J | Polymer AT, Ex. 1 | 0.5 | 6.5 | 77.8 | 39,400 |
|  | STABYLEN® 30 | 0.5 |  |  |  |
| 72K | Polymer AT, Ex. 1 | 0.75 | 6.4 | 71.8 | 43,200 |
|  | STABYLEN® 30 | 0.5 |  |  |  |
| 72L | Polymer AT, Ex. 1 | 1 | 6.4 | 66.5 | 31,800 |
|  | STABYLEN® 30 | 0.25 |  |  |  |

TABLE 37

| Ex. No. | Polymer in Gel | Active Wt. % | pH | % Clarity | Viscosity mPa·s (24 hours) |
|---|---|---|---|---|---|
| 73A | Polymer AU, Ex. 1 | 0.5 | 6.4 | 88.6 | 57,800 |
|  | CARBOPOL® ETD 2020 | 0.5 |  |  |  |

TABLE 37-continued

| Ex. No. | Polymer in Gel | Active Wt. % | pH | % Clarity | Viscosity mPa·s (24 hours) |
|---|---|---|---|---|---|
| 73B | Polymer AU, Ex. 1 CARBOPOL ® ETD 2020 | 0.75 0.5 | 6.5 | 89.5 | 73,400 |
| 73C | Polymer AU, Ex. 1 CARBOPOL ® ETD 2020 | 1 0.25 | 6.5 | 87.9 | 55,800 |
| 73D | Polymer AU, Ex. 1 CARBOPOL ® 980 | 0.5 0.5 | 6.5 | 89.9 | 43,400 |
| 73E | Polymer AU, Ex. 1 CARBOPOL ® 980 | 0.75 0.5 | 6.5 | 89.8 | 58,200 |
| 73F | Polymer AU, Ex. 1 CARBOPOL ® 980 | 1 0.25 | 6.5 | 89.3 | 47,600 |
| 73G | Polymer AU, Ex. 1 CARBOPOL ® Ultrez 21 | 0.5 0.5 | 6.5 | 89.2 | 70,000 |
| 73H | Polymer AU, Ex. 1 CARBOPOL ® Ultrez 21 | 0.75 0.5 | 6.5 | 85.8 | 79,800 |
| 73I | Polymer AU, Ex. 1 CARBOPOL ® Ultrez 21 | 1 0.25 | 6.5 | 88.5 | 51,600 |

The HHCR hair setting efficacy of the aqueous gels of Examples 69 G–I, 70 A–I, 71 A–C and G–I, 72 A–C and G–L, and 73 A–C and G–I was determined by Method F over a 24-hour period.

The hair setting efficacy was judged very good to excellent. The HHCR results, T @70% CR, were: about 1.25 hours for Ex. 71A; about 1.75 hours for Exs. 70H, 72J, 72K; about 3 hours for Exs. 70D, 70G, 72H, 72L; about 4 hours for Exs. 70A, 73G; about 5 hours for Ex. 72C; about 6 hours for Exs. 70E, 73B, 73H; about 7 hours for Ex. 73I; about 8 hours for Exs. 70F, 71B, 71C, 71G, 72I, 73A; and about 24 hours for Exs. 69G, 69H, 69I, 70B, 70C, 70I, 71H, 71I, 72A, 72B, 72G and 73C.

The results show that ASAP can be employed in combination with either conventional carbomer or hydrophobically-modified carbomer thickeners in aqueous gel without sacrificing viscosity.

For comparison, the viscosity achieved in an aqueous gel with AMP-neutralized commercial polymers in the absence of alkali-swellable ASAP is shown in Table 38.

TABLE 38

| Commercial Polymer in Gel | Active Wt. % | pH | Viscosity mPa·s (24 hours) |
|---|---|---|---|
| CARBOPOL ® ETD 2020 | 0.5 | 6.3 | 26,500–26,600 |
| CARBOPOL ® ETD 2020 | 0.25 | 6.3 | 16,650 |
| CARBOPOL ® 980 | 0.5 | 6.4 | 43,800 |
| CARBOPOL ® 980 | 0.25 | 6.4 | 27,900 |
| CARBOPOL ® Ultrez 21 | 0.5 | 6.4 | 46,800–46,950 |
| CARBOPOL ® Ultrez 21 | 0.25 | 6.4 | 35,600 |
| STABYLEN ® 30 | 0.5 | 6.5 | 16,100 |
| STABYLEN ® 30 | 0.25 | 6.5 | 12,600 |

The foregoing examples generally illustrate that RMHS polymers provided both hair setting efficacy and rheology modification while retaining aesthetically desirable clarity in aqueous media. The ASAP hair setting polymers were generally judged more effective hair setting agents than HASE polymers, and provided surprisingly very good to excellent sustained hair setting efficacy. HASE polymers were also surprisingly effective hair setting agents and provided rheology modification, in the foregoing examples.

The foregoing discussion and reported studies are intended to be illustrative of the present invention and are not to be taken as limiting. Still other variants within the spirit and scope of this invention are possible and will readily present themselves to those skilled in the art.

We claim:

1. An aqueous hair setting composition comprising an effective hair setting amount of a rheology modifying hair setting associative polymer which is the polymerization product of a monomer mixture comprising:
   (a) about 10 to about 75 weight percent of at least one acidic vinyl monomer or a salt thereof;
   (b) about 10 to about 90 weight percent of at least one nonionic vinyl monomer;
   (c) about 0.1 to about 25 weight percent of a first associative monomer having a first hydrophobic end group;
   (d) about 0.1 to about 25 weight percent of at least one monomer selected from the group consisting of a second associative monomer having a second hydrophobic end group, a semihydrophobic monomer, and a combination thereof; and, optionally,
   (e) up to about 20 weight percent of a monomer selected from the group consisting of a crosslinking monomer, a chain transfer agent, and a combination thereof:
   wherein the associative polymer is substantially the sole hair setting agent in the composition.

2. The composition of claim 1 wherein the first and second hydrophobic end groups are each independently selected from the group of hydrocarbon classes consisting of a $C_8$–$C_{40}$ linear alkyl, a $C_8$–$C_{40}$ branched alkyl, a $C_2$–$C_{40}$ carbocyclic alkyl, a $C_2$–$C_{40}$ alkyl-substituted phenyl, an aryl-substituted $C_2$–$C_{40}$ alkyl, and a $C_8$–$C_{80}$ complex ester.

3. The composition of claim 1 wherein the acidic vinyl monomer is selected from the group consisting of a carboxylic acid-containing vinyl monomer, a sulfonic acid-containing vinyl monomer, a phosphonic acid-containing vinyl monomer, and a combination thereof.

4. The composition of claim 1 wherein the acidic vinyl monomer is acrylic acid, methacrylic acid, styrenesulfonic acid, 2-acrylamido-2-methylpropane sulfonic acid, or a combination thereof.

5. The composition of claim 1 wherein the salt is selected from the group consisting of an alkali metal salt, an alkaline earth metal salt, an ammonium salt, and an alkyl-substituted ammonium salt, and a combination thereof.

6. The composition of claim 1 wherein the nonionic vinyl monomer is a compound having one of the following formulas (I) or (II):

$$CH_2\!=\!C(X)Z \qquad (I)$$

$$CH_2\!=\!CH\!-\!OC(O)R \qquad (II)$$

wherein, in each of formulas (I) and (II), X is H or methyl; Z is $-C(O)OR^1$, $-C(O)NH_2$, $-C(O)NHR^1$, $-C(O)N(R^1)_2$, $-C_6H_4R^1$, $-C_6H_4OR^1$, $-C_6H_4Cl$, $-CN$, $-NHC(O)CH_3$, $-NHC(O)H$, N-(2-pyrrolidonyl), N-caprolactamyl, $-C(O)NHC(CH_3)_3$, $-C(O)NHCH_2CH_2-N$-ethyleneurea, $-SiR_3$, $C(O)O(CH_2)_xSiR_3$, $-C(O)NH(CH_2)_xSiR_3$, or $-(CH_2)_xSiR_3$; x is an integer in the range of 1 to about 6; each R is independently $C_1$–$C_{18}$ alkyl; each $R^1$ is independently $C_1$–$C_{30}$ alkyl, hydroxy-substituted $C_1$–$C_{30}$ alkyl, or halogen-substituted $C_1$–$C_{30}$ alkyl.

7. The composition of claim 1 wherein the nonionic vinyl monomer is selected from the group consisting of a $C_1$–$C_8$ ester of acrylic acid, a $C_1$–$C_8$ ester of methacrylic acid, and a mixture thereof.

8. The composition of claim 1 wherein at least one of monomer (c) and monomer (d) is a compound of the following formula (III):

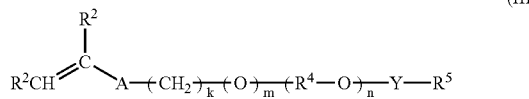

wherein, each $R^2$ is independently H, methyl, —C(O)OH, or —C(O)OR$^3$; $R^3$ is $C_1$–$C_{30}$ alkyl; A is —CH$_2$C(O)o—, —C(O)O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; $(R^4—O)_n$ is a polyoxyalkylene, which is a homopolymer, a random copolymer, or a block copolymer of $C_2$–$C_4$ oxyalkylene units, wherein $R^4$ is $C_2H_4$, $C_3H_6$, or $C_4H_8$, and n is an integer in the range of about 5 to about 250; Y is —$R^4$O—, —$R^4$NH—, —C(O)—, —C(O)NH—, —$R^4$NHC(O)NH—, or —C(O)NHC(O)—; and $R^5$ is a substituted or unsubstituted alkyl selected from the group consisting of a $C_8$–$C_{40}$ linear alkyl, a $C_8$–$C_{40}$ branched alkyl, a $C_8$–$C_{40}$ carbocyclic alkyl, a $C_2$–$C_{40}$ alkyl-substituted phenyl, an aryl-substituted $C_2$–$C_{40}$ alkyl, and a $C_8$–$C_{80}$ complex ester selected from a di-, tri-, and polyesters of a polyol wherein at least one hydroxyl group on said polyol is capable of being alkylated with a $C_2$–$C_7$ alkylene oxide, hydrogenated castor oil, 1,2-diacyl glycerols, di-, tri-, and polyesters of sugars, and sorbitan esters; wherein the $R^5$ alkyl group optionally comprises one or more substituents selected from the group consisting of a hydroxyl group, an alkoxyl group, and a halogen group.

9. The composition of claim 1 wherein monomer (d) comprises a semihydrophobic monomer which is a compound having one of the following formulas (IV) or (V):

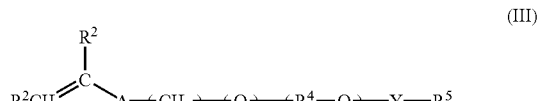

wherein, in each of formulas (IV) and (V), each $R^6$ is independently H, $C_1$–$C_{30}$ alkyl, —C(O)OH, or —C(O)OR$^7$; $R^7$ is $C_1$–$C_{30}$ alkyl; A is —CH$_2$C(O)O—, —C(O)O—, —O—, —CH$_2$O—, —NHC(O)NH—, —C(O)NH—, —Ar—(CE$_2$)$_2$NHC(O)O—, —Ar—(CE$_2$)$_z$NHC(O)NH—, or —CH$_2$CH$_2$NHC(O)—; Ar is a divalent aryl; E is H or methyl; z is 0 or 1; p is an integer in the range of 0 to about 30, and r is 0 or 1, with the proviso that when p is 0, r is 0, and when p is in the range of 1 to about 30, r is 1; $(R^8—O)_v$ is a polyoxyalkylene, which is a homopolymer, a random copolymer or a block copolymer of $C_2$–$C_4$ oxyalkylene units, wherein $R^8$ is $C_2H_4$, $C_3H_6$, or $C_4H_8$, and v is an integer in the range of about 5 to about 250, $R^9$ is H or $C_1$–$C_4$ alkyl; and D is a $C_8$–$C_{30}$ unsaturated alkyl or a carboxy-substituted $C_8$–$C_{30}$ unsaturated alkyl.

10. The composition of claim 1 wherein monomer (a) comprises about 0.1 to about 2 weight percent of a crosslinking monomer selected from the group consisting of an acrylate ester of a polyol having at least two acrylate ester groups, a methacrylate ester of a polyol having at least two methacrylate ester groups, and a combination thereof.

11. The composition of claim 1 wherein monomer (e) comprises about 0.1 to about 10 weight percent of at least one chain transfer agent.

12. The composition of claim 1 wherein the pH of the composition is at least about 2.

13. The composition of claim 1 having a Brookfield viscosity greater than about 100 mPa·s at an ambient temperature in the range of about 20–25° C.

14. The composition of claim 1 wherein the composition provides a hair setting efficacy of at least about 70% curl retention for a period of at least about 0.75 hours at about 90% relative humidity and ambient temperature in the range of about 26–27° C.

15. A composition of claim 1 further comprising one of more adjuvant selected from the group consisting of a polymer film modifying agent, a pH adjusting and buffering agent, an auxiliary hair fixative and film former, an auxiliary rheology modifier, a hair conditioning agent, a chemical hair waving or straightening agent a hair colorant, a surfactant, a polymer film modifying agent, a product finishing agent, a propellant, and a mixture thereof.

16. A composition of claim 1 wherein the composition includes an organic solvent selected from the group consisting of a $C_2$–$C_8$ monohydric alcohol, a $C_2$–$C_8$ polyol, and a mixture thereof.

17. A composition of claim 1 in the form of a liquid, gel, spray, emulsion, foam, mousse, spritz, shampoo, solid, or semisolid.

18. A composition of claim 1 wherein the composition includes a propellant selected from the group consisting of a fluorinated hydrocarbon, dimethyl ether, a liquid volatile hydrocarbon, and a compressed gas.

19. A composition of claim 1 containing about 0.1 to about 15% by weight of active associative polymer.

20. A composition of claim 1 further comprising an auxiliary rheology modifying polymer.

21. A composition of claim 20 wherein the auxiliary rheology modifying polymer is a carbomer polymer or a hydrophobically-modified carbomer polymer.

22. An article of manufacture comprising a composition of claim 1 in a packaged form.

23. The article of manufacture of claim 22 wherein the packaged form comprises a hair setting aid.

24. The composition of claim 8 wherein said hydrogenated castor oil comprises a triglyceride of 12-hydroxy steric acid.

* * * * *

UNITED STATES PATENT AND TRADEMARK OFFICE
CERTIFICATE OF CORRECTION

PATENT NO. : 7,153,496 B2
APPLICATION NO. : 10/338510
DATED : December 26, 2006
INVENTOR(S) : Krishnan Tamareselvy and Kittie L. Ramey It is certified that error appears in the above-identified patent and that said Letters Patent is hereby corrected as shown below:

In column 66, line 31, the term "$C_2$-$C_{40}$" should be changed to --$C_8$-$C_{40}$--.

In column 66, line 59, the term "$C(O)O(CH_2)_x SiR_3$" should be changed to -- -$C(O)O(CH_2)_x SiR_3$--.

In column 67, line 13, the term "-$CH_2C(O)o$-," should be changed to -- -$CH_2C(O)O$- --.

In column 67, line 14, insert the term -- -O- -- after "-C(O)O-".

In column 67, line 15, the term "-Ar-$(CE_2)$ $_z$-NHC(O)O-" should be changed to -- -Ar-$(CE_2)_z$-NHC(O)O- --.

In column 67, lines 42 to 48, formula (III) should be deleted and replaced with:

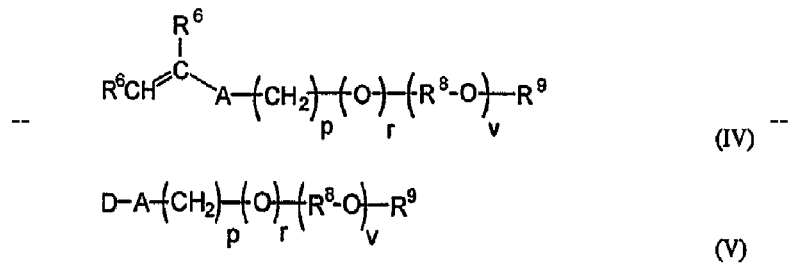

In column 67, line 53, the term "-Ar-$(CE_2)_2$NHC(O)O-" should be replaced with -- -Ar-$(CE_2)_z$NHC(O)O- --.

In column 68, line 5, the term "monomer (a)" should be changed to --monomer (e)--.

UNITED STATES PATENT AND TRADEMARK OFFICE
CERTIFICATE OF CORRECTION

PATENT NO. : 7,153,496 B2
APPLICATION NO. : 10/338510
DATED : December 26, 2006
INVENTOR(S) : Krishnan Tamareselvy and Kittie L. Ramey It is certified that error appears in the above-identified patent and that said Letters Patent is hereby corrected as shown below:

In column 68, line 29, the term "straightening agent a hair colorant" should be replaced with --straightening agent, a hair colorant--

Signed and Sealed this

Thirteenth Day of March, 2007

JON W. DUDAS
*Director of the United States Patent and Trademark Office*